US010687961B1

(12) United States Patent
Abdelgany et al.

(10) Patent No.: US 10,687,961 B1
(45) Date of Patent: Jun. 23, 2020

(54) EXPANDABLE INTERBODY AND SYSTEM

(71) Applicant: Custom Spine Acquisition, Inc., Marietta, GA (US)

(72) Inventors: Mahmoud F. Abdelgany, Rockaway, NJ (US); Kevin Sichler, West Orange, NJ (US); Aaron Markworth, Flanders, NJ (US); Younghoon Oh, Montville, NJ (US)

( * ) Notice: Subject to any disclaimer, the term of this patent is extended or adjusted under 35 U.S.C. 154(b) by 632 days.

(21) Appl. No.: 14/320,844

(22) Filed: Jul. 1, 2014

Related U.S. Application Data

(60) Provisional application No. 61/841,796, filed on Jul. 1, 2013, provisional application No. 61/884,966, filed on Sep. 30, 2013.

(51) Int. Cl.
*A61F 2/44* (2006.01)

(52) U.S. Cl.
CPC .................................... *A61F 2/447* (2013.01)

(58) Field of Classification Search
CPC .......... A61F 2/44; A61F 2/442; A61F 2/4425; A61F 2/4455; A61F 2/446; A61F 2/4465; A61F 2/447
USPC ................. 623/17.11, 17.15, 17.16
See application file for complete search history.

(56) References Cited

U.S. PATENT DOCUMENTS

| 6,685,742 | B1 | 2/2004 | Jackson | |
|---|---|---|---|---|
| 7,608,107 | B2 | 10/2009 | Michelson | |
| 8,771,358 | B2 | 7/2014 | Michelson | |
| 8,795,366 | B2 | 8/2014 | Varela | |
| 8,828,018 | B2 | 9/2014 | Ragab et al. | |
| 8,828,085 | B1 | 9/2014 | Jensen | |
| 8,845,734 | B2 * | 9/2014 | Weiman | A61F 2/442 623/17.16 |
| 2014/0148904 | A1 * | 5/2014 | Robinson | A61F 2/447 623/17.16 |
| 2014/0277508 | A1 * | 9/2014 | Baynham | A61F 2/447 623/17.16 |

OTHER PUBLICATIONS

"New Products Increase Surgical Options in Lumbar Procedures"; Medtronic; Oct. 23, 2012; http://newsroom.medtronic.com/phoenix.zhtml?c=251324&p=irol-newsArticle&ID=1774774&highlight=.
"Spine Wave Announces U.S. FDA's 510K Clearance of the StaXx® IB System, an Intervertebral Body Fusion Device"; Source: Spine Wave, Inc.; Apr. 29, 2013 08:00 ET; http://www.marketwired.com/press-release/spine-wave-announces-us-fdas-510k-clearance-staxxr-ib-system-intervertebral-body-fusion-1783730.htm.

* cited by examiner

*Primary Examiner* — Si Ming Ku

(57) ABSTRACT

An expanding interbody includes a first articulating member; a second articulating member rotatably connected to the first articulating member; and a clip member that engages each of the first articulating member and the second articulating member, wherein any of the first articulating member and the second articulating member includes a plurality of grooves arranged in a progressively elongated arrangement, and wherein the clip member includes at least one protruding tip that sequentially engages the plurality of grooves causing the first articulating member to rotate with respect to the second articulating member.

18 Claims, 44 Drawing Sheets

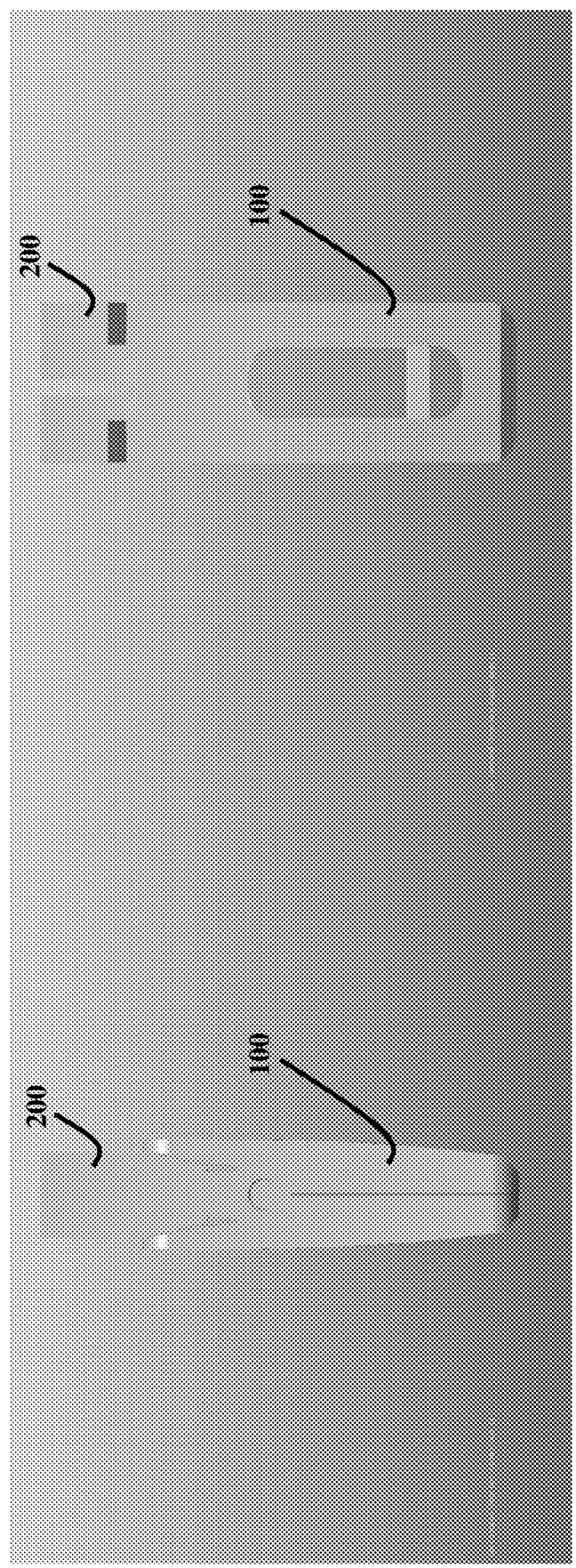

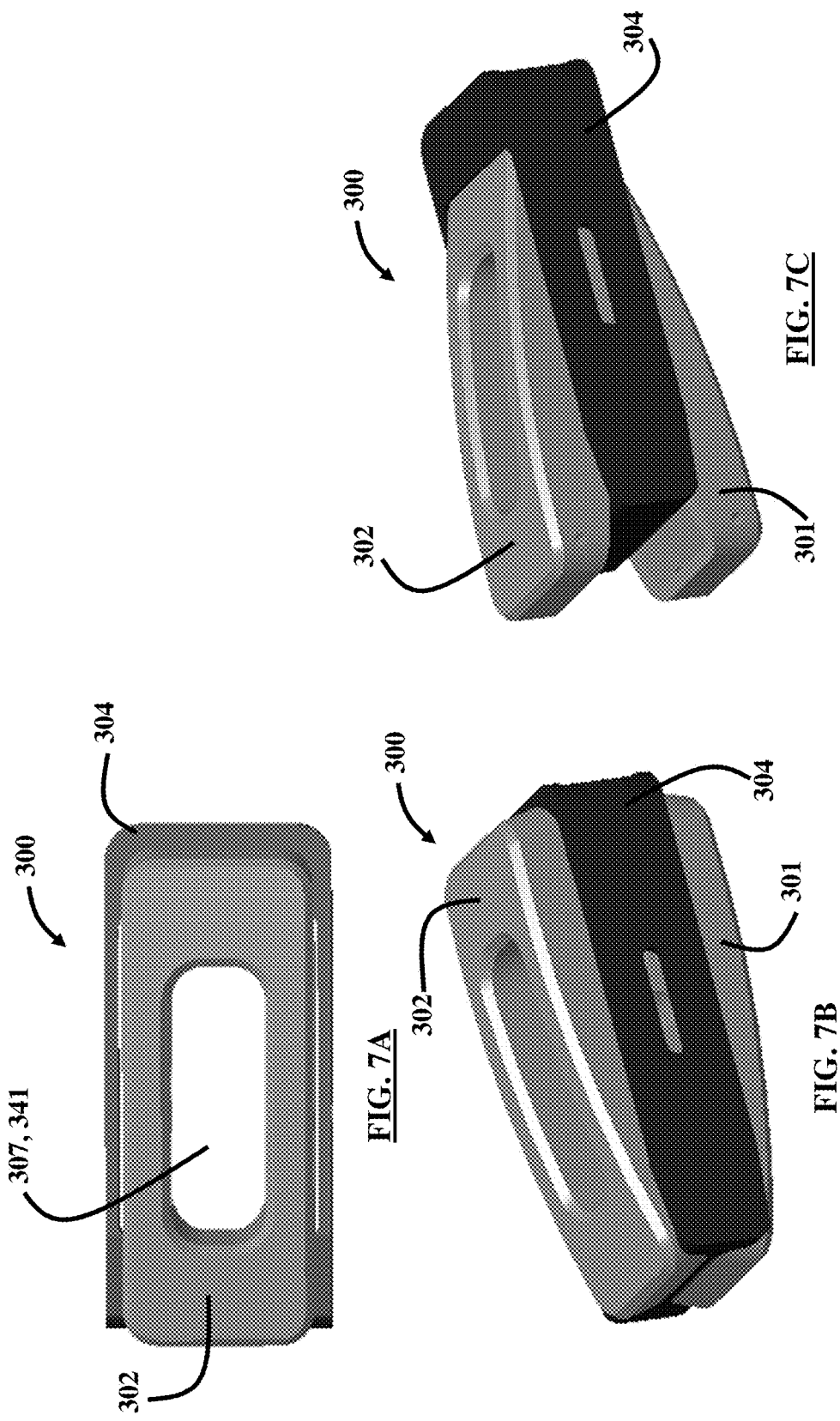

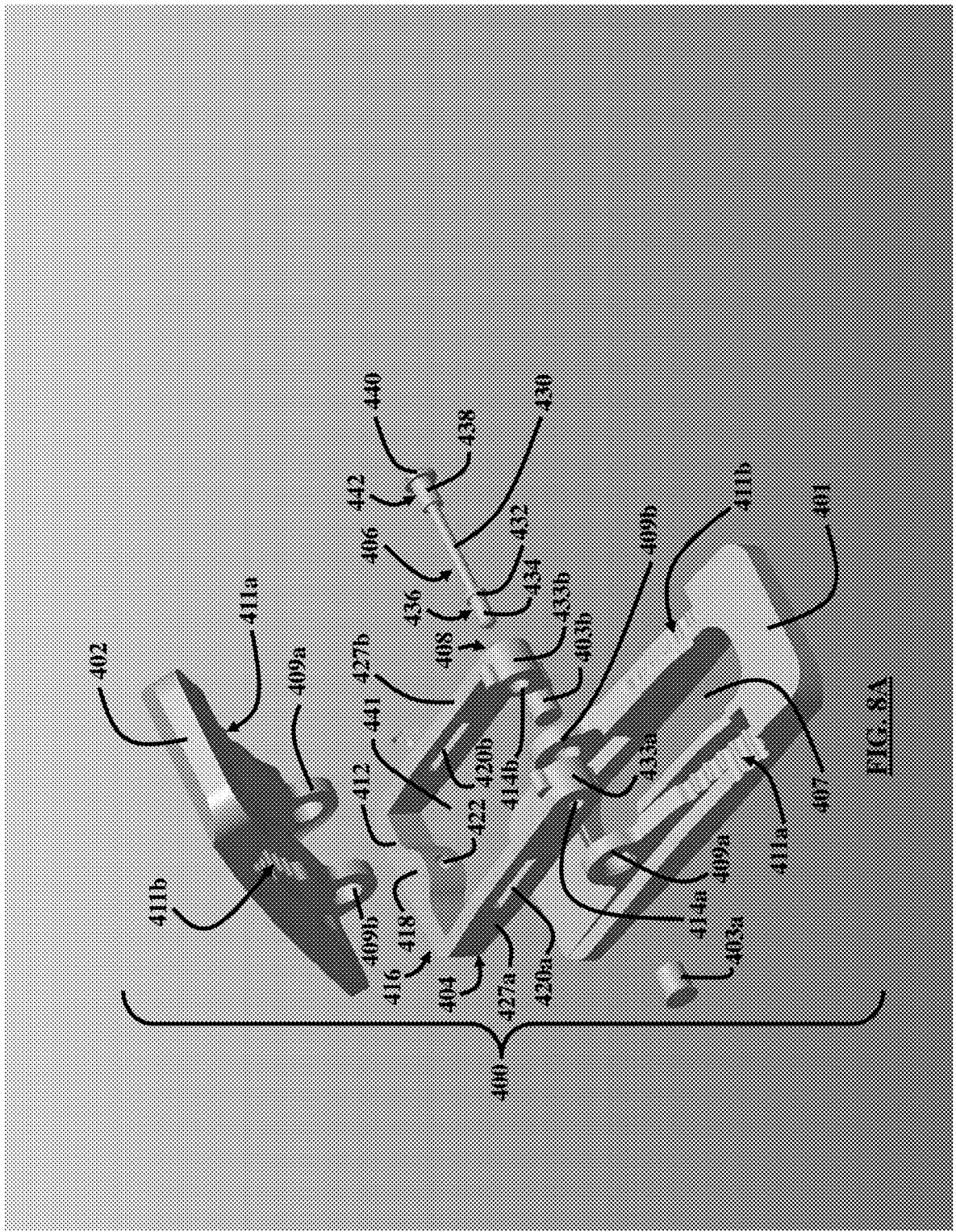

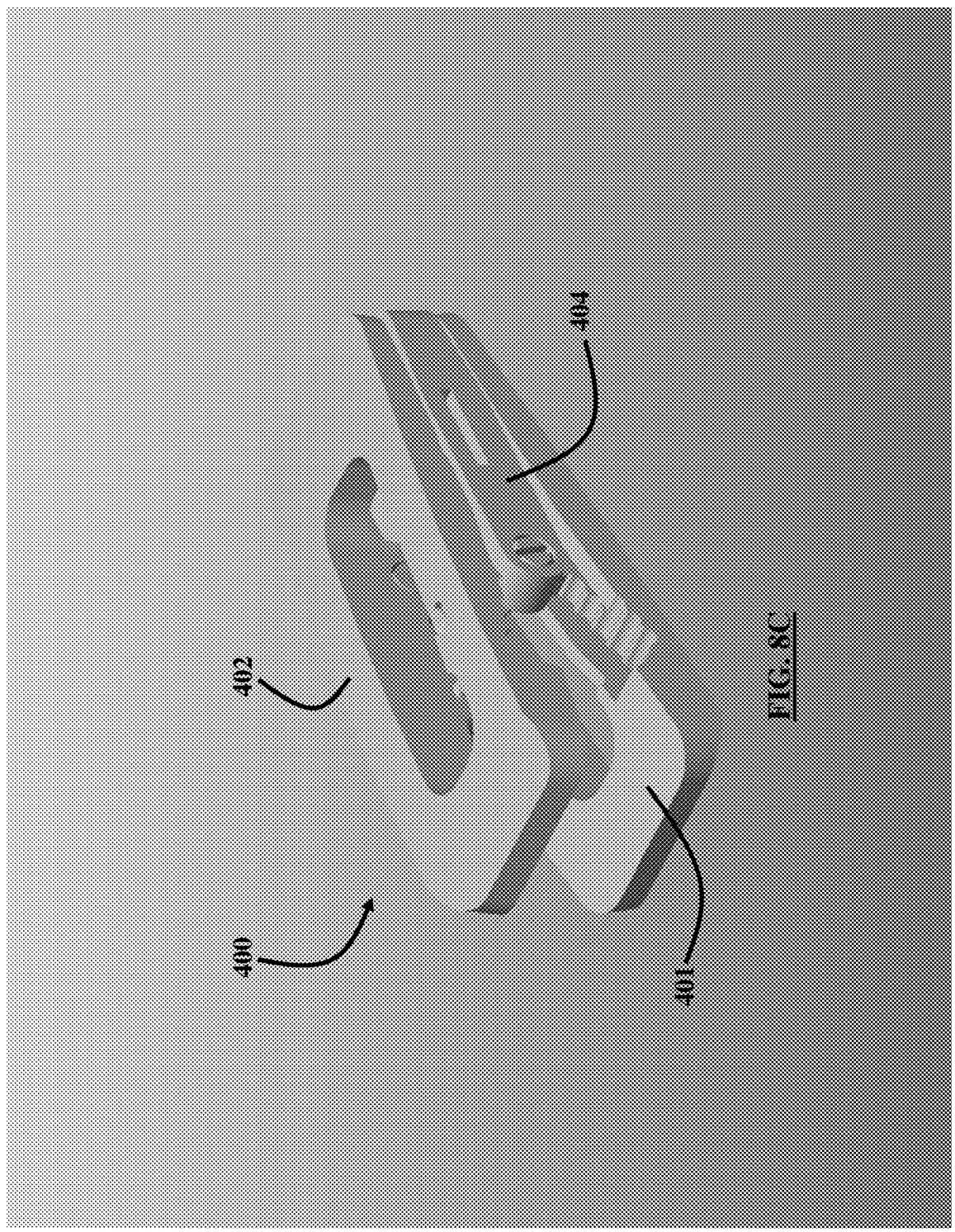

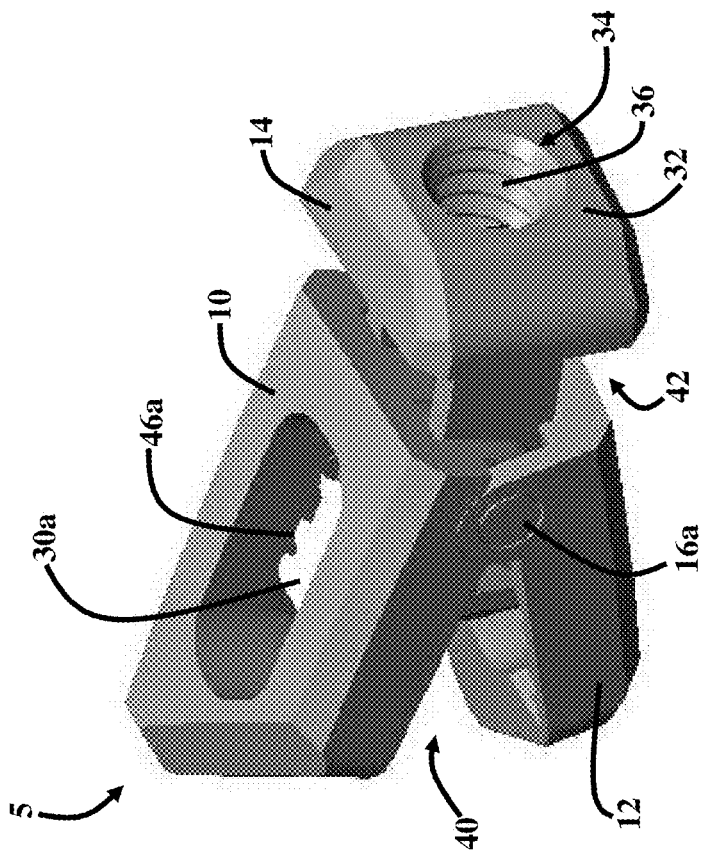
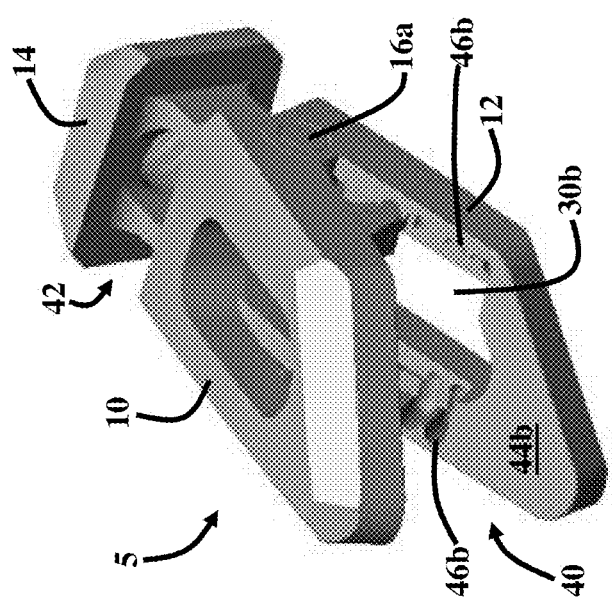
FIG. 9H
FIG. 9G

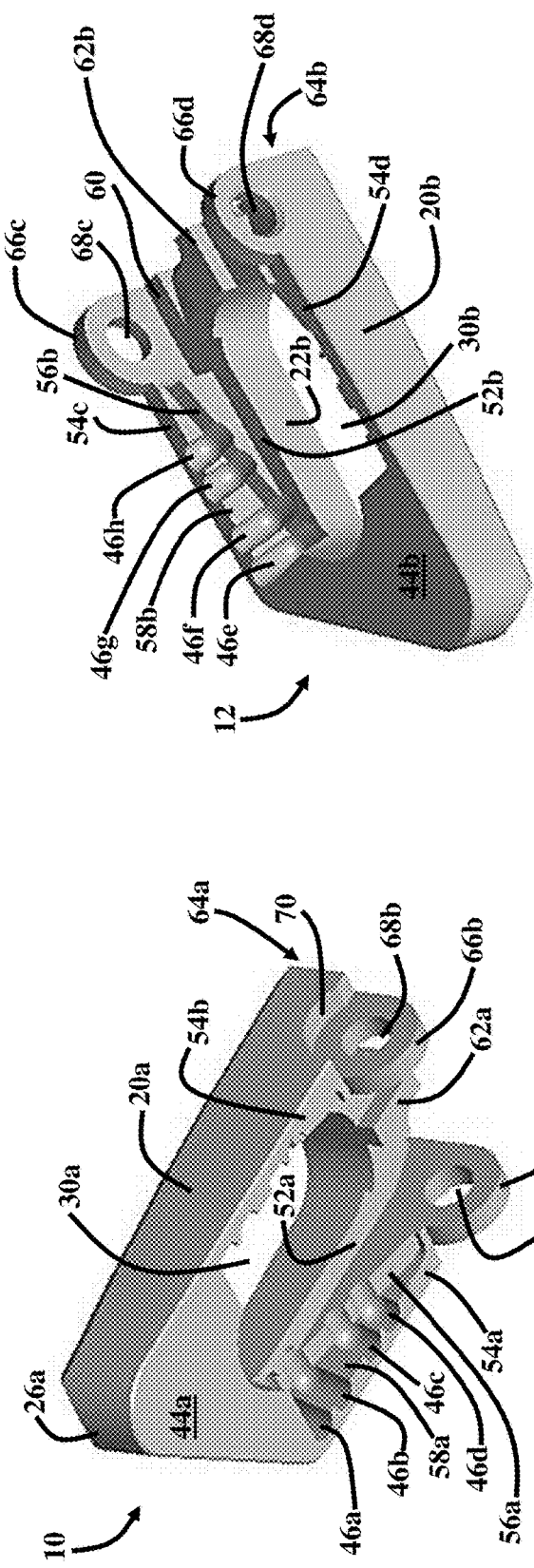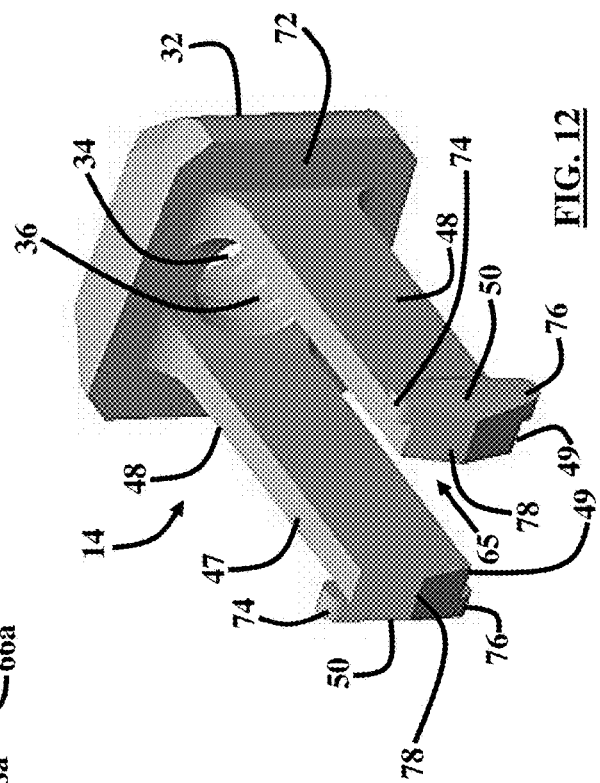
FIG. 10
FIG. 11
FIG. 12

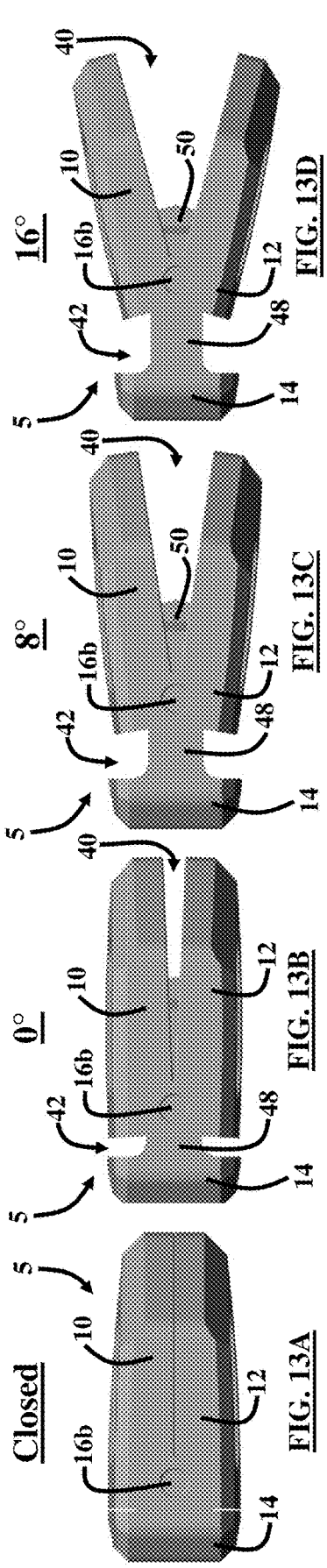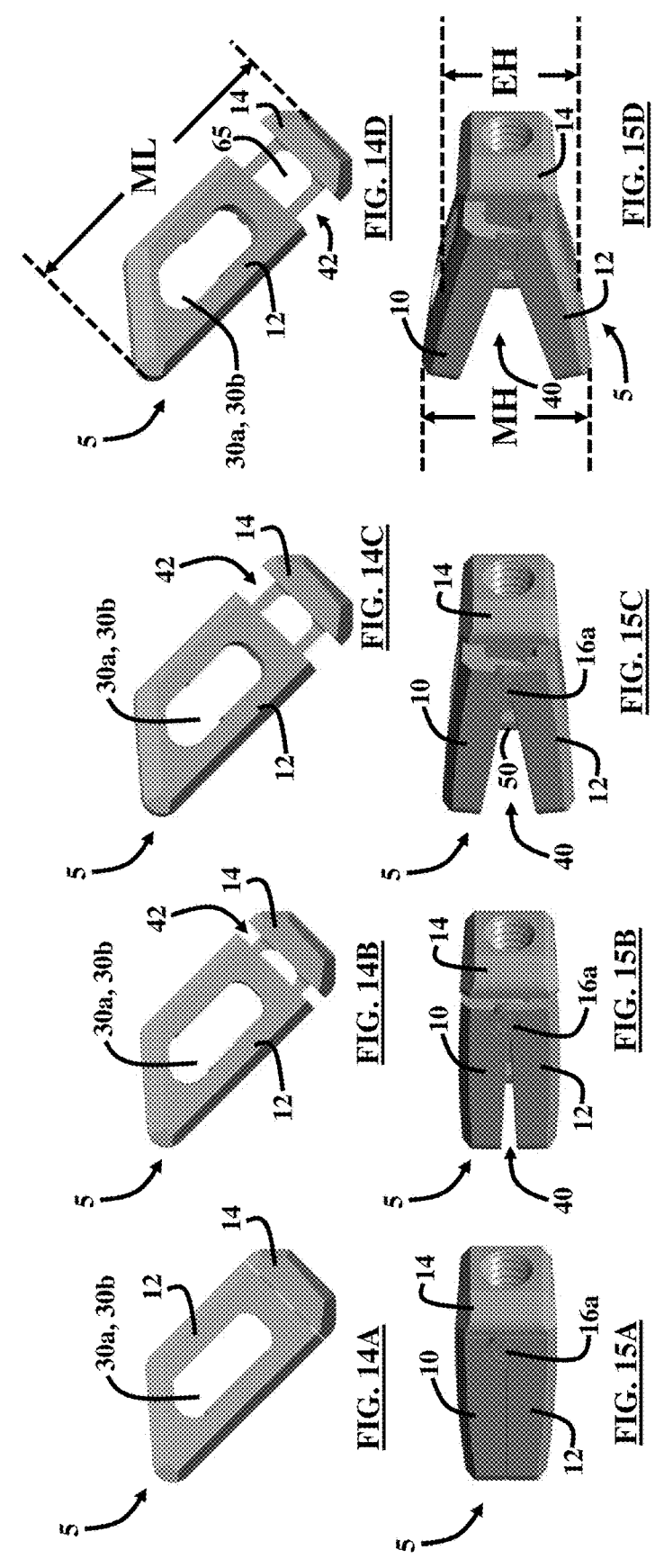

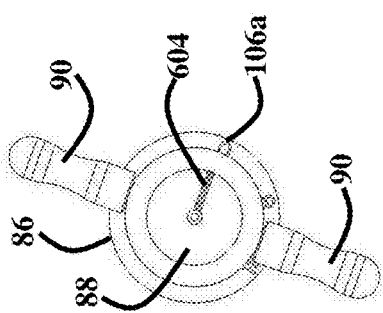
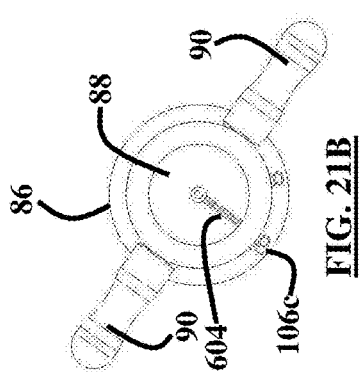
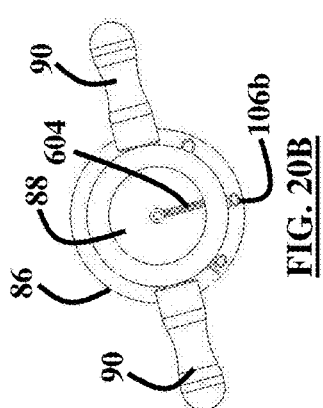
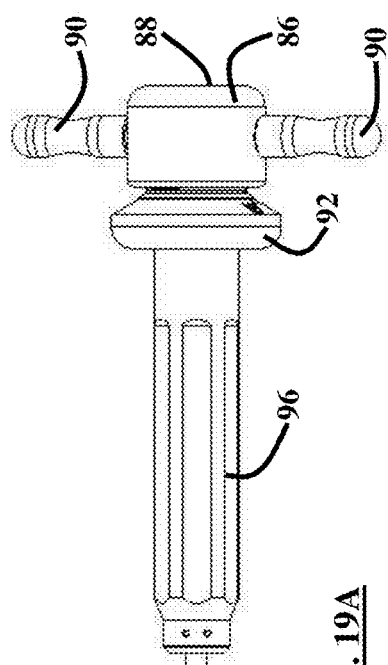
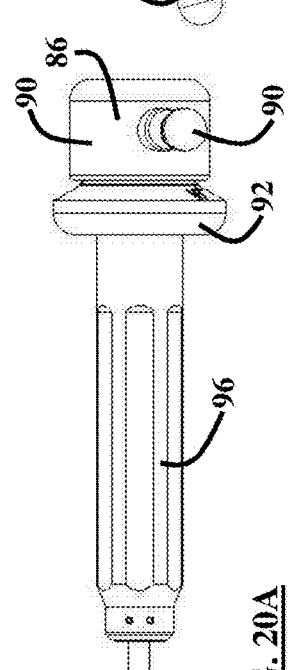
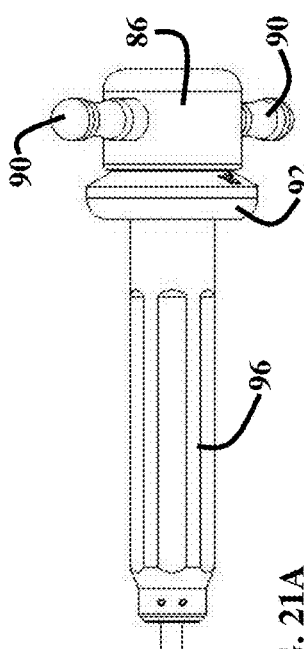
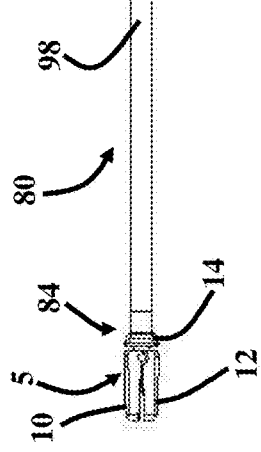
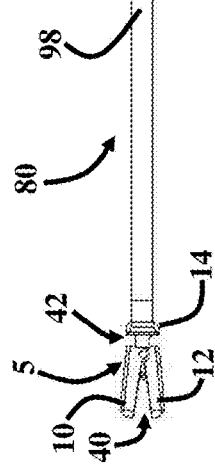
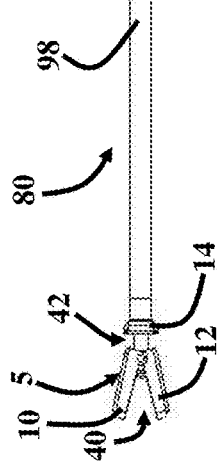

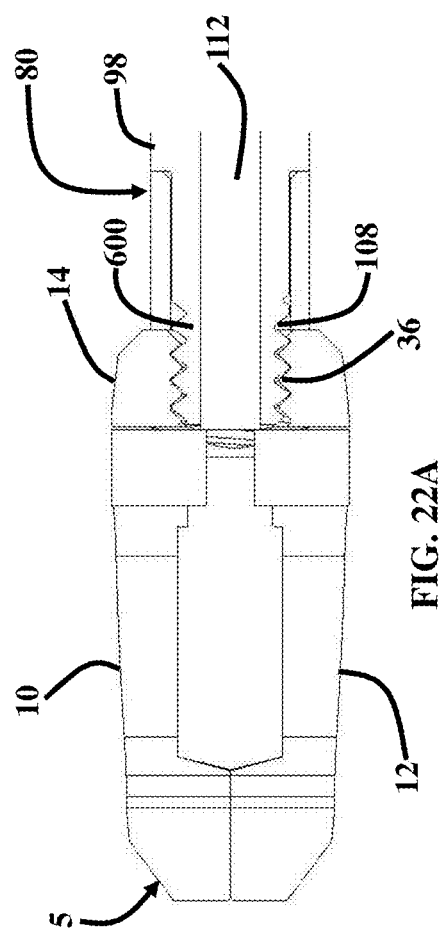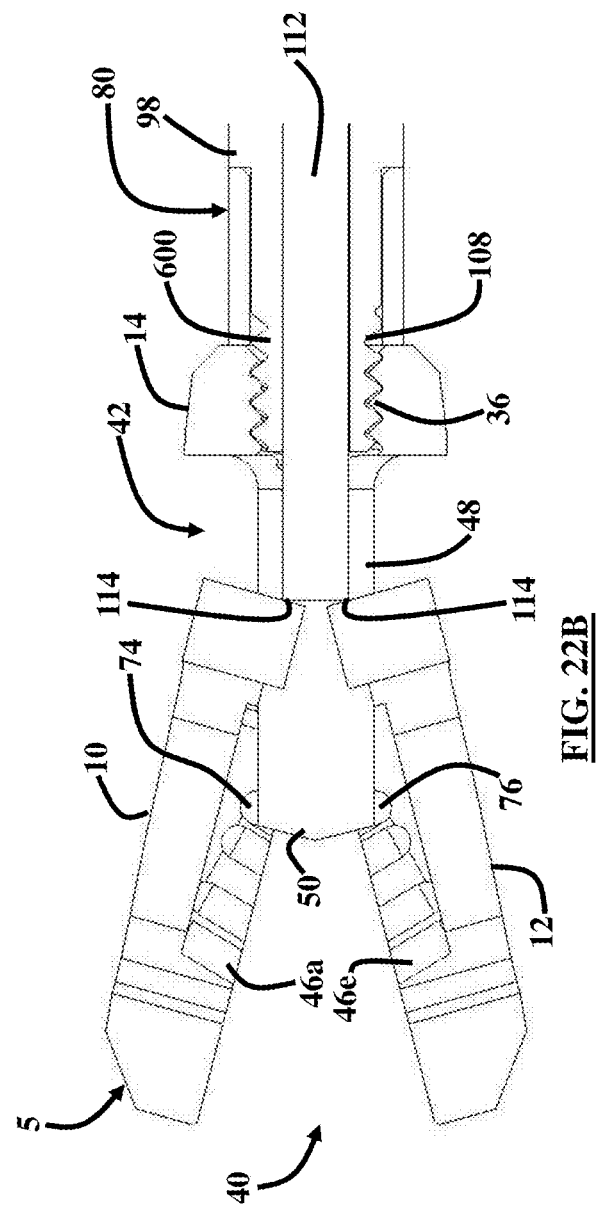

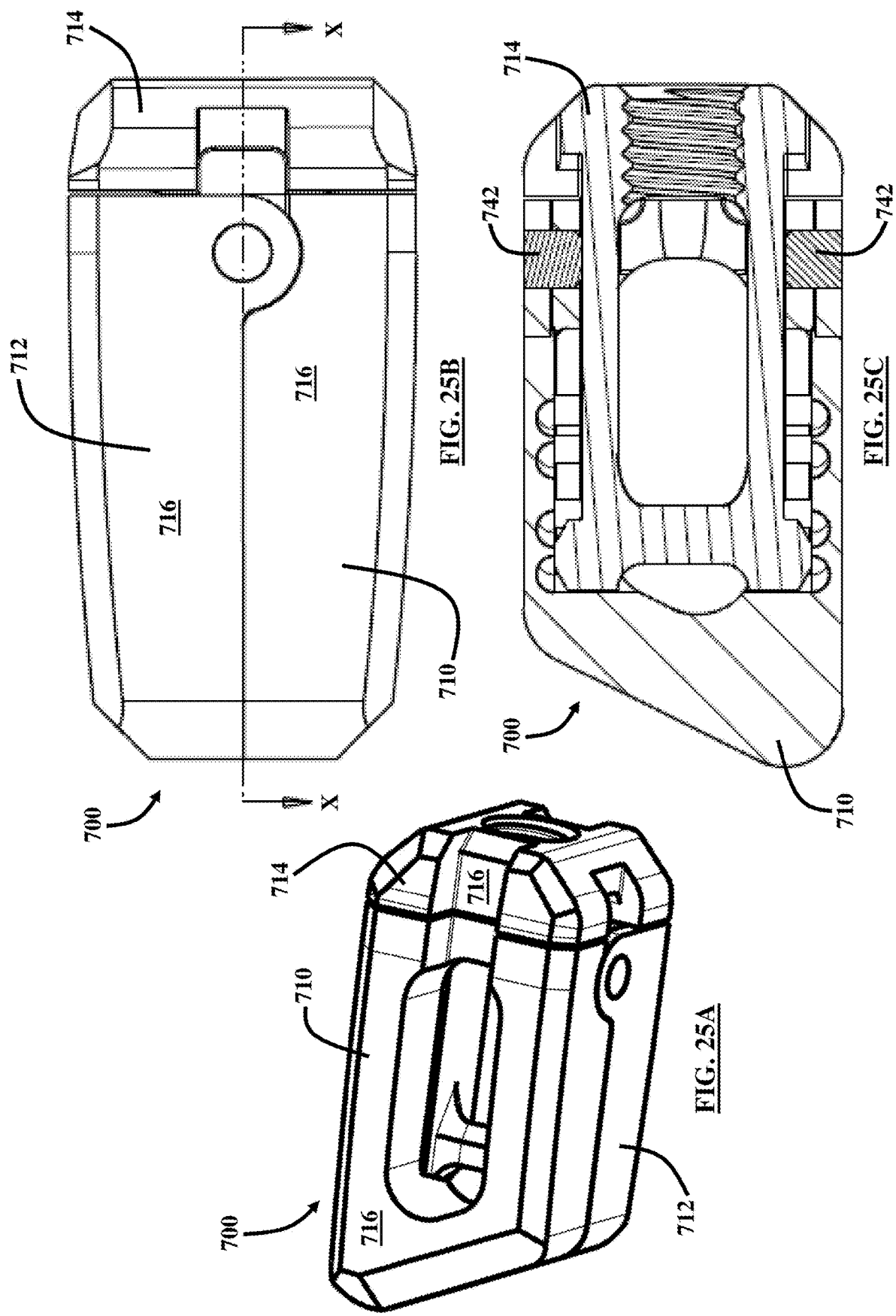

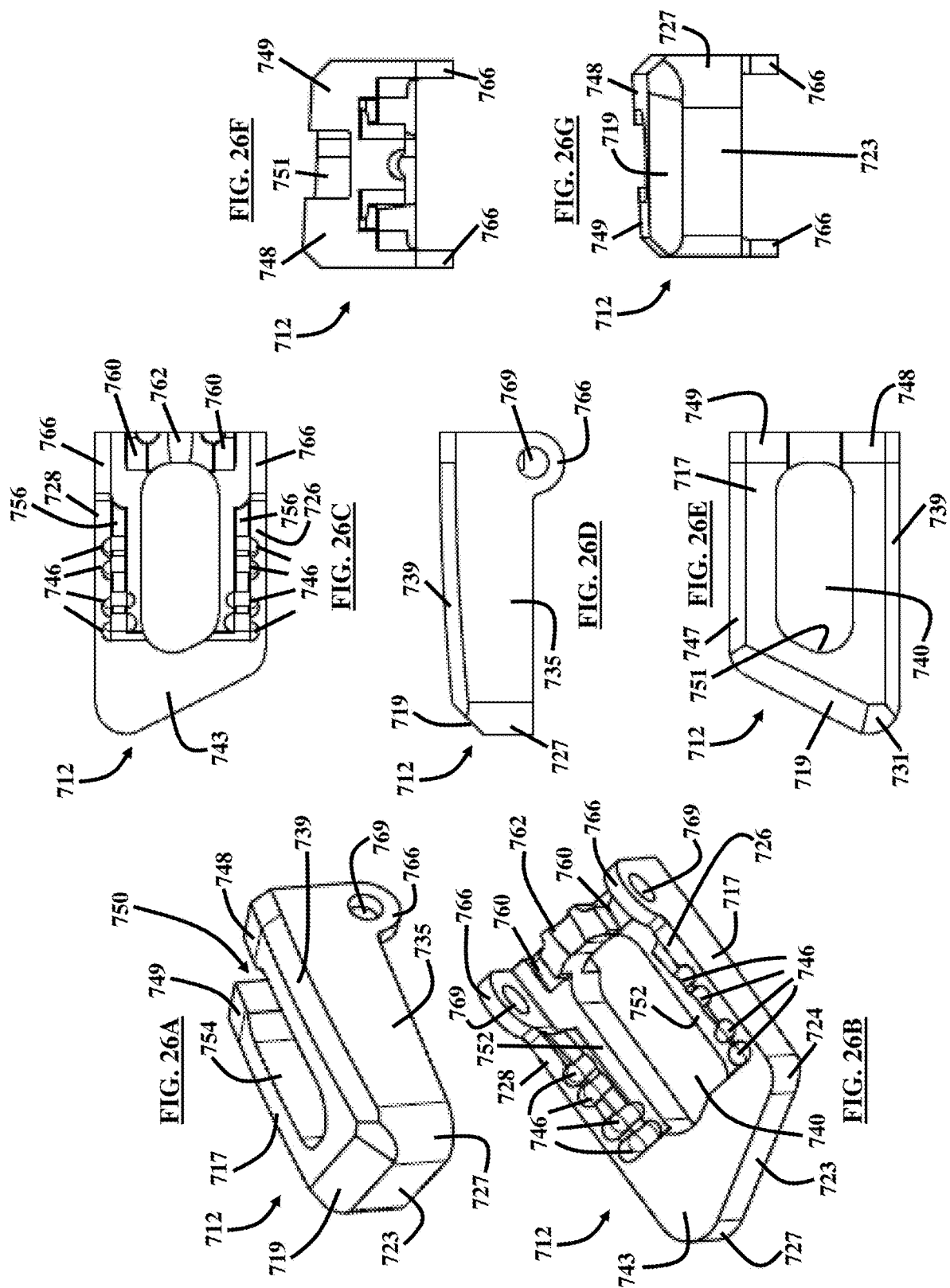

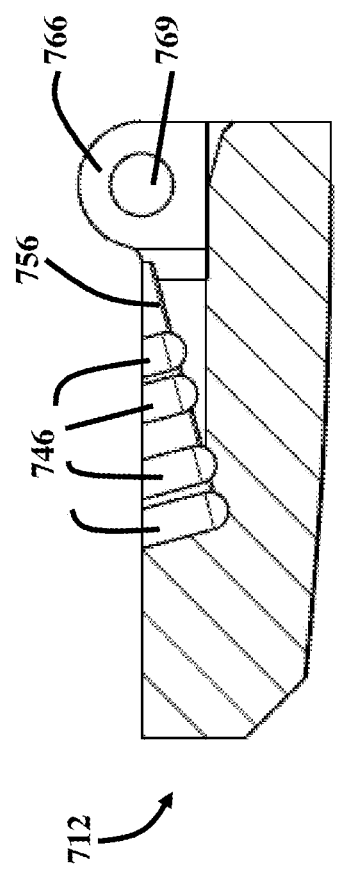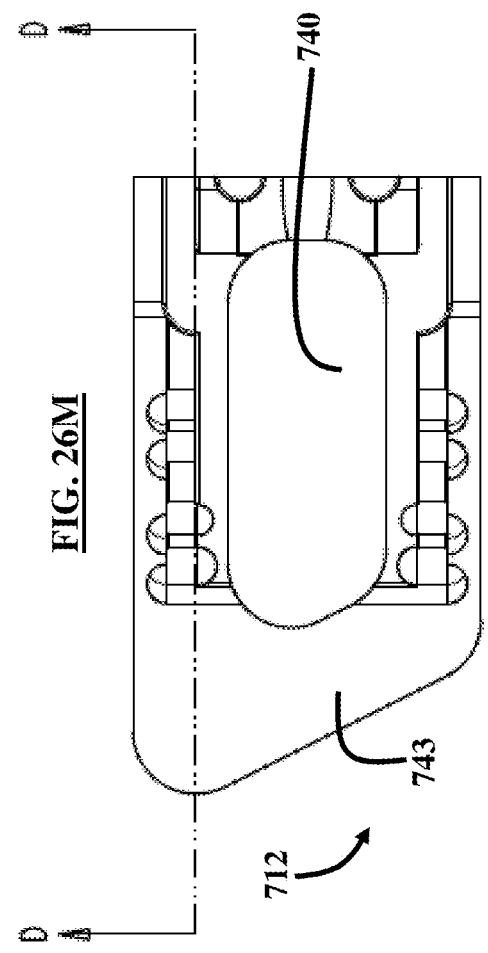

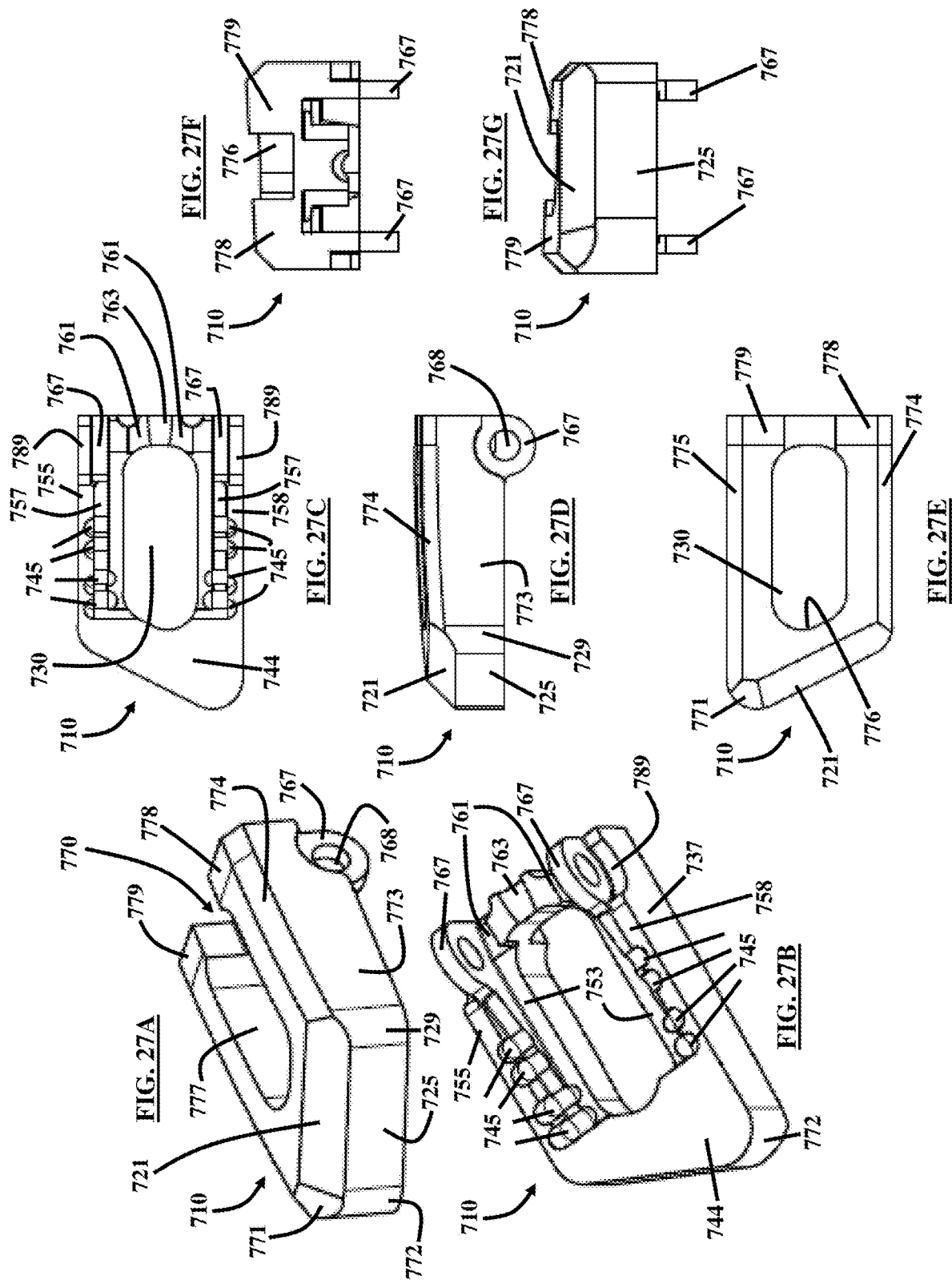

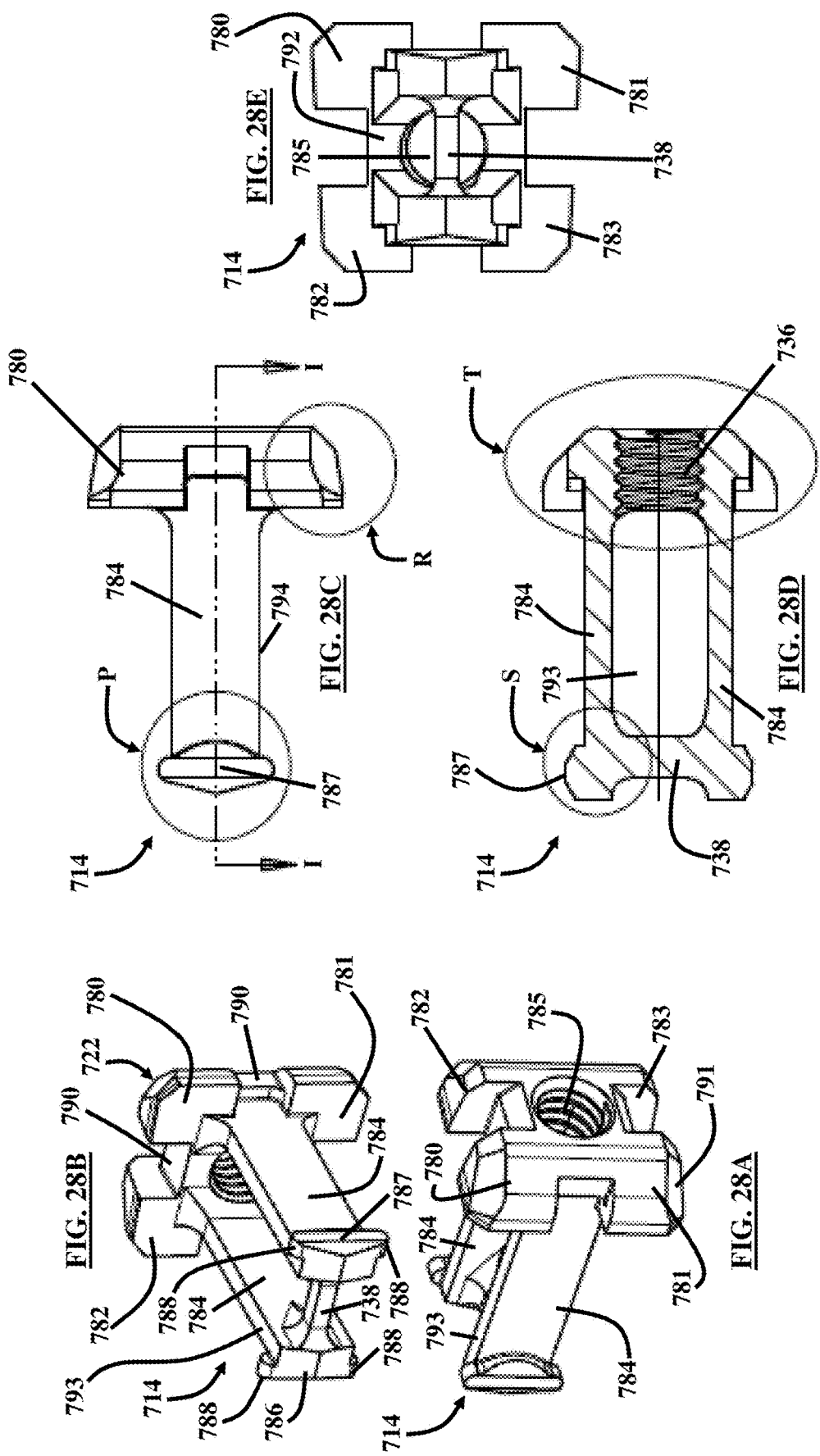

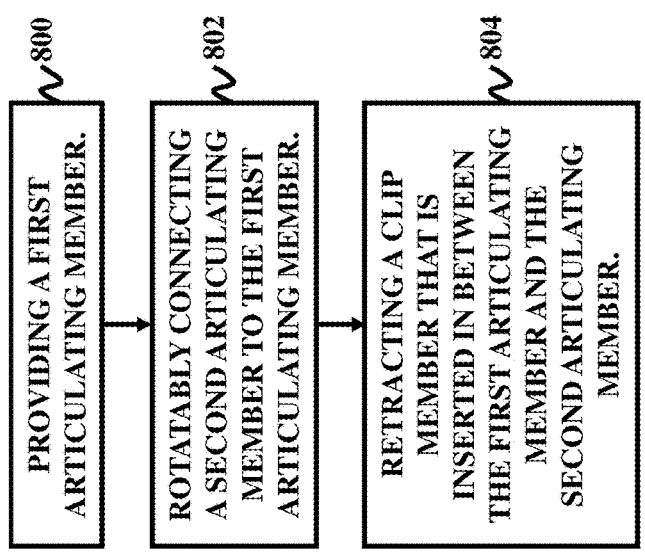
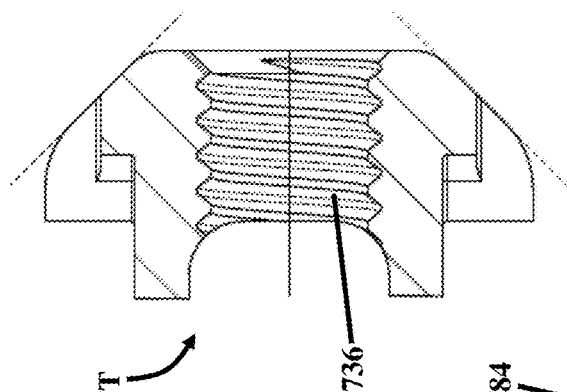
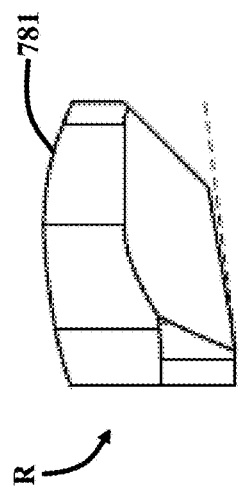
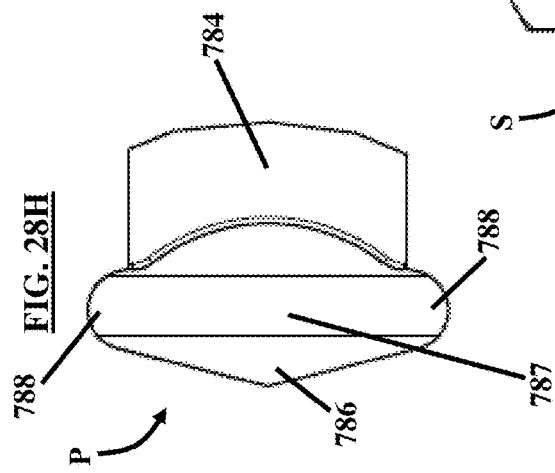
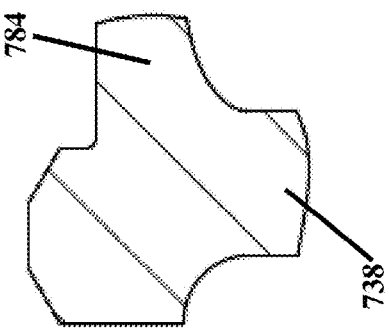

EXPANDABLE INTERBODY AND SYSTEM

CROSS-REFERENCE TO RELATED APPLICATIONS

This application claims priority to U.S. Provisional Patent Application Ser. No. 61/841,796 filed on Jul. 1, 2013 and entitled "Expanding Interbody" and U.S. Provisional Patent Application Ser. No. 61/884,966 filed on Sep. 30, 2013 and entitled "Expanding Interbody System," the complete disclosures of which, in their entireties, are hereby incorporated by reference.

BACKGROUND

Technical Field

The embodiments herein generally relate to medical devices, and more particularly to an interbody device to correct deformities in the human spine.

Description of the Related Art

Most of the conventional interbody products on the market use a threaded mechanism such as in U.S. Pat. No. 6,685,742, for example. Other conventional interbody products are unpackable devices that may spit out or require pre-packing the space with bone prior to insertion.

SUMMARY

In view of the foregoing, an embodiment herein provides a hinged spinal fusion cage that expands in front to achieve lordosis, yet is of a reasonable size, stability and is packable with bone and easy to insert. A spinal cage is provided with some limited spring action in an expanded state to avoid subsidence into bone. Another embodiment provides a hinged spinal fusion cage that expands in front to achieve lordosis, yet is of a reasonable size, stability and is packable with bone and easy to insert.

An embodiment herein provides an expanding interbody comprising a first articulating member; a second articulating member rotatably connected to the first articulating member; and a clip member that engages each of the first articulating member and the second articulating member, wherein any of the first articulating member and the second articulating member comprises a plurality of grooves arranged in a progressively elongated arrangement, and wherein the clip member comprises at least one protruding tip that sequentially engages the plurality of grooves causing the first articulating member to rotate with respect to the second articulating member. The rotation of the first articulating member with respect to the second articulating member preferably creates an angled opening between the first articulating member and the second articulating member. The clip member may comprise a head portion comprising a plurality of prongs, wherein a first pair of the plurality of prongs are dimensioned and configured to be larger than a second pair of the plurality of prongs; a threaded hole substantially positioned in a center of the head portion; and a pair of cantilever arms extending from the head portion and positioned on opposite sides of the threaded hole.

The pair of cantilever arms may comprise a cross bar connecting the pair of cantilever arms together, and wherein the pair of cantilever arms comprise the at least one protruding tip. The first articulating member and the second articulating member may be complimentarily dimensioned and configured to one another. Any of the first articulating member and the second articulating member may comprises a first sidewall having a first length; a second sidewall oppositely positioned from the first sidewall and having a second length smaller than the first length; a hole separating the first sidewall from the second sidewall; a pair of sockets comprising a hole; and the plurality of grooves configured in the first sidewall and the second sidewall. The plurality of grooves may comprise a spacer positioned in between a pair of grooves in the plurality of grooves. The first articulating member may comprise a first pair of sockets comprising a first pair of holes, and the second articulating member may comprise a second pair of sockets comprising a second pair of holes, wherein the holes of the first pair of sockets align with the holes of the second pair of sockets. The expanding interbody may further comprise at least one pin dimensioned and configured to engage the hole of the pair of sockets. Any of the first articulating member and the second articulating member may comprise a pair of walls connected to the pair of sockets, wherein the pair of walls are separated by a gap therebetween, wherein a first wall of the pair of walls may comprise a height greater than a height of a second wall of the pair of walls, and wherein a top of the pair of walls may be angled such that the top is not planar.

Another embodiment provides an expanding interbody comprising a first articulating member; a second articulating member rotatably connected to the first articulating member, wherein the first articulating member and the second articulating member are complimentarily dimensioned and configured to one another; and a clip member that engages each of the first articulating member and the second articulating member, wherein any of the first articulating member and the second articulating member comprises a plurality of interrupted grooves arranged in a progressively elongated arrangement, wherein the clip member comprises at least one protruding tip that sequentially engages the plurality of interrupted grooves upon extraction of the clip member from the first and second articulating members causing the first articulating member to rotate with respect to the second articulating member, and wherein rotation of the first articulating member with respect to the second articulating member creates an angled opening between the first articulating member and the second articulating member.

The clip member may comprise a plurality of prongs, wherein a first pair of the plurality of prongs are dimensioned and configured to be larger than a second pair of the plurality of prongs; a threaded hole substantially positioned in a center of the head portion; a pair of cantilever arms extending from the head portion and positioned on opposite sides of the threaded hole; and a cross bar connecting the pair of cantilever arms together, and wherein the pair of cantilever arms comprise the at least one protruding tip. Any of the first articulating member and the second articulating member may comprise a first sidewall having a first length; a second sidewall oppositely positioned from the first sidewall and having a second length smaller than the first length; a hole separating the first sidewall from the second sidewall; a pair of sockets comprising a hole; and the plurality of grooves configured in the first sidewall and the second sidewall. The expanding interbody may further comprise at least one pin, wherein the first articulating member may comprise a first pair of sockets comprising a first pair of holes, wherein the second articulating member may comprise a second pair of sockets comprising a second pair of holes, wherein the holes of the first pair of sockets may align with the holes of the second pair of sockets, and wherein the at least one pin may be dimensioned and configured to engage the hole of the pair of sockets. Any of the first articulating member and the second articulating member may comprise a pair of walls connected to the pair of sockets, wherein the pair of walls may be separated by a gap therebetween, wherein a first wall of the pair of walls may comprise a height greater than a height of a second wall of the pair of walls, and wherein a top of the pair of walls may be angled such that the top is not planar.

Another embodiment provides a method of expanding an interbody, the method comprising providing a first articulating member; rotatably connecting a second articulating member to the first articulating member, wherein any of the first articulating member and the second articulating member comprises a plurality of grooves arranged in a progressively elongated arrangement; and retracting a clip member that is inserted in between the first articulating member and the second articulating member, wherein the clip member comprises at least one protruding tip that sequentially engages the plurality of grooves causing the first articulating member to rotate with respect to the second articulating member. Rotation of the first articulating member with respect to the second articulating member may create an angled opening between the first articulating member and the second articulating member. The method may further comprise using an inserter device to extract the clip member from the first and second articulating members. The method may further comprise the clip member terminating extraction from the first and second articulating members upon the at least one protruding tip engaging a last groove of the plurality of grooves.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 6C illustrates another side view of the inserter device of FIG. 5 after engaging the interbody implant device of FIG. 1 according to an embodiment herein;

FIG. 6D illustrates a front view of the inserter device of FIG. 5 after engaging the interbody implant device of FIG. 1 according to an embodiment herein;

FIG. 7A illustrates a top view of an interbody implant device according to a second embodiment herein;

FIG. 7B illustrates a perspective view of the device of FIG. 7A according to a second embodiment herein;

FIG. 7C illustrates a perspective view of the device of FIG. 7A in an expanded position according to a second embodiment herein;

FIG. 8A illustrates an exploded view of an interbody implant device according to a third embodiment herein;

FIG. 8C illustrates a perspective view of the device of FIG. 8A in another position according to a third embodiment herein;

FIG. 9G illustrates a front perspective view of an expandable interbody device in a 16° open configuration according to a fourth embodiment herein;

FIG. 9H illustrates a rear perspective view of an expandable interbody device in a 16° open configuration according to a fourth embodiment herein;

FIG. 10 illustrates a perspective view of the first articulating member of the expandable interbody device of FIGS. 9A through 9H according to a fourth embodiment herein;

FIG. 11 illustrates a perspective view of the second articulating member of the expandable interbody device of FIGS. 9A through 9H according to a fourth embodiment herein;

FIG. 12 illustrates a perspective view of the clip member of the expandable interbody device of FIGS. 9A through 9H according to a fourth embodiment herein;

FIG. 13A illustrates a side view of the expandable interbody device of FIGS. 9A and 9B in a closed configuration according to a fourth embodiment herein;

FIG. 13B illustrates a side view of the expandable interbody device of FIGS. 9C and 9D in a 0° open configuration according to a fourth embodiment herein;

FIG. 13C illustrates a side view of the expandable interbody device of FIGS. 9E and 9F in a 8° open configuration according to a fourth embodiment herein;

FIG. 13D illustrates a side view of the expandable interbody device of FIGS. 9G and 9H in a 16° open configuration according to a fourth embodiment herein;

FIG. 14A illustrates a top view of the expandable interbody device of FIGS. 9A and 9B in a closed configuration according to a fourth embodiment herein;

FIG. 14B illustrates a top view of the expandable interbody device of FIGS. 9C and 9D in a 0° open configuration according to a fourth embodiment herein;

FIG. 14C illustrates a top view of the expandable interbody device of FIGS. 9E and 9F in a 8° open configuration according to a fourth embodiment herein;

FIG. 14D illustrates a top view of the expandable interbody device of FIGS. 9G and 9H in a 16° open configuration according to a fourth embodiment herein;

FIG. 15A illustrates a rear perspective view of the expandable interbody device of FIGS. 9A and 9B in a closed configuration according to a fourth embodiment herein;

FIG. 15B illustrates a rear perspective view of the expandable interbody device of FIGS. 9C and 9D in a 0° open configuration according to a fourth embodiment herein;

FIG. 15C illustrates a rear perspective view of the expandable interbody device of FIGS. 9E and 9F in a 8° open configuration according to a fourth embodiment herein;

FIG. 15D illustrates a rear perspective view of the expandable interbody device of FIGS. 9G and 9H in a 16° open configuration according to a fourth embodiment herein;

FIG. 19A illustrates a side view of an inserter device engaging the expandable interbody device of FIGS. 9C through 9D according to a fourth embodiment herein;

FIG. 19B illustrates an end view of the inserter device of FIG. 19A according to a fourth embodiment herein;

FIG. 20A illustrates a side view of an inserter device engaging the expandable interbody device of FIGS. 9E through 9F according to a fourth embodiment herein;

FIG. 20B illustrates an end view of the inserter device of FIG. 20A according to a fourth embodiment herein;

FIG. 21A illustrates a side view of an inserter device engaging the expandable interbody device of FIGS. 9G through 9H according to a fourth embodiment herein;

FIG. 21B illustrates an end view of the inserter device of FIG. 21A according to a fourth embodiment herein;

FIG. 22A illustrates a magnified cross-sectional view of the expandable interbody device being engaged by the inserter device of FIG. 21A according to a fourth embodiment herein;

FIG. 22B illustrates a magnified cross-sectional view of the expandable interbody device being engaged by the inserter device of FIG. 21A according to a fourth embodiment herein;

FIG. 25A illustrates a perspective view of an expandable interbody device according to a sixth embodiment herein;

FIG. 25B illustrates a side view of the expandable interbody device of FIG. 25A according to a sixth embodiment herein;

FIG. 25C illustrates a cross-sectional view cut along line X-X of the expandable interbody device of FIG. 25B according to a sixth embodiment herein;

FIG. 26A illustrates a top perspective view of the second articulating member of the expandable interbody device of FIGS. 25A through 25B according to a sixth embodiment herein;

FIG. 26B illustrates a bottom perspective view of the second articulating member of the expandable interbody device of FIGS. 25A through 25B according to a sixth embodiment herein;

FIG. 26C illustrates a bottom plan view of the second articulating member of FIG. 26B of the expandable interbody device of FIGS. 25A through 25B according to a sixth embodiment herein;

FIG. 26D illustrates a side view of the second articulating member of the expandable interbody device of FIGS. 25A through 25B according to a sixth embodiment herein;

FIG. 26E illustrates a top plan view of the second articulating member of FIG. 26A of the expandable interbody device of FIGS. 25A through 25B according to a sixth embodiment herein;

FIG. 26F illustrates a rear plan view of the second articulating member of FIG. 26A of the expandable interbody device of FIGS. 25A through 25B according to a sixth embodiment herein;

FIG. 26G illustrates a front plan view of the second articulating member of FIG. 26A of the expandable interbody device of FIGS. 25A through 25B according to a sixth embodiment herein;

FIG. 26M illustrates another magnified bottom plan view of the second articulating member of FIG. 26B of the expandable interbody device of FIGS. 25A through 25B according to a sixth embodiment herein;

FIG. 26N illustrates a cross-sectional view cut along line D-D of the expandable interbody device of FIG. 26M according to a sixth embodiment herein;

FIG. 27A illustrates a top perspective view of the first articulating member of the expandable interbody device of FIGS. 25A through 25B according to a sixth embodiment herein;

FIG. 27B illustrates a bottom perspective view of the first articulating member of the expandable interbody device of FIGS. 25A through 25B according to a sixth embodiment herein;

FIG. 27C illustrates a bottom plan view of the first articulating member of FIG. 27B of the expandable interbody device of FIGS. 25A through 25B according to a sixth embodiment herein;

FIG. 27D illustrates a side view of the first articulating member of the expandable interbody device of FIGS. 25A through 25B according to a sixth embodiment herein;

FIG. 27E illustrates a top plan view of the first articulating member of FIG. 27A of the expandable interbody device of FIGS. 25A through 25B according to a sixth embodiment herein;

FIG. 27F illustrates a rear plan view of the first articulating member of FIG. 27A of the expandable interbody device of FIGS. 25A through 25B according to a sixth embodiment herein;

FIG. 27G illustrates a front plan view of the first articulating member of FIG. 27A of the expandable interbody device of FIGS. 25A through 25B according to a sixth embodiment herein;

FIG. 28A illustrates a front perspective view of the clip member of the expandable interbody device of FIGS. 25A through 25C according to a sixth embodiment herein;

FIG. 28B illustrates a rear perspective view of the clip member of the expandable interbody device of FIGS. 25A through 25C according to a sixth embodiment herein;

FIG. 28C illustrates a side view of the clip member of FIGS. 28A through 28B according to a sixth embodiment herein;

FIG. 28D illustrates a cross-sectional view cut along line I-I of the clip member of FIG. 28C according to a sixth embodiment herein;

FIG. 28E illustrates a front plan view of the clip member of FIG. 28B according to a sixth embodiment herein;

FIG. 28H illustrates an isolated magnified view of the encircled area P of the clip member of FIG. 28C according to a sixth embodiment herein;

FIG. 28I illustrates an isolated magnified view of the encircled area R of the clip member of FIG. 28C according to a sixth embodiment herein;

FIG. 28J illustrates an isolated magnified view of the encircled area S of the clip member of FIG. 28D according to a sixth embodiment herein;

FIG. 28K illustrates an isolated magnified view of the encircled area T of the clip member of FIG. 28D according to a sixth embodiment herein; and FIG. 29 is a flowchart illustrating a method according to an embodiment herein.

DETAILED DESCRIPTION

Figure 1:
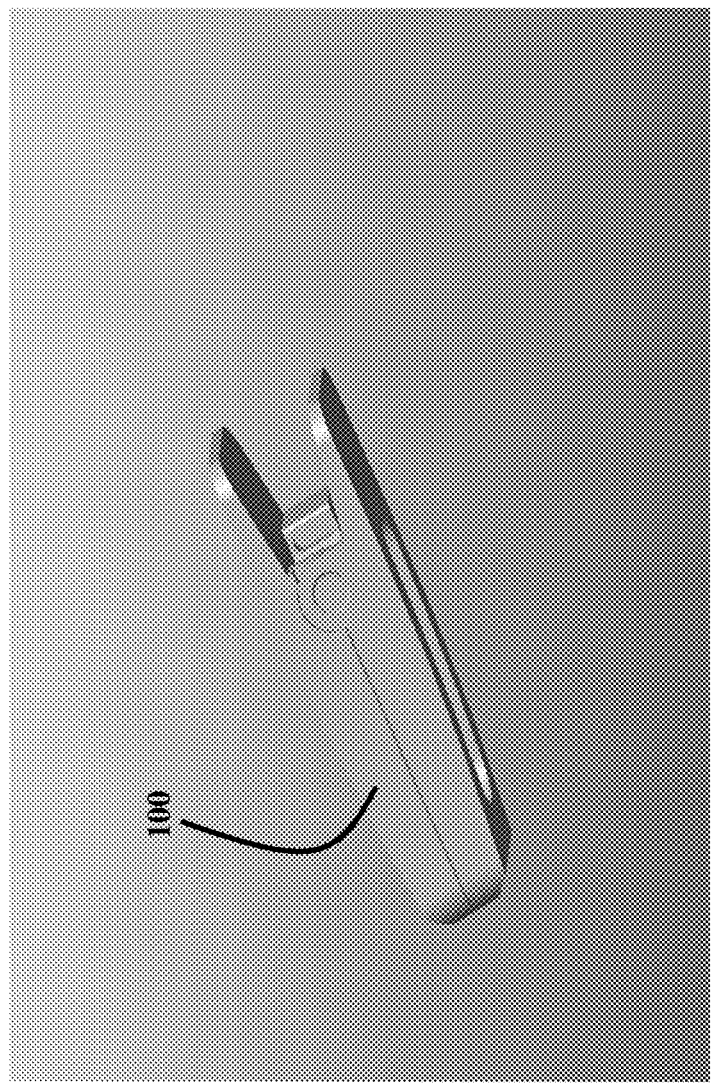
FIG. 1 illustrates a perspective view of an interbody implant device according to a first embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an interbody device. It may be used as a tlif, plif, alif, or lateral to correct various deformities in the human spine. It is an improvement in design over the conventional devices. The embodiments herein also provide an interbody system comprising an expandable interbody device and inserter device. In one embodiment, the interbody device has a beveled nose with an oblique upper and lower surface contours to better match endplate anatomy. Moreover, in one embodiment, the articulation positions of the interbody device are prescribed for 0°, 8°, and 16° openings (e.g., expansion) along with its closed initial state. Referring now to the drawings, and more particularly to FIGS. 1 through 29, where similar reference characters denote corresponding features consistently throughout the figures, there are shown preferred embodiments. The various figures and/or descriptions below indicate example dimensions and configurations. However, these dimensions and configurations are merely examples and the embodiments herein are not restricted to a particular dimension and/or configuration.

Figures 2A, 2B, 2C:
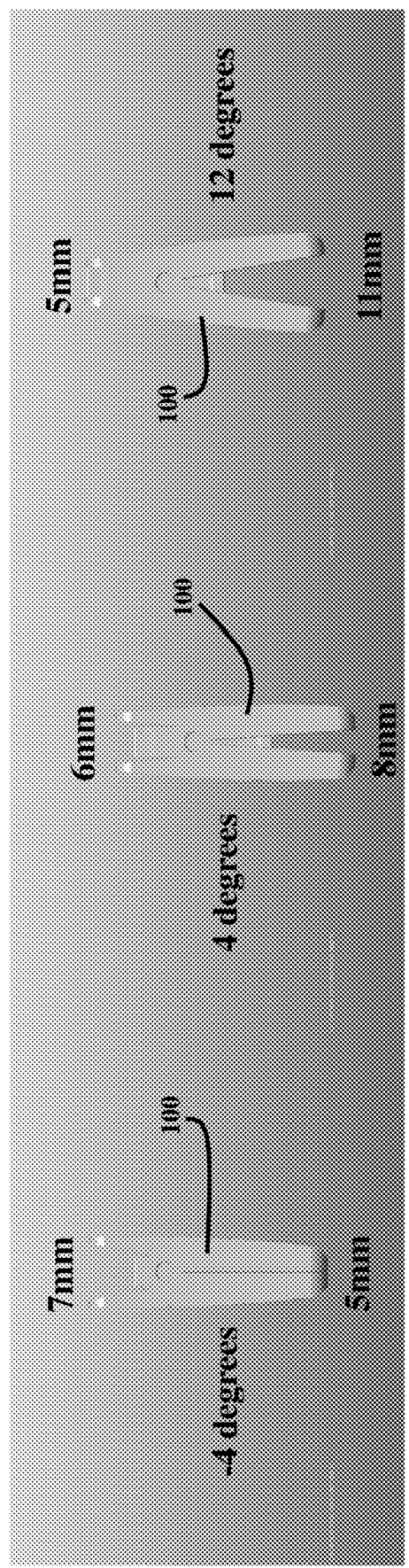
FIG. 2A illustrates the interbody implant device of FIG. 1 at insertion (e.g., initial position) according to a first embodiment herein.
FIG. 2B illustrates the interbody implant device of FIG. 1 after three clicks according to a first embodiment herein.
FIG. 2C illustrates the interbody implant device of FIG. 1 after five clicks, in its final position, according to a first embodiment herein.

FIG. 1 illustrates a perspective view of an interbody implant device 100 according to a first embodiment herein. In an example embodiment, the device 100 is approximately 7 mm in size and measure 4.5 mm on the front and 7 mm on the back×11×28 (although other configurations are possible). The window is approximately 5×16 mm therethrough, in one example embodiment (although other configurations are possible). FIG. 2A illustrates the device 100 of FIG. 1 at insertion (e.g., initial position), FIG. 2B illustrates the device 100 of FIG. 1 after three clicks, and FIG. 2C illustrates the device 100 of FIG. 1 after five clicks, in its final position.

Figure 3A:
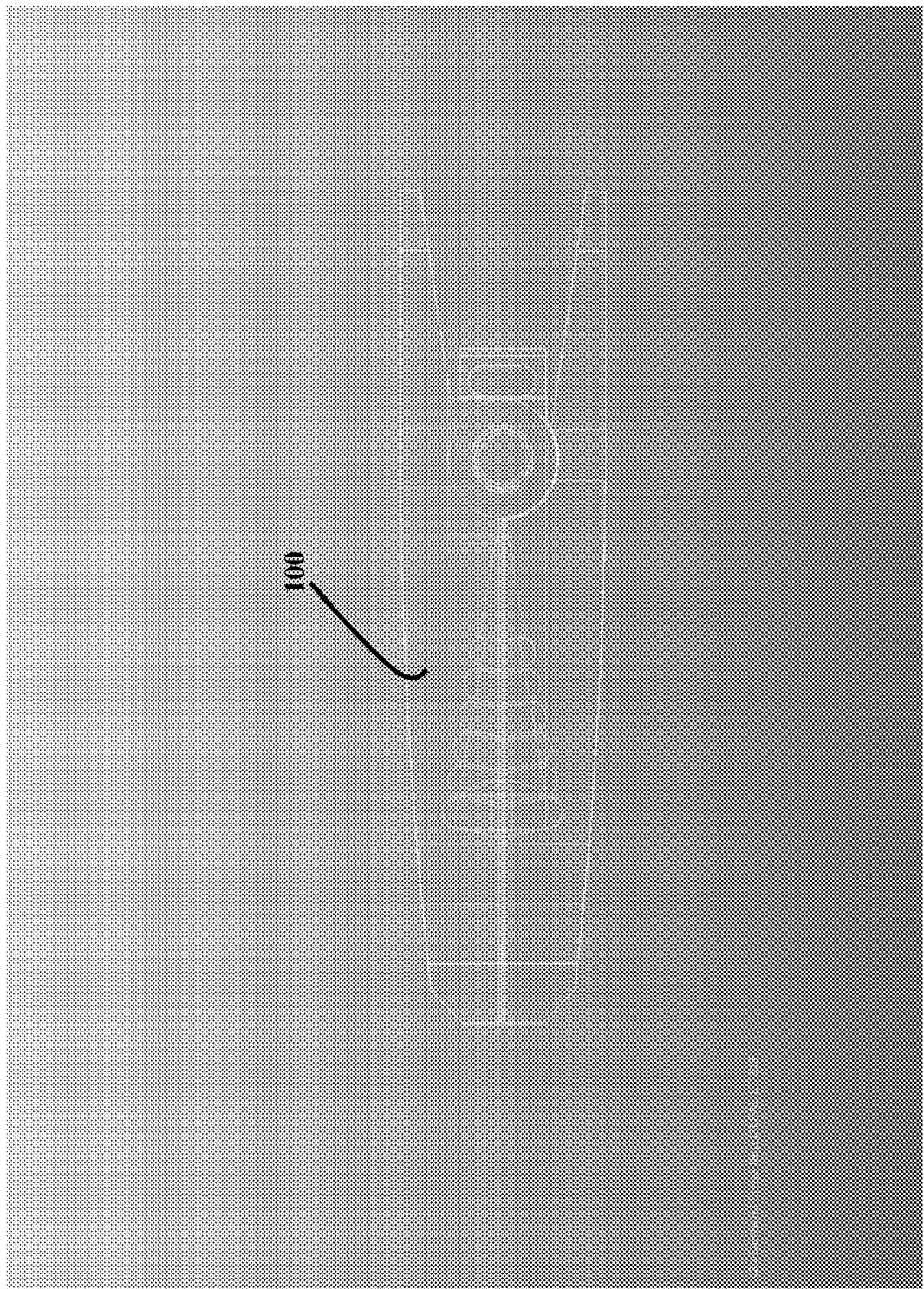
FIG. 3A illustrates a cross-sectional view of the interbody implant device of FIG. 2A according to a first embodiment herein.
Figure 3B:
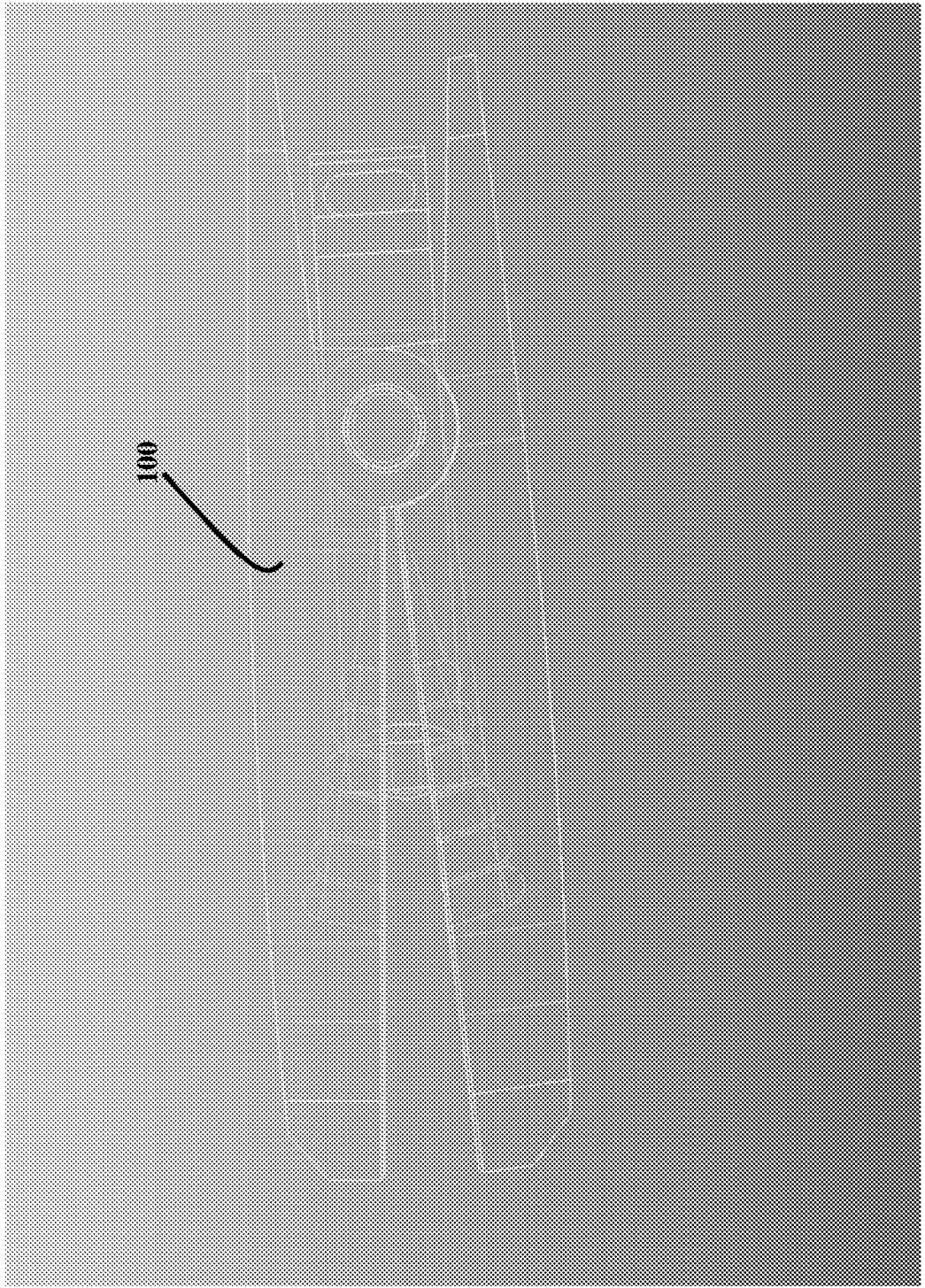
FIG. 3B illustrates a cross-sectional view of the interbody implant device of FIG. 2B according to a first embodiment herein.
Figure 3C:
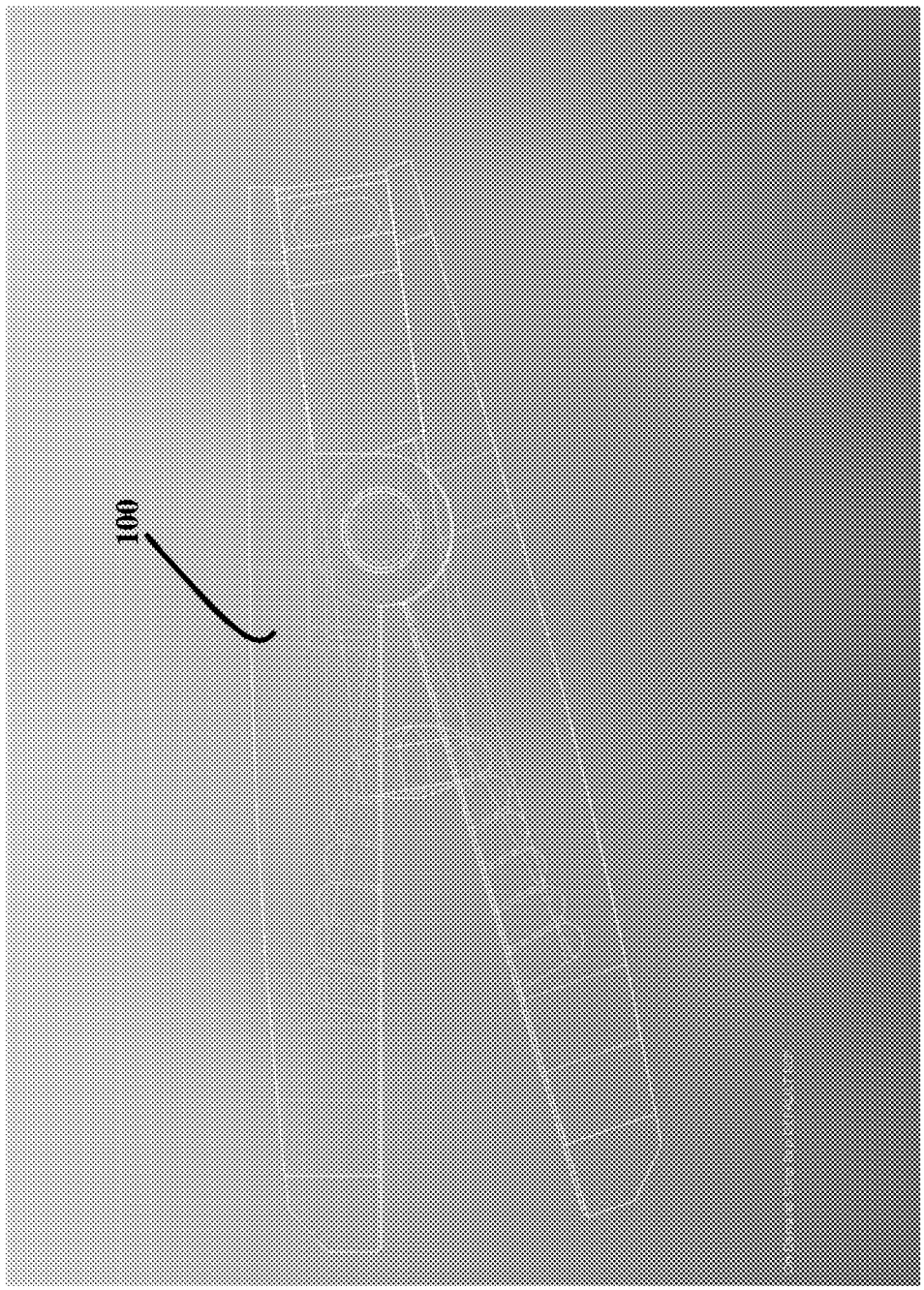
FIG. 3C illustrates a cross-sectional view of the interbody implant device of FIG. 2C according to a first embodiment herein.

FIGS. 3A through 3C, with reference to FIGS. 1 through 2C, illustrate cross-sectional views of the device 100. More specifically, FIG. 3A illustrates a cross-sectional view of the device 100 of FIG. 2A in its initial position. FIG. 3B illustrates a cross-sectional view of the device 100 of FIG. 2B after three clicks. FIG. 3C illustrates a cross-sectional view of the device 100 of FIG. 2C after five clicks, in its final position.

Figure 4A:
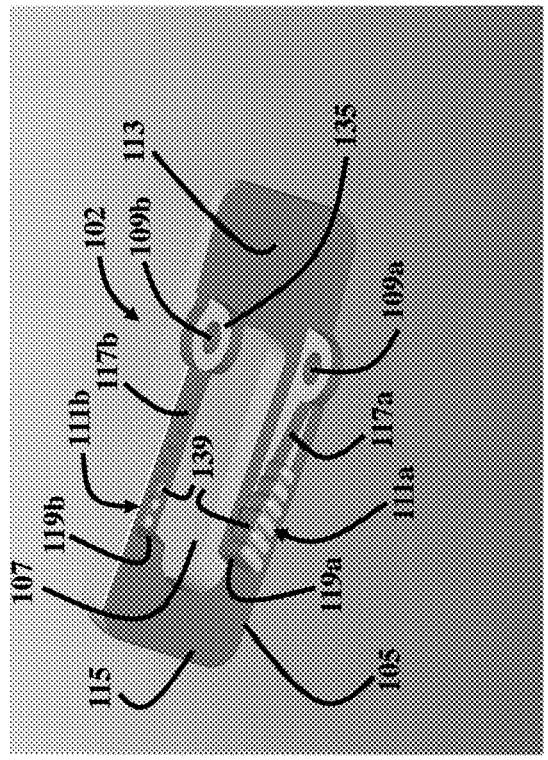
FIG. 4A illustrates a perspective view of a first clip component of the interbody implant device of FIG. 1 according to a first embodiment herein.
Figure 4B:
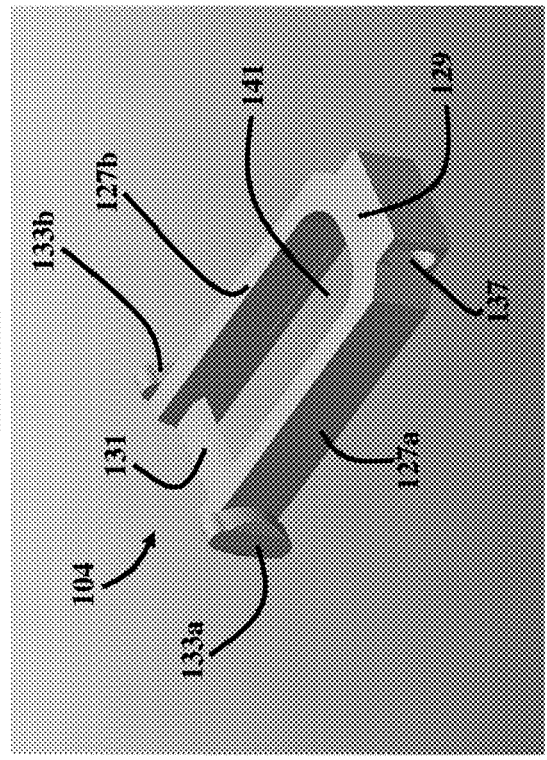
FIG. 4B illustrates a perspective view of a second clip component of the interbody implant device of FIG. 1 according to a first embodiment herein.
Figure 4C:
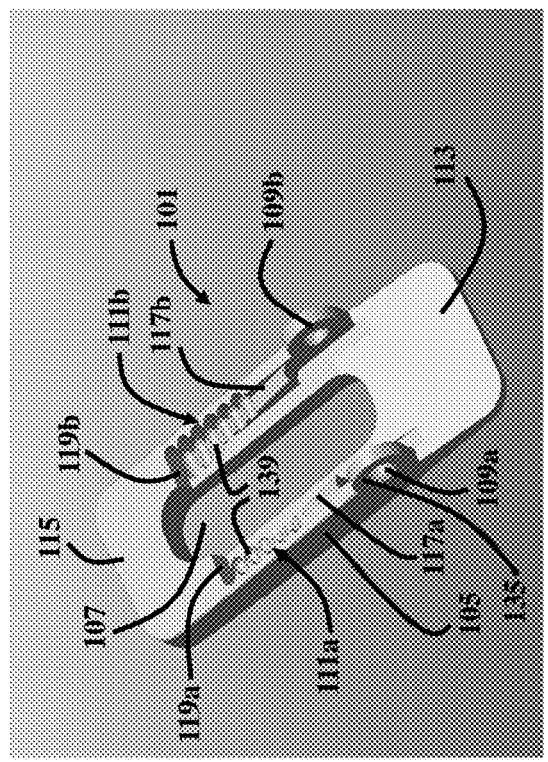
FIG. 4C illustrates a perspective view of a hinge pin of the interbody implant device of FIG. 1 according to a first embodiment herein.
Figure 4D:
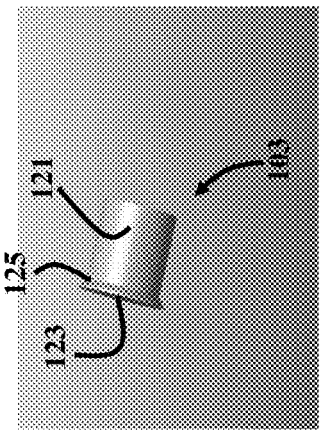
FIG. 4D illustrates a perspective view of an actuating clip of the interbody implant device of FIG. 1 according to a first embodiment herein.

As further shown in FIGS. 4A through 4D, with reference to FIGS. 1 through 3C, the device 100 comprises a first clip component 101 (FIG. 4A), a second clip component 102 (FIG. 4B), a pair of hinge pins 103 (only one hinge pin 103 is shown in FIG. 4C), and an actuating clip 104 (FIG. 4D). The first and second clip components 101, 102 are preferably similarly configured and comprise a body portion 105 having a window 107 disposed therethrough. A pair of aligned sockets 109a, 109b are configured on the body portion 105. A groove portion 111a, 111b is formed in recess of the body portion 105 and are positioned on opposite sides of the window 107. The body portion 105 comprises a slightly sloping first end 113 and an opposed generally non-sloping second end 115. A sloping ramp 117a, 117b extends between the sockets 109a, 109b to the groove portion 111a, 111b. The groove portion 111a, 111b comprises a plurality of progressively elongated grooves 139 that correspond with the "clicks" for the various stages of opening/engagement of the device 100. A back wall 119a, 119b is configured at the end of the groove portion 111a, 111b.

The hinge pin 103 comprises a substantially cylindrical body 121 and a base 123 having a diameter slightly larger than the diameter of the body 121. The base 123 may be slightly angled at the point of connection 125 with the body 121. The actuating clip 104 is configured to fit against the respective body portion 105 of the first and second clip components 101, 102 when assembled such that the actuating clip 104 fits in between the width defined between the sockets 109a, 109b. The actuating clip 104 comprises a pair of arms 127a, 127b connected by a first connection bar 129 and an opposed second connection bar 131. The second connection bar 131 includes a pair of flanges 133a, 133b positioned on the outside of the pair of arms 127a, 127b. The flanges 133a, 133b are configured to engage the groove portion 111a, 111b of the first and second clip components 101, 102 such that as the flanges 133a, 133b are pushed along the groove portion 111a, 111b into the plurality of grooves 139, the "clicks" occur and the first and second clip components 101, 102 are pivotally opened/expanded with respect to one another.

The hinge pins 103 provide the means for pivoting the first and second clip components 101, 102 with respect to one another. The body 121 of the hinge pins 103 is inserted into the sockets 109a, 109b such that the base 123 rests against the outer surface 135 of the sockets 109a, 109b. The hinge pins 103 may slightly rest against the actuating clip 104 in one embodiment. In an alternative embodiment, the hinge pins 103 do not touch the actuating clip 104 at all. The actuating clip 104 stays locked into the first and second clip components 101, 102 as it is pushed towards the groove portion 111a, 111b such that the flanges 133a, 133b engage the grooves 139 until the final position (e.g., adjacent to the back wall 119a, 119b of the first and second clip components 101, 102). In another embodiment, the pair of arms 127a, 127b comprise a channel (not shown) that permit the hinge pins 103 to slide therein while the actuating clip 104 slides or is pushed towards the groove portion 111a, 111b. The first connection bar 129 comprises a hole 137 extending at least partially through the width of the first connection bar 129 in one embodiment, and extending all the way through the width of the first connection bar 129 in another embodiment.

Figure 5:
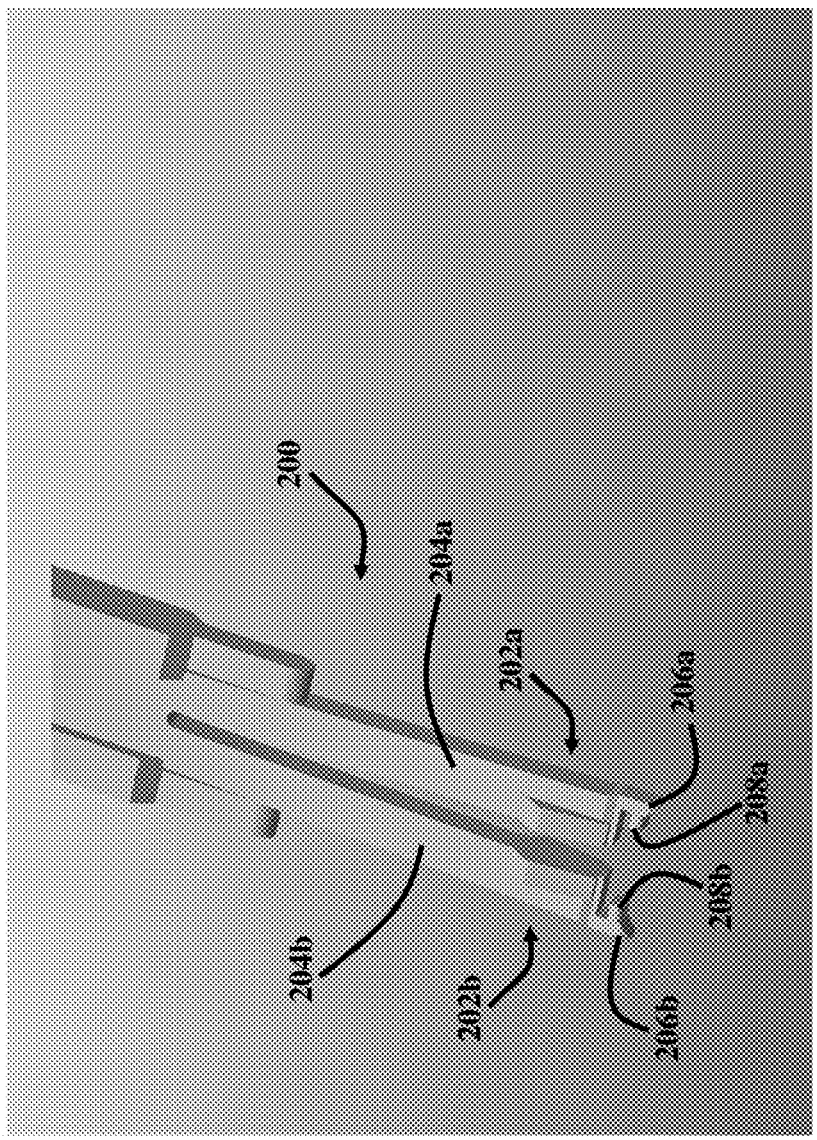
FIG. 5 illustrates a partial view of an inserter device according to an embodiment herein.

The device 100 may be implantable using an inserter 200, as partially shown in FIG. 5, with reference to FIGS. 1 through 4D. The inserter 200 may measure 6×11 mm (or other suitable configurations), for example, and has two main proximal components 202a, 202b to engage the device 100. The components 202a, 202b comprise a pair of arms 204a, 204b, which terminate with pincers 206a 206b comprising prongs 208a, 208b, which are configured to engage the hole 137 of the first connection bar 129 of the actuating clip 104 of FIG. 4D. Once the prongs 208a, 208b engage the hole 137 of the actuating clip 104, then the inserter 200 may push the actuating clip 104 down the sloping ramp 117a, 117b and into the groove portion 111a, 111b into the grooves 139 and into the final position adjacent to the back wall 119a, 119b of the first and second clip components 101, 102. The actuating clip 104 further includes a window 141, which may substantially align with window 107 of the first and second clip components 101, 102.

Figure 6A:
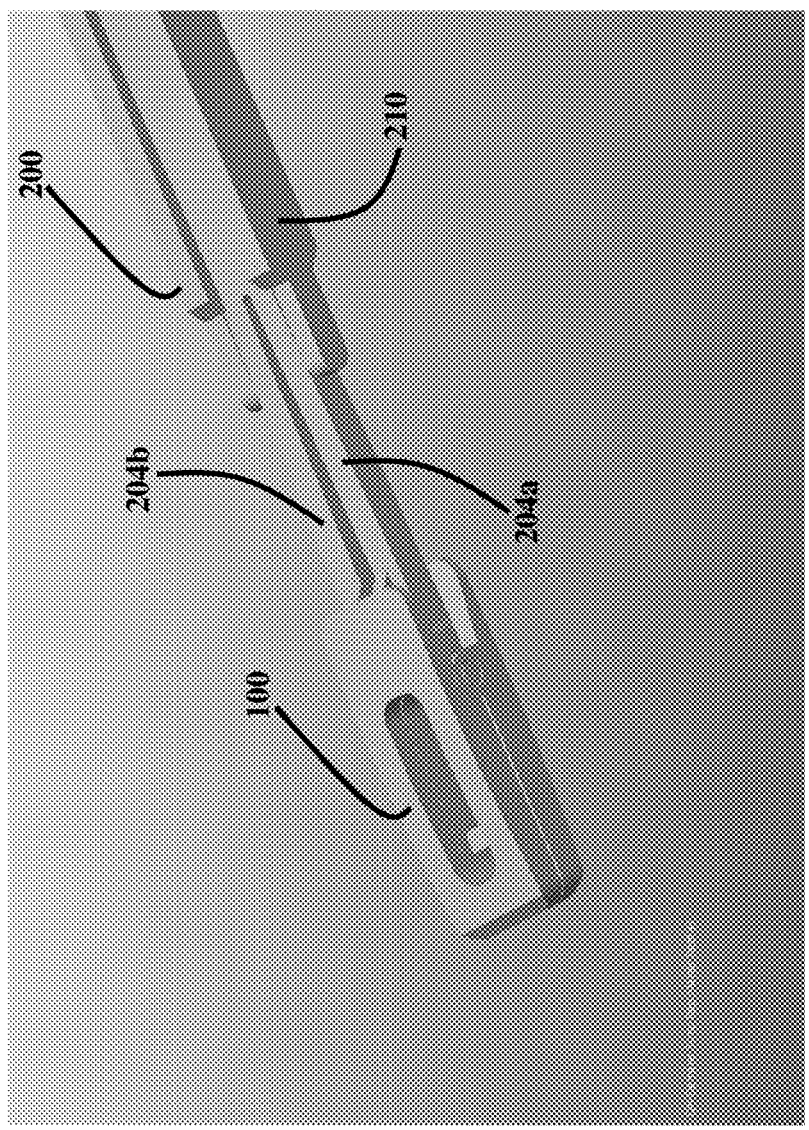
FIG. 6A illustrates the inserter device of FIG. 5 initially engaging the device of FIG. 1 according to an embodiment herein.
Figure 6B:
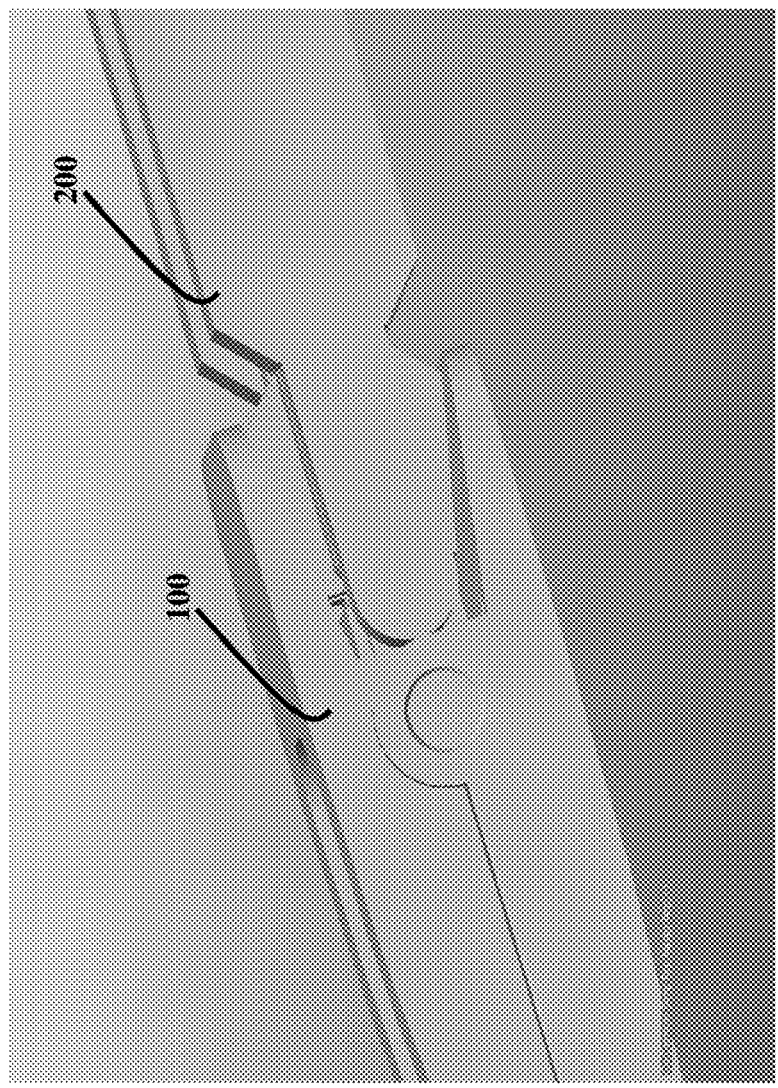
FIG. 6B illustrates a side view of the inserter device of FIG. 5 after engaging the interbody implant device of FIG. 1 according to an embodiment herein.
Figure 6E:
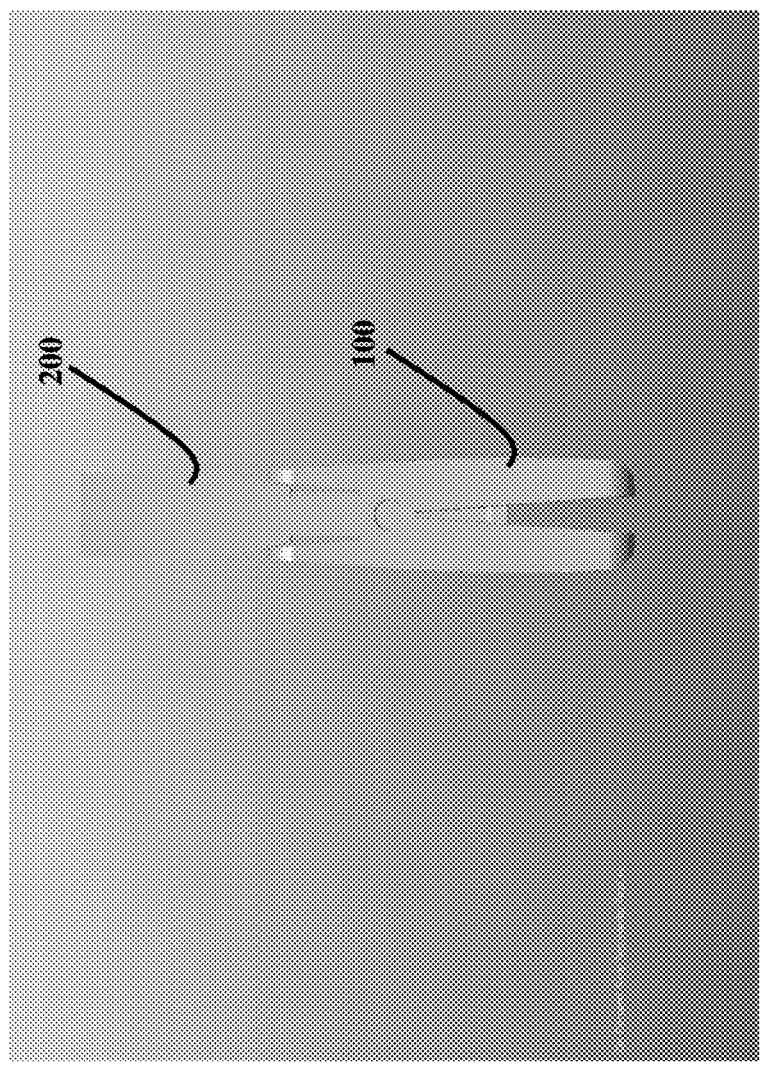
FIG. 6E illustrates a side view of the inserter device of FIG. 5 after engaging and implanting the interbody implant device of FIG. 1 with three clicks according to an embodiment herein.
Figure 6F:
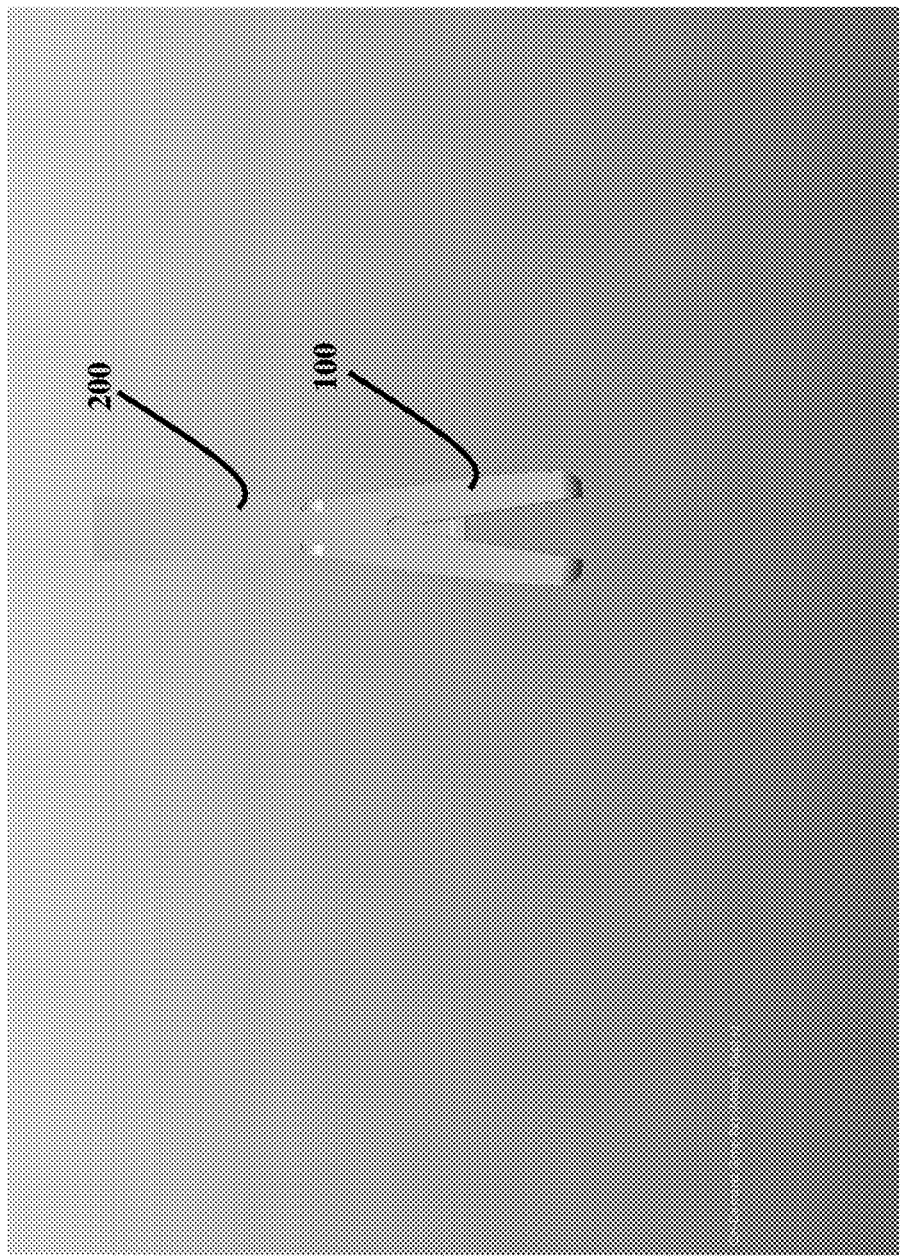
FIG. 6F illustrates a side view of the inserter device of FIG. 5 after engaging and implanting the interbody implant device of FIG. 1 with five clicks, in its final position with the interbody implant device of FIG. 1 being fully deployed, according to an embodiment herein.
Figure 6G:
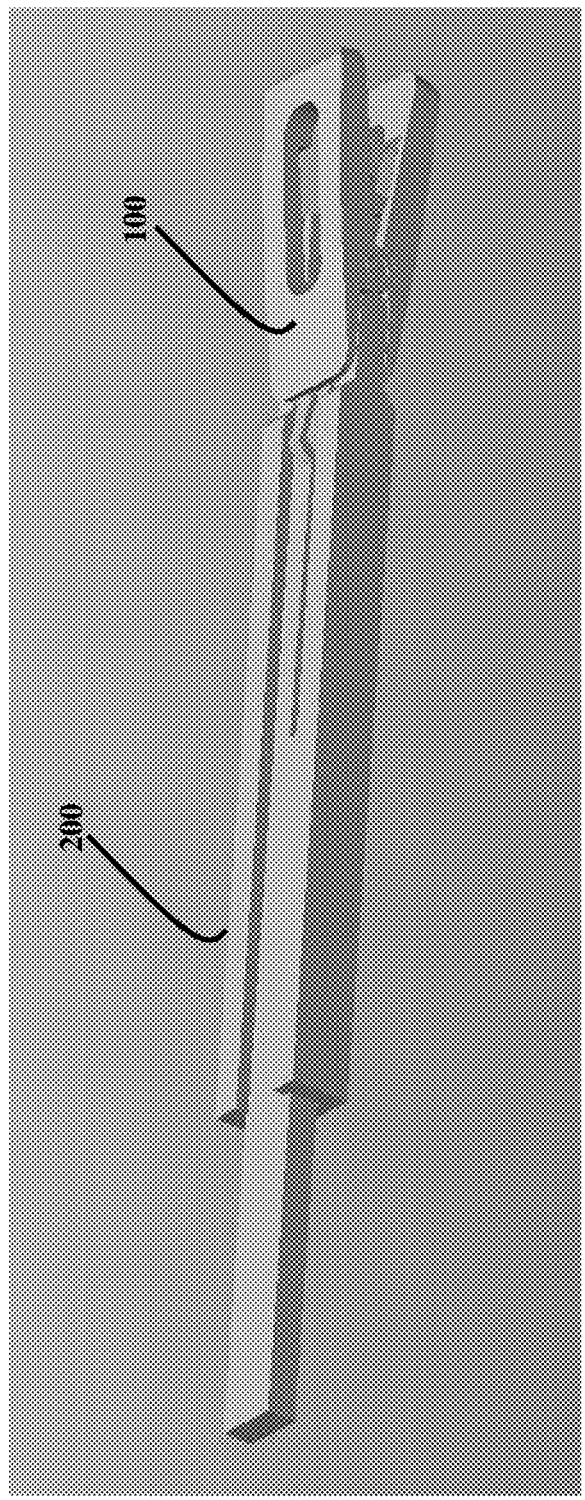
FIG. 6G illustrates a perspective view of the inserter device of FIG. 5 after engaging and implanting the interbody implant device of FIG. 1, in its final position with the interbody implant device of FIG. 1 being fully deployed, according to an embodiment herein.
Figure 6H:
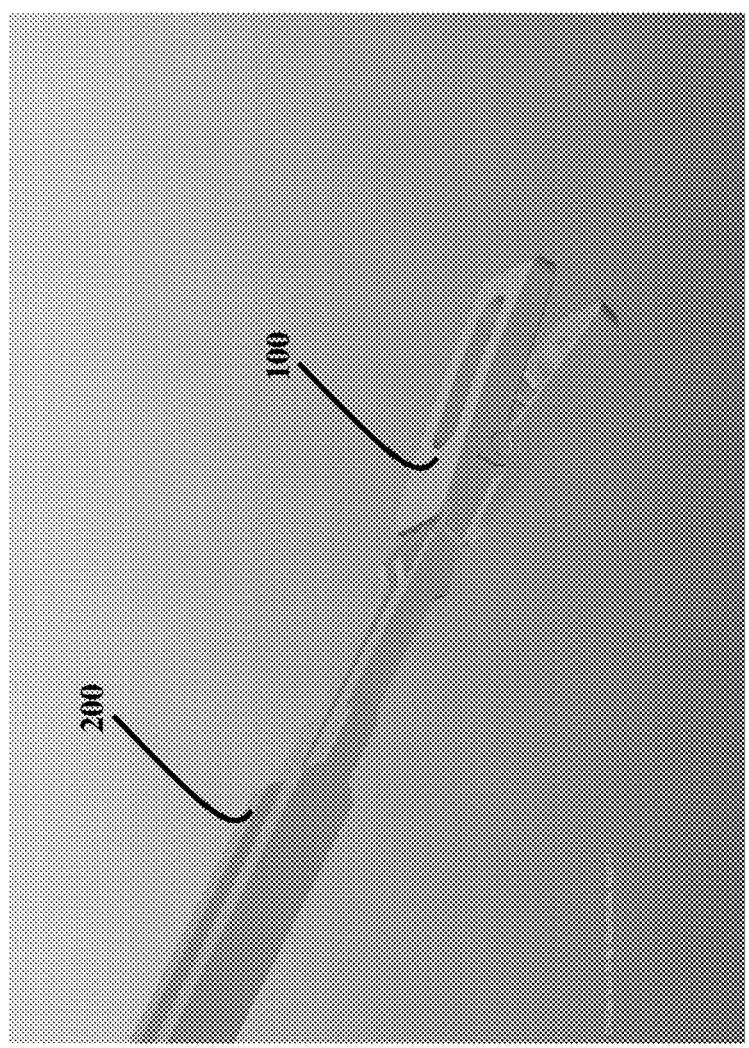
FIG. 6H illustrates a perspective view of the inserter device of FIG. 5 releasing the deployed interbody implant device of FIG. 1 according to an embodiment herein.

FIGS. 6A through 6H, with reference to FIGS. 1 through 5, illustrate the inserter 200 engaging the device 100. The inserter 200 further comprises a shaft portion 210 which permits easy of manipulation of the inserter 200 by a user (not shown). FIG. 6A illustrates the inserter 200 initially engaging the device 100. FIG. 6B illustrates a side view of the inserter 200 after engaging the device 100. FIG. 6C illustrates another side view of the inserter 200 after engaging the device 100. FIG. 6D illustrates a front view of the inserter 200 after engaging the device 100. FIG. 6E illustrates a side view of the inserter 200 after engaging and implanting the device 100 with three clicks. FIG. 6F illustrates a side view of the inserter 200 after engaging and implanting the device 100 with five clicks, in its final position with the device 100 being fully deployed. FIG. 6G illustrates a perspective view of the inserter 200 after engaging and implanting the device 100, in its final position with the device 100 being fully deployed. FIG. 6H illustrates a perspective view of the inserter 200 releasing the deployed device 100.

FIGS. 7A through 7C, with reference to FIGS. 1 through 6H, illustrate a second embodiment of an interbody device 300. In these embodiments, the actuating clip 304 extends beyond the outside edge of the first and second clip components 301, 302 (e.g., beyond the confines (e.g., length/width) of the first and second clip components 301, 302). FIG. 7A illustrates a top view of the device 300 showing the second clip component 302, the actuating clip 304, and the corresponding windows 307, 341 (of the first and second clip component 301, 302 and actuating clip 304, respectively). FIG. 7B illustrates a perspective view of the device 300 with the actuating clip 304 inserted between the first and second clip components 301, 302. FIG. 7C illustrates a perspective view of the device 300 with the actuating clip 304 304 inserted between the first and second clip components 301, 302, and in an expanded position.

Figure 8B:
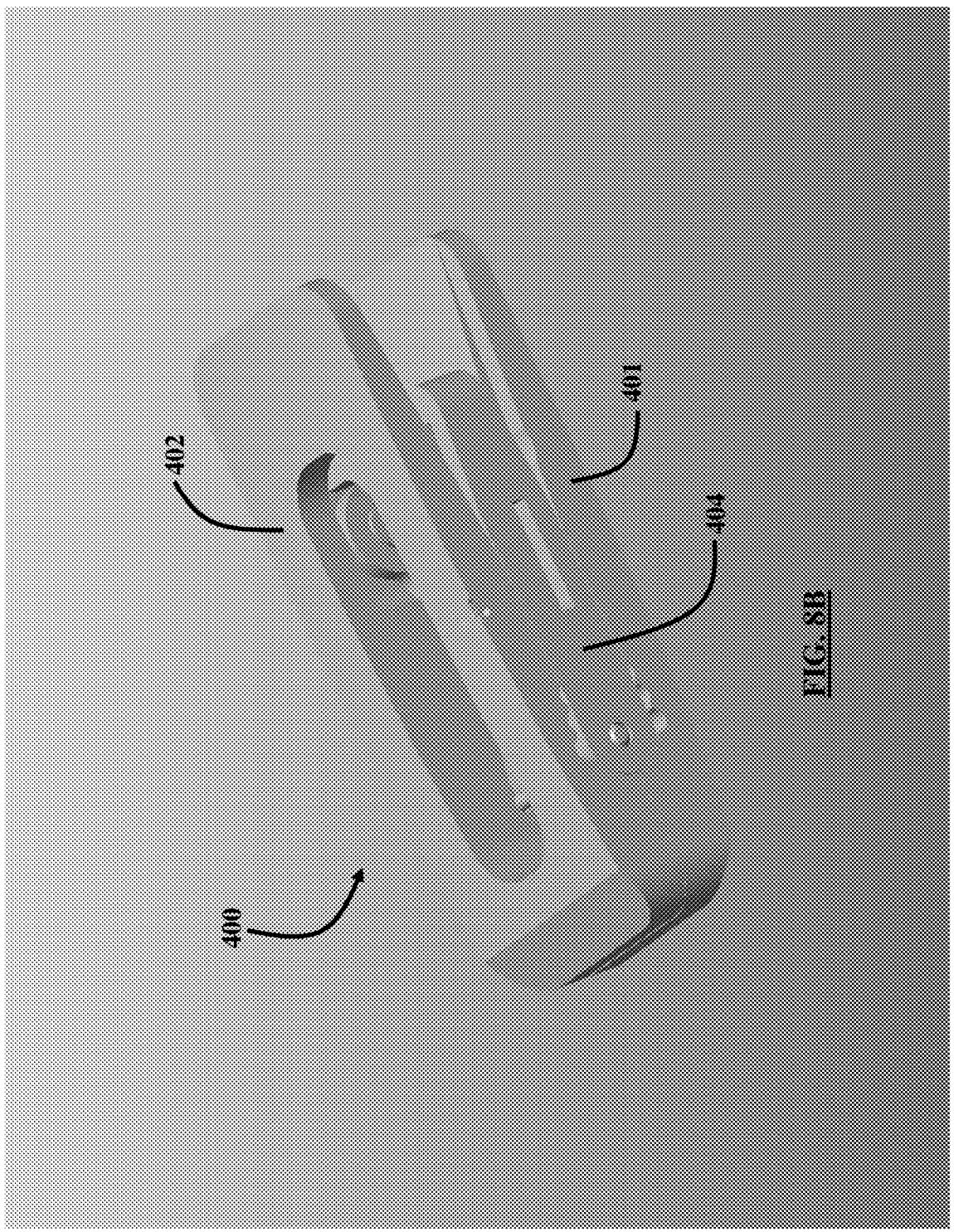
FIG. 8B illustrates a perspective view of the device of FIG. 8A in one position according to a third embodiment herein.

FIGS. 8A through 8C, with reference to FIGS. 1 through 7C, illustrate a third embodiment of an interbody device 400. FIG. 8A illustrates an exploded view of the device 400 comprising a first clip component 401, a second clip component 402, a first hinge pin 403a, a second hinge pin 403b, an actuating clip 404, and an elongated pin 406. FIG. 8B illustrates a perspective view of the device 400 in one position. FIG. 8C illustrates a perspective view of the device 400 in another position. The first and second clip components 401, 402 are substantially configured similarly to the first and second clip components 101, 102 shown and described in FIGS. 4A and 4B. The actuating clip 404 is substantially U-shaped comprising a pair of arms 427a, 427b that are connected by a connection bar 412 with an open window 441 therebetween. The window 441 substantially alights with the window 407 of the first and second clip components 401, 402. The connection bar 412 may be configured to have a slightly curved and outwardly protruding middle portion 418 comprising a hole 422.

The arms 427a, 427b comprise a channel 420a, 420b. The actuating clip 404 further includes a first end 408 opposite to the second end 416 where the connection bar 412 is located. The first end 408 comprises flanges 433a, 433b that are configured with holes 414a, 414b that accommodate the elongated pin 406. The flanges 433a, 433b are dimensioned and configured to engage the groove portion 411a, 411b of the first and second clip components 401, 402. The hinge pins 403a, 403b engage the corresponding sockets 409a, 409b of the first and second clip components 401, 402. The elongated pin 406 is configured with a substantially elongated shaft 430 with a first stop 432 adjacent to a first cap 434 at one end 436 of the pin 406, and with a second stop 438 adjacent to a second cap 440 at a second end 442 of the pin 406.

The interbody device 100, 300, 400 provided by the embodiments herein include the following features: packability of bone (through windows 107, 141, 441), impactable (very bulleted at insertion), limited spring action in front to avoid subsidence, expandable, medium and larger sizes may be PEEK, may achieve up to 18 degrees lordosis on larger sizes, easy to insert with best visualization, does not use a threaded mechanism to work avoiding torsional stress on bone.

Moreover, the embodiments herein achieve extra lordosis than most conventional devices to avoid flat back syndrome and more revision surgery (sagital balance). The interbody device 100, 300, 400 is negatively tapered towards anteriorly for easiest insertion, and then expands in the front to properly restore sagital balance. The interbody device 100, 300, 400 is comprised of fewer parts than conventional devices to be more reliable and impactable to distract disc space, and allows for limited spring action in the front to cushion the forces on the mating bone. The interbody device 100, 300, 400 allows for an inserter 200 that is smaller (e.g., thinner) than the implant 100 for good visualization during passing by nerve anatomy, and avoids a living hinge as to not stress the material of the device 100, 300, 400 and have it fail after or during implantation. The interbody device 100, 300, 400 is activated incrementally over 5 or more "clicks" that may be observed by the user tactilely or audibly, where other conventional devices are all or none in terms of expansion (e.g., no incremental clicks/steps). Definite and positive expansion stations secured by the grooves 139 on both sides of the interbody device 100, 300, 400 allow for implantation at partial expansion where other conventional devices merely have a smooth ramp. The interbody device 100, 300, 400 may be used as part of a surgical technique according to the embodiments herein.

Figure 9B:
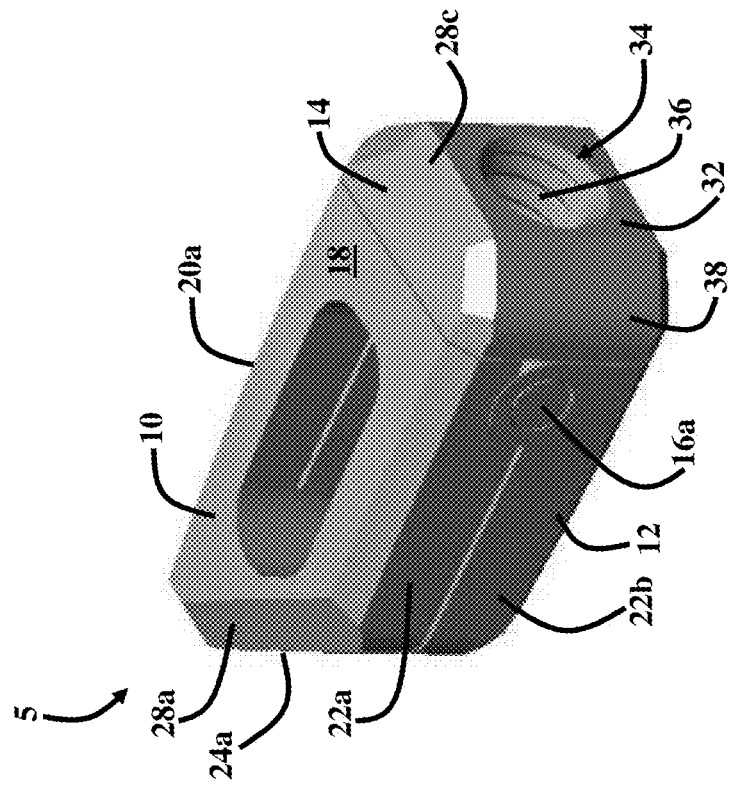
FIG. 9B illustrates a rear perspective view of an expandable interbody device in a closed configuration according to a fourth embodiment herein.
Figure 9A:
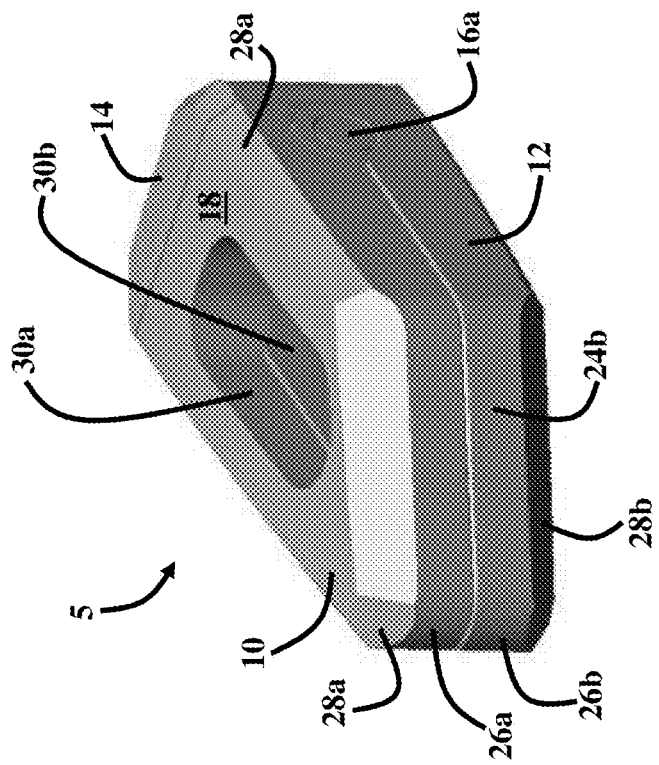
FIG. 9A illustrates a front perspective view of an expandable interbody device in a closed configuration according to a fourth embodiment herein.
Figure 9D:
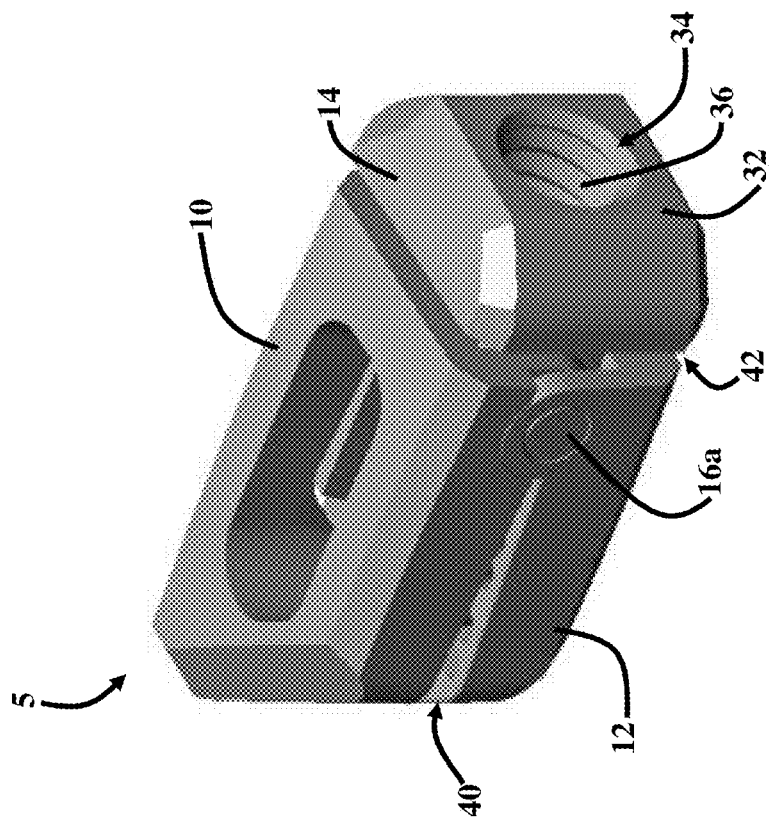
FIG. 9D illustrates a rear perspective view of an expandable interbody device in a 0° open configuration according to a fourth embodiment herein.
Figure 9C:
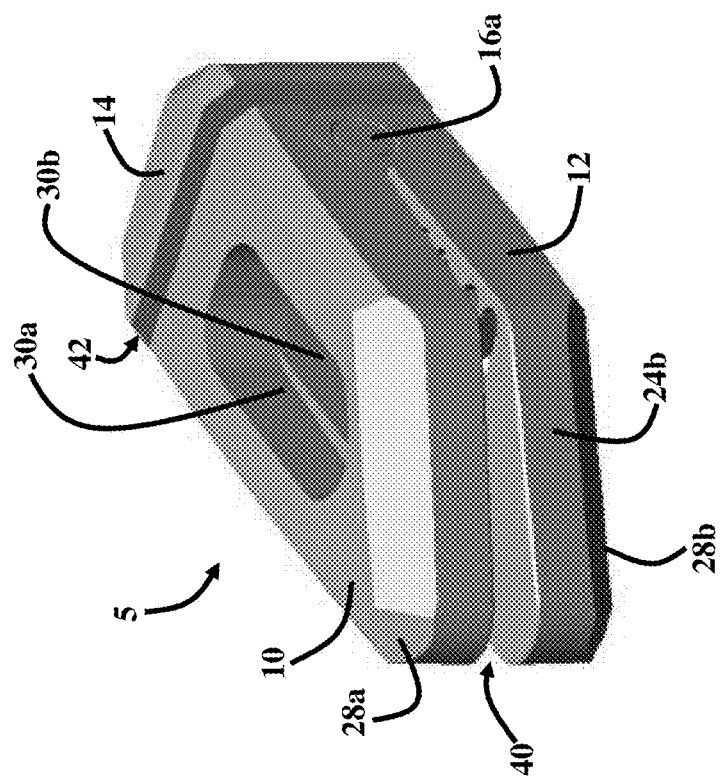
FIG. 9C illustrates a front perspective view of an expandable interbody device in a 0° open configuration according to a fourth embodiment herein.
Figure 9F:
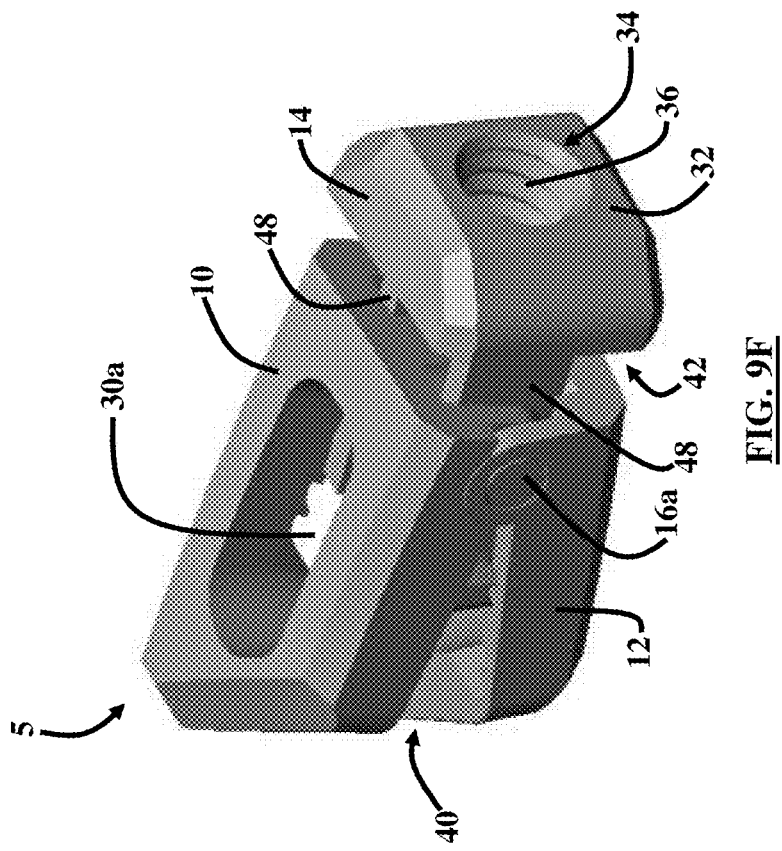
FIG. 9F illustrates a rear perspective view of an expandable interbody device in a 8° open configuration according to a fourth embodiment herein.
Figure 9E:
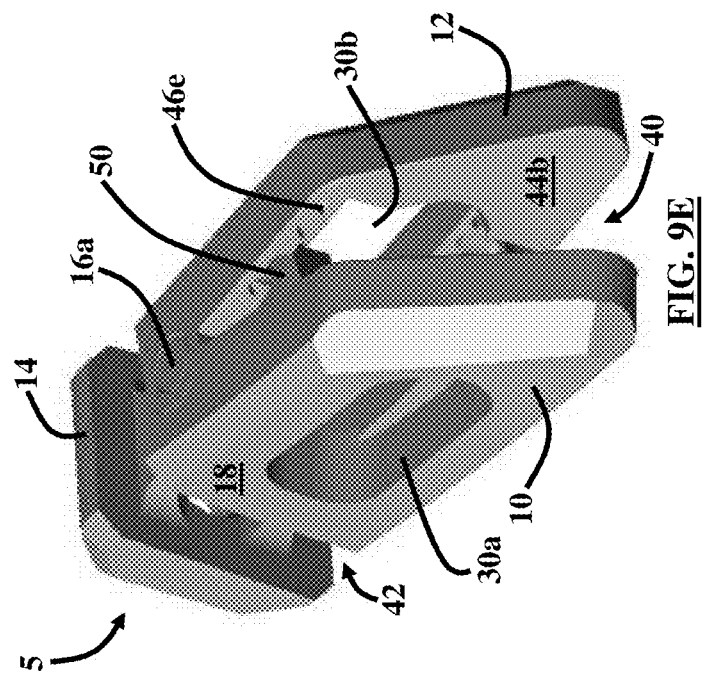
FIG. 9E illustrates a front perspective view of an expandable interbody device in a 8° open configuration according to a fourth embodiment herein.

FIGS. 9A through 9H illustrate various perspective views of an expandable interbody device 5 according to a fourth embodiment herein. FIG. 9A illustrates a front perspective view of an expandable interbody device 5 in a closed configuration according to a fourth embodiment herein. FIG. 9B illustrates a rear perspective view of the expandable interbody device 5 in a closed configuration according to a fourth embodiment herein. FIG. 9C illustrates a front perspective view of the expandable interbody device 5 in a 0° open configuration according to a fourth embodiment herein. FIG. 9D illustrates a rear perspective view of the expandable interbody device 5 in a 0° open configuration according to a fourth embodiment herein. FIG. 9E illustrates a front perspective view of the expandable interbody device 5 in a 8° open configuration according to a fourth embodiment herein. FIG. 9F illustrates a rear perspective view of the expandable interbody device 5 in a 8° open configuration according to a fourth embodiment herein. FIG. 9G illustrates a front perspective view of the expandable interbody device 5 in a 16° open configuration according to a fourth embodiment herein. FIG. 9H illustrates a rear perspective view of the expandable interbody device 5 in a 16° open configuration according to a fourth embodiment herein.

The interbody device 5 comprises a first articulating member 10 and a second articulating member 12, which are rotationally connected to one another using a pair of pins 16a, 16b (pin 16b is shown in FIGS. 13A through 13D). The interbody device 5 further includes a clip member 14 configured to cause the first and second articulating members 10, 12 to rotate (or "expand") relative to each other. The first and second articulating members 10, 12 as well as the clip member 14 generally comprise a smooth outer surface 18 in one embodiment. The first articulating member 10 and the second articulating member 12 are similarly configured in order to align in a complementary manner to create a uniform outer surface 18. The first articulating member 10 comprises a first long sidewall 20a positioned opposite to a first short sidewall 22a. A first angled front wall 24a connects the first short sidewall 22a to a beveled first nose 26a at the front of the interbody device 5. The first nose 26a is disposed between the first long sidewall 20a and the first angled front wall 24a. Similarly, the second articulating member 12 comprises a second short sidewall 22b positioned opposite to a second long sidewall 20b. A second angled front wall 24b connects the second long sidewall 20b to a beveled second nose 26b at the front of the interbody device 5. The second nose 26b is disposed between the second short sidewall 22b and the second angled front wall 24b. When positioned together in the closed state (e.g., FIGS. 9A, 9B, 13A, 14A, and 15A), the first long sidewall 20a and second long sidewall 20b align with one another, the first short sidewall 22a and second short sidewall 22b align with one another, the first angled front wall 24a and second angled front wall 24b align with one another, and the first nose 26a and second nose 26b align with one another. The first articulating member 10 further comprises a first beveled edge 28a, the second articulating member 12 further comprises a second beveled edge 28b, and the clip member 14 comprises a clip beveled edge 28c all to better match endplate anatomy. The first articulating member 10 also includes a first hole 30a disposed generally through the middle of the first articulating member 10. Likewise, the second articulating member 12 also includes a second hole 30b disposed generally through the middle of the second articulating member 12. When positioned together in the closed state (e.g., FIGS. 9A, 9B, 13A, 14A, and 15A), the first hole 20a and second hole 30b align to create a bone graft window for the interbody device 5.

The clip member 14 further comprises a head portion 32 having a hole 34 disposed through a substantially central portion thereof. The hole 24 comprises threads 36, and the head portion 32 comprises generally curved edges 38 to further better match endplate anatomy. As shown in FIGS. 9C through 9H, once the interbody device 5 begins to open, the relative rotational movement of the first articulating member 10 and the second articulating member 12 create an angled opening 40 between the first articulating member 10 and the second articulating member 12, and also create a separation between the head portion 32 of the clip member 14 and each of the first and second articulating members 10, 12. The manner in which the angled opening 40 and separation 42 are created are further described below.

FIG. 10, with reference to FIGS. 9A through 9H, illustrates a perspective view of the first articulating member 10 of the expandable interbody device 5 of FIGS. 9A through 9H according to a fourth embodiment herein. The first articulating member 10 comprises a first inner face 44a comprising a first groove wall 54a such that the first groove wall 54a is part of the first short sidewall 22a of the first articulating member 10. The first groove wall 54a comprises a first ramp portion 56a and a first set of grooves 46a-46d arranged such that the grooves 46a-46d are progressively elongated as they near the first nose 26a side of the first articulating member 10 (e.g., groove 46a is longer than groove 46b, which is longer than groove 46c, which is longer than groove 46d). Furthermore, the configuration of the first set of grooves 46a-46d corresponds with the "clicks" for the various stages of opening/engagement of the interbody device 5. Disposed between second groove 46b and third groove 46d is a first spacer 58a. The progressively elongated configuration of the grooves 46a-46d corresponds with the incline of the first ramp portion 56a. The second groove wall 54b of the first articulating member 10 is identically configured to the first groove wall 54a. A first inner sidewall 52a is disposed around the interior of the first articulating member 10 and defines the dimension and configuration of the first hole 30a. The first articulating member 10 further comprises a first raised bar 62a disposed on top of the first inner sidewall 52a and positioned at a back end 64a of the first articulating member 10 opposite from the first nose 26a. Disposed on opposite sides of the first raised bar 62a are a first pair of sockets 66a, 66b respectively comprising a first pair of pin holes 68a, 68b. A substantially curved cut-out well 70 is configured adjacent to each of the first pair of sockets 66a, 66b.

FIG. 11, with reference to FIGS. 9A through 10, illustrates a perspective view of the second articulating member 12 of the expandable interbody device 5 of FIGS. 9A through 9H according to a fourth embodiment herein. The second articulating member 12 comprises a second inner face 44b comprising a first groove wall 54c such that the first groove wall 54c is part of the second short sidewall 22b of the second articulating member 12. The first groove wall 54c comprises a second ramp portion 56b and a second set of grooves 46e-46h arranged such that the grooves 46e-46h are progressively elongated as they near the second nose 26b side of the second articulating member 12 (e.g., groove 46e is longer than groove 46f, which is longer than groove 46g, which is longer than groove 46h). Furthermore, the configuration of the second set of grooves 46e-46h corresponds with the "clicks" for the various stages of opening/engagement of the interbody device 5. Disposed between second groove 46f and third groove 46g is a second spacer 58b. The progressively elongated configuration of the grooves 46e-46h corresponds with the incline of the second ramp portion 56b. The second groove wall 54d of the second articulating member 12 is identically configured to the first groove wall 54c. A second inner sidewall 52b is disposed around the interior of the second articulating member 12 and defines the dimension and configuration of the second hole 30b. The second articulating member 12 further comprises a second raised bar 62b disposed on top of the second inner sidewall 52b and positioned at a back end 64b of the second articulating member 12 opposite from the second nose 26b. Disposed on opposite sides of the second raised bar 62b are a second pair of sockets 66c, 66d respectively comprising a second pair of pin holes 68c, 68d. A platform 60 is configured adjacent to the second pair of sockets 66c, 66d.

When the first articulating member 10 is aligned with the second articulating member 12 the various components described above align with one another. For example, the second pair of sockets 66c, 66d of the second articulating member 12 each fit in the respective cut-out wells 70 of the first articulating member 10 such that the first pair of pin holes 68a, 68b of the first articulating member 10 aligns with the second pair of pin holes 68c, 68d of the second articulating member 12. This permits the pins 16a, 16b to be inserted to allow for rotational movement of the first articulating member 10 with respect to the second articulating member 12, but still allow for retention of the first articulating member 10 and second articulating member 12 together without separating completely. The platform 60 allows the first pair of sockets 66a, 66b to rest thereon upon alignment of the first articulating member 10 with the second articulating member 12. Furthermore, the various grooves 46a-46d of the first articulating member 10 align with the correspondingly configured grooves 46d-46h of the second articulating member 12 upon alignment of the first articulating member 10 with the second articulating member 12. Additionally, the first raised bar 62a and second raised bar 62b also align together as does the first hole 30a with the second hole 30b.

FIG. 12, with reference to FIGS. 9A through 11, illustrates a perspective view of the clip member 14 of the expandable interbody device 5 of FIGS. 9A through 9H according to a fourth embodiment herein. As shown in FIG. 12, the head portion 32 of the clip member 14 includes the hole 34 configured therethrough with threads 26 configured in the hole 34. The back wall 72 of the head portion 32 comprises a pair of substantially parallel cantilever arms 48 outwardly protruding therefrom. The pair of arms 48 are appropriated spaced apart from each other to create a space 65 therebetween. The end 78 of each arm 48 comprises a prong 50 comprising opposed protruding tips 74, 76 such that the height of each prong 50 is greater than the height of each arm 48, wherein the protruding tip 74 extends beyond the top 47 of the arm 48, and wherein the protruding tip 76 extends beyond the bottom 49 of the arm 48.

The protruding tips 74, 76 are dimensioned and configured to engage the various grooves 46a-46h of the respective first and second articulating members 10, 12 when the clip member 14 is inserted into and in between the first and second articulating members 10, 12. The clip member 14 is inserted into and in between the first and second articulating members 10, 12 such that the back wall 72 of the clip member 14 is adjacent to the back ends 64a, 64b of the first and second articulating members 10, 12, respectively.

In one embodiment, the first and second ramp portions 56a, 56b and grooves 46a-46d (or grooves 46e-46h) may be configured on only one of the articulating members (e.g., either articulating member 10 or articulating member 12) (not shown) rather than both members 10, 12 as indicated in the drawings. In such an embodiment, the clip member 14 would only have protruding tip 74 or 76 but not both. Furthermore, in another embodiment (not shown), there could be an upward protruding tip 74 and a downward protruding tip 76 on opposite sides of the pair of arms 48.

The major positional control of the clip member 14 within the interbody device 5 is controlled by the protruding tips 74, 76 in the timed associated grooves 46a-46h of the interrupted ramp portions 56a, 56b. The prong 50 of the clip member 14 may sit in these grooves 46a-46h with some clearance; however the protruding tips 74, 76 are what click and control the position of the clip member 14.

FIGS. 13A through 15D, with reference to FIGS. 9A through 12, illustrate various views of the interbody device 5 in the four stages of operation of the interbody device 5: closed, 0°, 8°, and 16°. FIG. 13A illustrates a side view of the expandable interbody device 5 of FIGS. 9A and 9B in a closed configuration according to a fourth embodiment herein. FIG. 14A illustrates a top view of the expandable interbody device 5 of FIGS. 9A and 9B in a closed configuration according to a fourth embodiment herein. FIG. 15A illustrates a rear perspective view of the expandable interbody device 5 of FIGS. 9A and 9B in a closed configuration according to a fourth embodiment herein. As shown in FIGS. 13A, 14A, and 15A, the first articulating member 10 is not separated from the second articulating member 12 as the clip member 14 is fully engaged with the first and second articulating members 12, 14. Although not shown in FIGS. 13A, 14A, and 15A, in this configuration the protruding tips 74, 76 of the clip member 14 are seated in the first grooves 46a, 46e of the first and second articulating members 12, 14.

FIG. 13B illustrates a side view of the expandable interbody device 5 of FIGS. 9C and 9D in a 0° open configuration according to a fourth embodiment herein. FIG. 14B illustrates a top view of the expandable interbody device 5 of FIGS. 9C and 9D in a 0° open configuration according to a fourth embodiment herein. FIG. 15B illustrates a rear perspective view of the expandable interbody device 5 of FIGS. 9C and 9D in a 0° open configuration according to a fourth embodiment herein. As shown in FIGS. 13B, 14B, and 15B, the first articulating member 10 is separated from the second articulating member 12 creating an angled opening 40 and a separation 42 between the clip member 14 and the first and second articulating members 12, 14. Although not shown in FIGS. 13B, 14B, and 15B, in this configuration the protruding tips 74, 76 of the clip member 14 are seated in the second grooves 46b, 46f of the first and second articulating members 12, 14, which pushes the back wall 72 of clip member 14 away from the back ends 64a, 64b of the respective first and second articulating members 12, 14.

FIG. 13C illustrates a side view of the expandable interbody device 5 of FIGS. 9E and 9F in a 8° open configuration according to a fourth embodiment herein. FIG. 14C illustrates a top view of the expandable interbody device 5 of FIGS. 9E and 9F in a 8° open configuration according to a fourth embodiment herein. FIG. 15C illustrates a rear perspective view of the expandable interbody device 5 of FIGS. 9E and 9F in a 8° open configuration according to a fourth embodiment herein. As shown in FIGS. 13C, 14C, and 15C, the first articulating member 10 is further separated from the second articulating member 12 creating an even larger angled opening 40 and a larger separation 42 between the clip member 14 and the first and second articulating members 12, 14 (larger compared with the angled opening 40 and separation 42 of FIGS. 13B, 14B, and 15B). Although not shown in FIGS. 13C, 14C, and 15C, in this configuration the protruding tips 74, 76 of the clip member 14 are seated in the third grooves 46c, 46g of the first and second articulating members 12, 14, which pushes the back wall 72 of clip member 14 further away from the back ends 64a, 64b of the respective first and second articulating members 12, 14.

FIG. 13D illustrates a side view of the expandable interbody device 5 of FIGS. 9G and 9H in a 16° open configuration according to a fourth embodiment herein. FIG. 14D illustrates a top view of the expandable interbody device 5 of FIGS. 9G and 9H in a 16° open configuration according to a fourth embodiment herein. FIG. 15D illustrates a rear perspective view of the expandable interbody device 5 of FIGS. 9G and 9H in a 16° open configuration according to a fourth embodiment herein. As shown in FIGS. 13D, 14D, and 15D, the first articulating member 10 is even further separated from the second articulating member 12 creating an even larger angled opening 40 and a larger separation 42 between the clip member 14 and the first and second articulating members 12, 14 (larger compared with the angled opening 40 and separation 42 of FIGS. 13C, 14C, and 15C). Although not shown in FIGS. 13D, 14D, and 14D, in this configuration the protruding tips 74, 76 of the clip member 14 are seated in the third grooves 46d, 46h of the first and second articulating members 12, 14, which pushes the back wall 72 of clip member 14 further away from the back ends 64a, 64b of the respective first and second articulating members 12, 14.

Table 1 below provides the relative comparison of the relative dimensions of the maximum tip height (MH), expansion height (EH), and medial length (EL) indicated in FIGS. 14D and 15D. It should be noted that the listed dimensions are examples only, and the embodiments herein are not restricted to a particular dimension or configuration. In the following examples, the height of the interbody device 5 is taken to be 10 mm, the width of the interbody device 5 is taken to be 11 mm, and the first and second holes 30a, 30b (graft window) is taken to be 12×5 mm

TABLE 1

Dimensional Comparison

| Angle | Maximum Tip Height (MH) | Expansion Height (EH) | Medial Length (ML) |
|---|---|---|---|
| Closed | 8 mm | (9.5 mm) | 25 mm |
| 0° | 9.5 mm | 10 mm | 26.5 mm |
| 8° | 13 mm | 12 mm | 28.5 mm |
| 16° | 16.5 mm | 13.5 mm | 29.5 mm |

Figure 16:
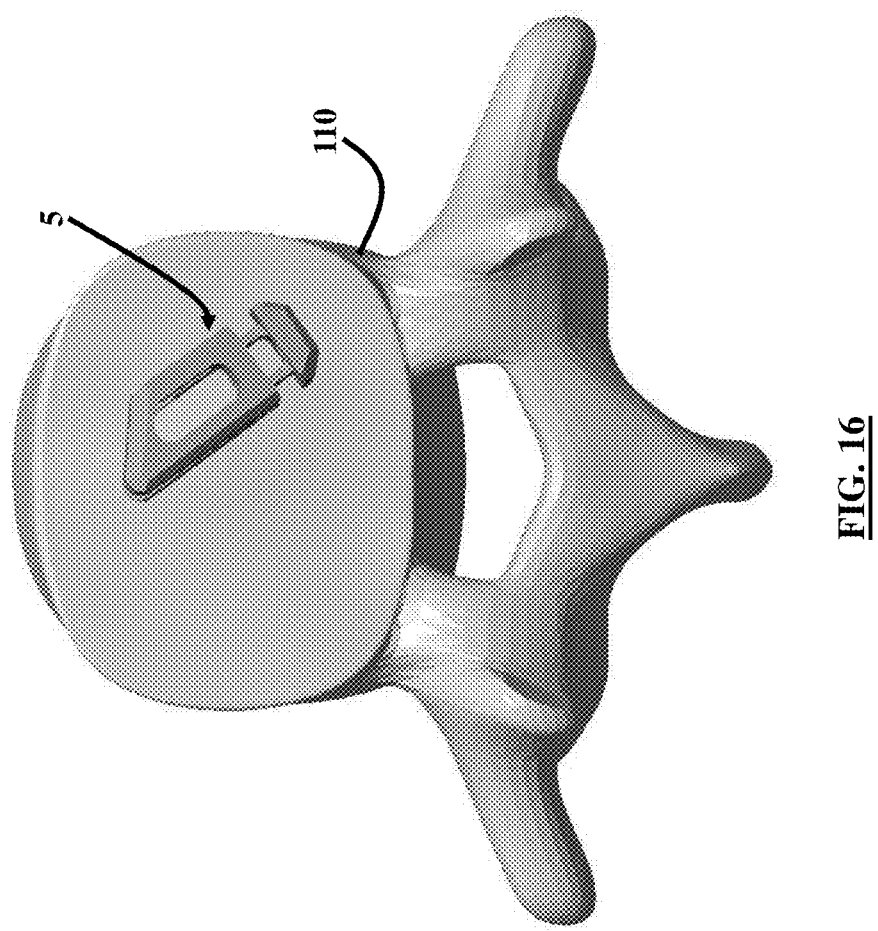
FIG. 16 illustrates a top view of the expandable interbody device of FIGS. 9A through 9H inserted into a vertebral body according to a fourth embodiment herein.

FIG. 16, with reference to FIGS. 9A through 15D, illustrates a top view of the expandable interbody device 5 of FIGS. 9A through 9H inserted into a vertebral body 110 according to a fourth embodiment herein. The interbody device 5 is inserted into the vertebral body 110 using an appropriately configured inserter device 80, and example of which is shown in FIGS. 17A through 22B, with reference to FIGS. 9A through 16.

Figure 17A:
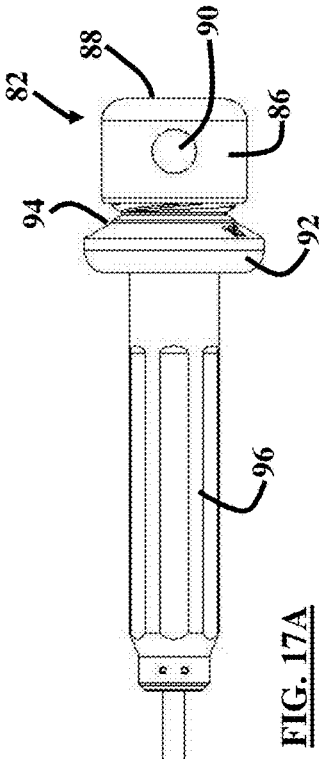
FIG. 17A illustrates a side view of an inserter device used with the expandable interbody device of FIGS. 9A through 9H according to a fourth embodiment herein.
Figure 17B:
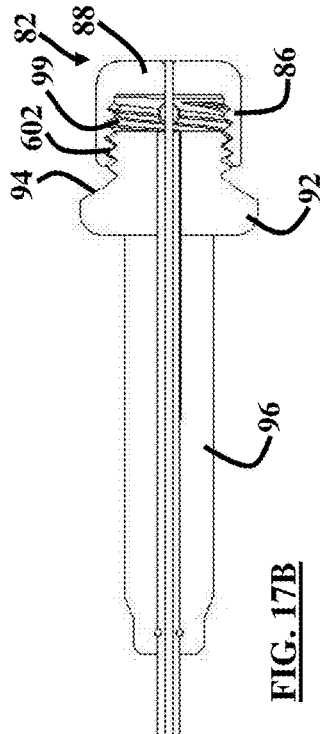
FIG. 17B illustrates a cross-sectional view of the inserter device of FIG. 17A according to a fourth embodiment herein.

FIG. 17A illustrates a side view of an inserter device 80 used with the expandable interbody device 5 of FIGS. 9A through 9H according to a fourth embodiment herein. FIG. 17B illustrates a cross-sectional view of the inserter device 80 of FIG. 17A according to a fourth embodiment herein. The inserter device 80 comprises a first end 82 oppositely positioned from a second end 84. The inserter device 80 further comprises an inner shaft 112. A knob 86 is configured at the first end 82, wherein the knob comprises a dial 88, a pair of arms 90, and internally configured threads 99. A bumper 92 is positioned adjacent to the knob 86. The bumper 92 comprises a generally sloping neck portion 94 that terminates with threads 602 that are complimentary configured to engage the threads 99 of the knob 86. Accordingly, the knob 86 is rotationally connected to the bumper 94 upon turning the knob 86 using the pair of arms 90. A gripping portion 96 of the inserter device 80 is connected to the bumper 92. Extending through the gripping portion and outwardly protruding therefrom and attached thereto is an elongated shaft 98 that terminates with a threaded engagement member 600 at the second end 84 of the insert device 80.

The elongated shaft 98 is cannulated and allows passage of a separate inner shaft 112 that is permanently connected to knob 86. When the knob 86 is turned on threads 602, the inner shaft 112 advances through shaft 98 and the threaded tip 600. As best shown in FIG. 22B, the tip 114 of the inner shaft 112 then contacts the first and second raised bars 62a, 62b of the interbody device 5, which cause the interbody device 5 to articulate and hinge open. The cannulated elongated shaft 98 allows packing of bone graft after deployment of the interbody device 5 by acting as a funnel. The inner shaft 112 connected to the knob 86 may be used to push bone graft via the bumper 92 through the outer cannulated elongated shaft 98 into and behind the interbody device 5 after the inserter device 80 is removed (e.g., after insertion of the interbody device 5 into the vertebral body 110).

Figure 18B:
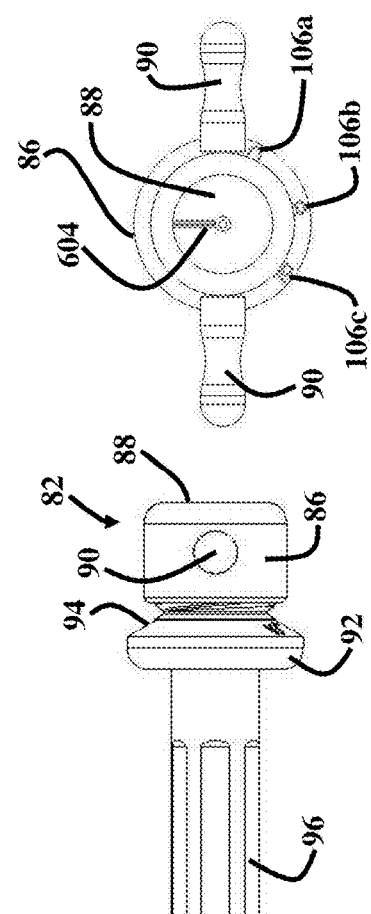
FIG. 18B illustrates an end view of the inserter device of FIG. 17A according to a fourth embodiment herein.
Figure 18A:
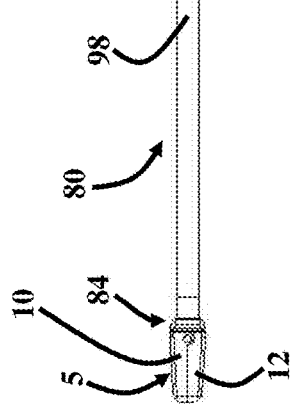
FIG. 18A illustrates a side view of an inserter device engaging the expandable interbody device of FIGS. 9A through 9B according to a fourth embodiment herein.

FIGS. 18A and 18B, with reference to FIGS. 9A through 17B, illustrate the inserter device 80 engaging the interbody device 5 in a closed configuration. FIG. 18A illustrates a side view of an inserter device 80 engaging the expandable interbody device 5 of FIGS. 9A through 9B according to a fourth embodiment herein. FIG. 18B illustrates an end view of the inserter device 80 of FIG. 18A according to a fourth embodiment herein. The threaded engagement member 600 of the inserter device 80 comprises threads 108 (best shown in FIGS. 22A and 22B) that are dimensioned and configured to complementarily engage the threads 36 of hole 34 of the clip member 14. FIG. 18B further illustrates the knob 86 with the outwardly extended pair of arms 90 to allow for ease of rotation of the knob 86. The dial 88 comprises an indicator 604 that is configured to align with various markings 106a-106c configured around the dial 88 and associated with the various stages of configuration of the interbody device 5 (e.g., 0°, 8°, and 16°) as the knob 86 is turned. Initially, the clip member 14 is fully seated in between the first and second articulating members 10, 12 (as indicated in FIGS. 9A, 9B, 13A, 14A, and 15A) such that the protruding tips 74, 76 of the clip member 14 are seated in grooves 46a, 46e of the respective first and second articulating members 10, 12. Then, the threads 108 of the threaded engagement member 600 of the shaft 98 are fully engaged with the threads 36 of the clip member 14. Next, the interbody device 5 is assembled to inserter 80 by turning the threads 36 of the clip member on threaded engagement member 600 to hand tightness to prevent disassembly from threads 108. Thereafter, the inner shaft 112 is permitted to translate (slide) through shaft 98 upon rotation of the knob 86. This sliding action of the inner shaft 112 further through the shaft 98 and gripping portion 96 subassembly permits the pushing of the first and second articulating members 10, 12 such that the clip member 14 maintains position on inserter 80 while the first and second articulating members 10, 12 are articulated such that each stage of pushing is associated with the corresponding stages of configuration of the interbody device 5 (e.g., 0°, 8°, and 16°). Furthermore, each of the stages of configuration of the interbody device 5 (e.g., 0°, 8°, and 16°) corresponding with the positioning/seating of the protruding tips 74, 76 into the respective grooves 46a-46h (e.g., first grooves 46a, 46e corresponding to a closed configuration; second grooves 46b, 46f corresponding to a 0° configuration; third grooves 46c, 46g corresponding to a 8° configuration; and fourth grooves 46d, 46h corresponding to a 16° configuration. In the closed configuration, as indicated in FIGS. 18A and 18B, the protruding tips 74, 76 of the clip member 14 are positioned in the first grooves 46a, 46e of the respective first and second articulating members 10, 12.

FIGS. 19A and 19B, with reference to FIGS. 9A through 18B, illustrate the inserter device 80 engaging the interbody device 5 in a 0° configuration. FIG. 19A illustrates a side view of an inserter device 80 engaging the expandable interbody device 5 of FIGS. 9C through 9D according to a fourth embodiment herein. FIG. 19B illustrates an end view of the inserter device 80 of FIG. 19A according to a fourth embodiment herein. Here, the knob 86 is turned to align the indicator 604 to the 0° marking 106a. The rotation of the knob 86 causes the inner shaft 112 to correspondingly slide further through the shaft 98 and gripping portion 96 subassembly, which causes the threaded engagement member 600 on the second end 84 of the inserter device 80 to maintain the position of the clip member 14 while the first and second articulating members 10, 12 are articulated away. Here, the protruding tips 74, 76 of the clip member are seated in the second grooves 46b, 46f of the first and second articulating members 10, 12, which corresponds to the 0° configuration.

FIGS. 20A and 20B, with reference to FIGS. 9A through 19B, illustrate the inserter device 80 engaging the interbody device 5 in a 8° configuration. FIG. 20A illustrates a side view of an inserter device 80 engaging the expandable interbody device 5 of FIGS. 9E through 9F according to a fourth embodiment herein. FIG. 20B illustrates an end view of the inserter device 80 of FIG. 20A according to a fourth embodiment herein. Here, the knob 86 is turned to align the indicator 104 to the 8° marking 106b. The rotation of the knob 86 causes the inner shaft 112 to correspondingly slide further through the shaft 98 and gripping portion 96 subassembly, which causes the threaded engagement member 600 on the second end 84 of the inserter device 80 to maintain the position of clip member 14 while the first and second articulating members 10, 12 are articulated away. Here, the protruding tips 74, 76 of the clip member are seated in the third grooves 46c, 46g of the first and second articulating members 10, 12, which corresponds to the 8° configuration.

FIGS. 21A and 21B, with reference to FIGS. 9A through 20B, illustrate the inserter device 80 engaging the interbody device 5 in a 16° configuration. FIG. 21A illustrates a side view of an inserter device 80 engaging the expandable interbody device 5 of FIGS. 9G through 9H according to a fourth embodiment herein. FIG. 21B illustrates an end view of the inserter device 80 of FIG. 21A according to a fourth embodiment herein. Here, the knob 86 is turned to align the indicator 604 to the 16° marking 106c. The rotation of the knob 86 causes the inner shaft 112 to correspondingly slide further through the shaft 98 and gripping portion 96 subassembly, which causes the threaded engagement member 600 on the second end 84 of the inserter device 80 to maintain the position of clip member 14 while the first and second articulating members 10, 12 are articulated away. Here, the protruding tips 74, 76 of the clip member are seated in the fourth grooves 46d, 46h of the first and second articulating members 10, 12, which corresponds to the 16° configuration.

FIGS. 22A and 22B, with reference to FIGS. 9A through 21B, illustrate magnified cross-sectional views of the interbody device 5 being engaged by the inserter device 80, wherein FIG. 22A illustrates a magnified cross-sectional view of the expandable interbody device 5 being engaged by the inserter device 80 of FIG. 18A according to a fourth embodiment herein, and FIG. 22B illustrates a magnified cross-sectional view of the expandable interbody device 5 being engaged by the inserter device 80 of FIG. 21A according to a fourth embodiment herein. In FIG. 22A, the interbody device 5 is in the closed configuration of (as indicated in FIGS. 9A, 9B, 13A, 14A, and 15A). FIG. 22A magnifies the view of the threaded engagement member 600 of the shaft 98 of the inserter device 80 engaged with the threads 36 of the clip member 14 of the interbody device 5. In FIG. 22B, the interbody device 5 is in the 16° configuration such that the protruding tips 74, 76 of the clip member 14 are seated in the fourth grooves 46d, 46h (the view of the fourth grooves 46d, 46h are obscured in FIG. 22B due to the overlapping view of the protruding tips 74, 76).

The creation of the angled opening 40 and separation 42 of the clip member 14 from the first and second articulating members 10, 12 is caused by the pushing of the first and second articulating members 10, 12 while the position of the clip member 14 is maintained on threaded engagement member 600 such that the protruding tips 74, 76 sequentially move along the first and second ramp portions 56a, 56b from the first groove 46a, 46e towards the fourth groove 46d, 46h. Since the prong 50 on each arm 48 of the clip member 14 remain in a rigid configuration and do not compress, the incline of the first and second ramp portions 56a, 56b cause the first and second articulating members 10, 12 to outwardly rotate away from one another about the pins 16a, 16b as the protruding tips 74, 76 sequentially move along the first and second ramp portions 56a, 56b from the first grooves 46a, 46e towards the fourth grooves 46d, 46h, such that the protruding tips 74, 76 exert a sufficient force against the respective first and second articulating members 10, 12 causing the first and second articulating members 10, 12 to open (e.g., rotatably expand) with respect to one another. The reduced open area between the first and second ramp portions 56a, 56b after the fourth grooves 46d, 46h prevent the clip member 14 from fully disengaging from the interbody device 5.

The interbody device 5 remains fixed into a desired configuration (e.g., 0°, 8°, and 16°) because it is under compression in the interbody space. Protruding tips 74, 76 are compressed and held into the associated grooves 46b-46d (and grooves 46f-46h) by intervertebral loading and supplemental fixation of a pedicle screw construct assembly (not shown). The configuration cannot change because there is no direct force on clip member 14 to compress it towards the first and second articulating members 10, 12.

While the above description and drawings refer to three stages of configuration (e.g., 0°, 8°, and 16°), those skilled in the art would recognize that other stages of configuration including additional ranges or more/less positions could be added or removed in accordance with the embodiments herein. This could occur by adjusting the angle and/or length of the first and second ramp portions 56a, 56b and/or adjusting the number and/or spacing between the grooves 46a-46d (and similarly between grooves 46e-46h).

Figure 23A:
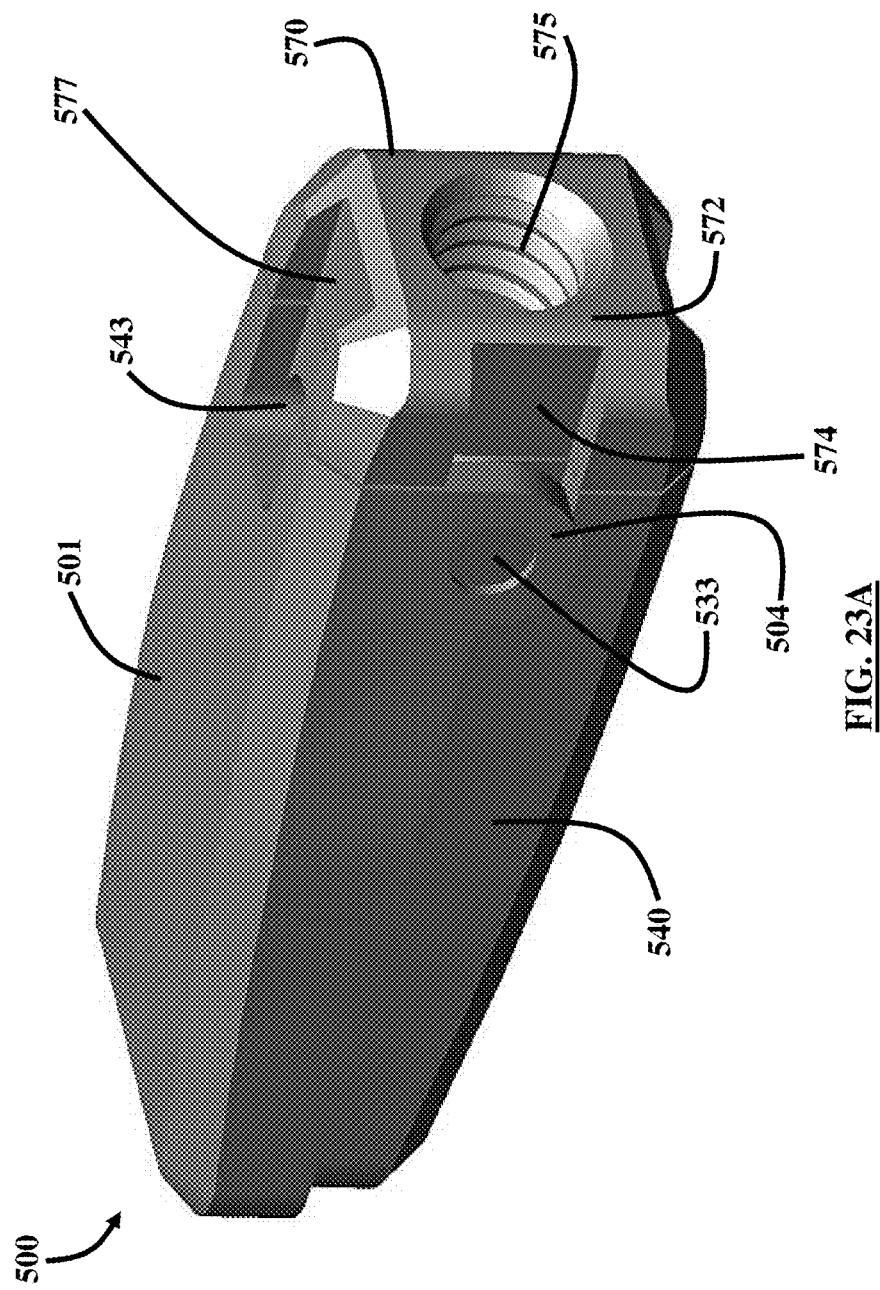
FIG. 23A illustrates a rear perspective view of an expandable interbody device in a closed configuration according to a fifth embodiment herein.
Figure 23B:
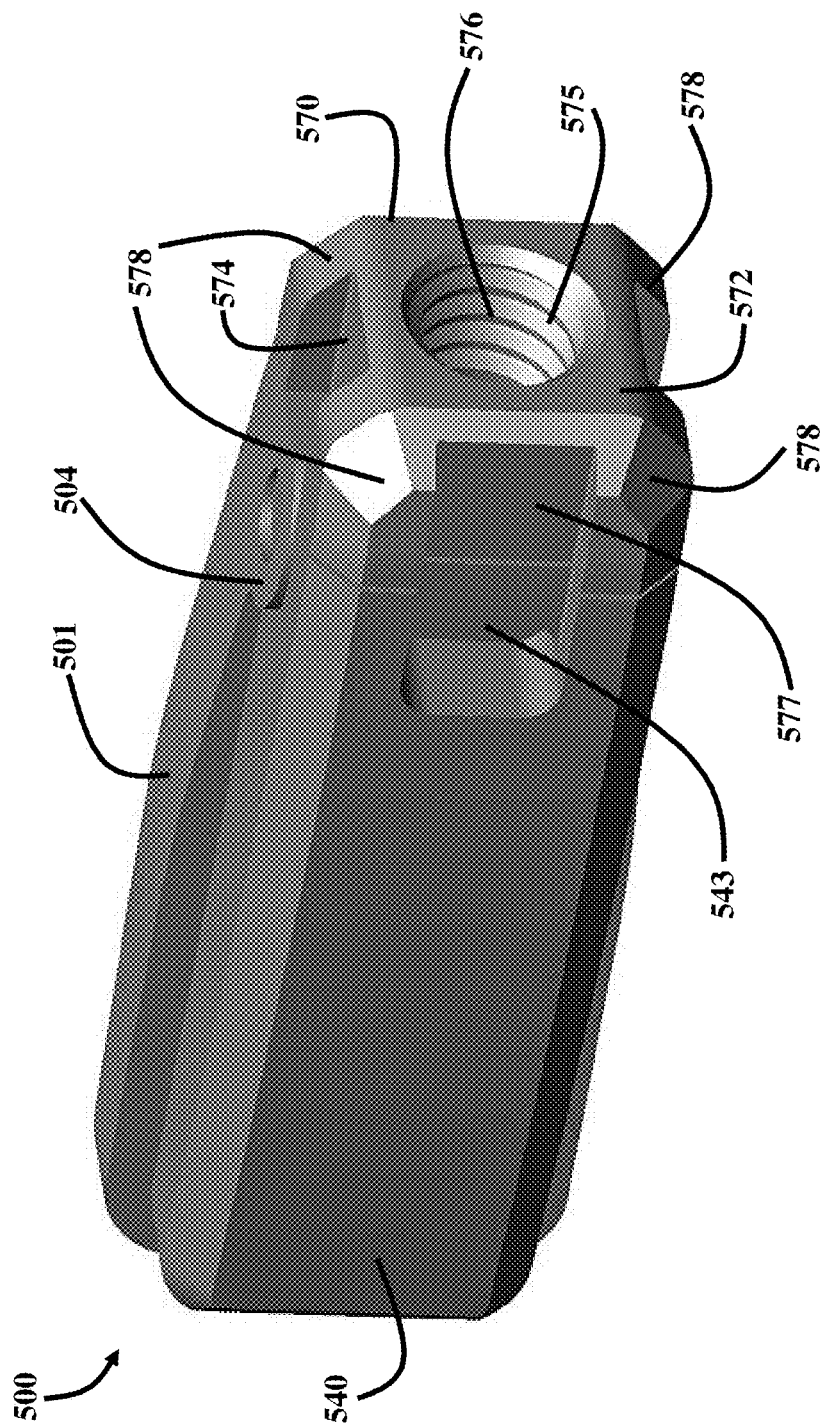
FIG. 23B illustrates a rear perspective view of a rotated expandable interbody device in a closed configuration according to a fifth embodiment herein.
Figure 23C:
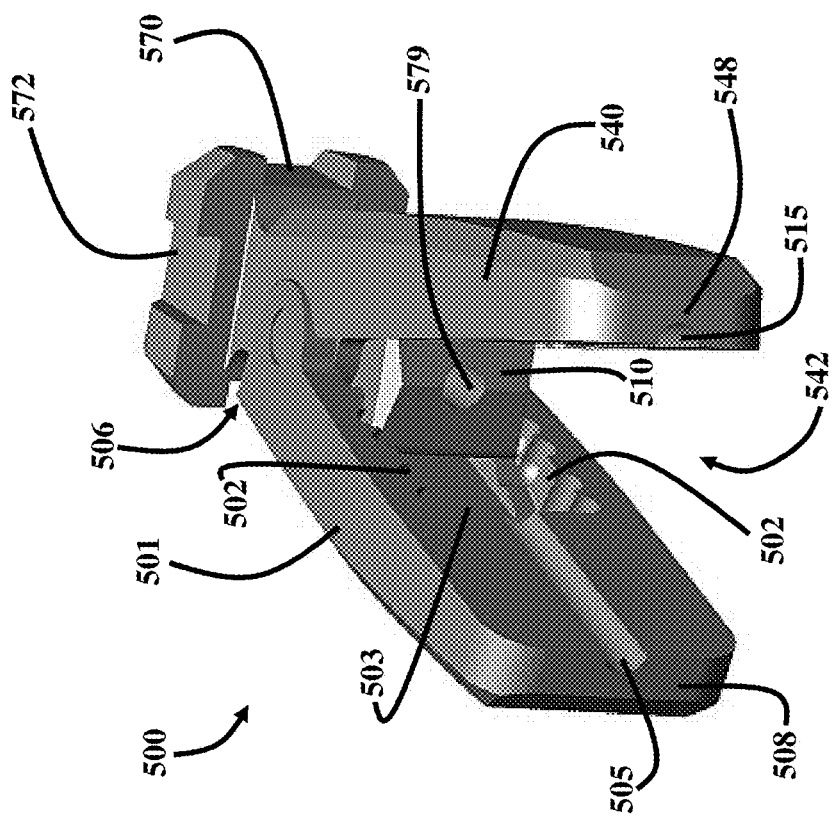
FIG. 23C illustrates a front perspective view of an expandable interbody device in an open configuration according to a fifth embodiment herein.

FIG. 23A illustrates a rear perspective view of an expandable interbody device 500 in a closed configuration according to a fifth embodiment herein. The interbody device 500 comprises a first articulating member 501 rotatably connected via a pair of pins 533 to a second articulating member 540. A clip member 570 is configured to engage both the first articulating member 501 and the second articulating member 540. FIG. 23B illustrates a rear perspective view of a rotated expandable interbody device 500 in a closed configuration according to a fifth embodiment herein. FIG. 23C illustrates a front perspective view of an expandable interbody device 500 in an open configuration according to a fifth embodiment herein. In these embodiments, the first articulating member 501 is dimensioned and configured to be larger than the second articulating member 540 (e.g., the edges of the first articulating member 501 generally extend beyond the edges of the second articulating member 540). The clip member 570 includes a threaded hole 575 to receive an inserter device (e.g., such as inserter device 80 of FIGS. 17A through 22B). The clip member 570 is configured to cause the first and second articulating members 501, 540 to rotate (or "expand") relative to each other.

The first and second articulating members 501, 540 each comprise a small cutout area 543. The clip member 14 further comprises a head portion 572 having the threaded hole 575 disposed through a substantially central portion thereof. The hole 575 comprises threads 576, and the head portion 32 comprises four prong edges 578 separated by cutout areas 574, 577 such that cutout area 577 aligns with cutout areas 543 of the first and second articulating members 501, 540. The cutout area 574 is adjacent to the pin sockets 504 of the first articulating member 501 (the second articulating member 540 also includes complementary pin sockets, which are not shown in FIGS. 23A through 23C, but which align with the pin sockets 504 of the first articulating member 501 to retain the pins 533). As shown in FIG. 23C, once the interbody device 500 begins to open, the relative rotational movement of the first articulating member 501 and the second articulating member 540 create an angled opening 542 between the first articulating member 540 and the second articulating member 542, and also create a separation between the head portion 572 of the clip member 570 and each of the first and second articulating members 501, 540. The angled opening 542 and separation 506 are created when an inserter device (e.g., inserter device 80 of FIGS. 17A through 22B) engages the threaded hole 575 of the clip member 570 and begins pulling the clip member 570 laterally away from the first and second articulating members 501, 540 such that the protruding member 510 of the clip member 570 progressively slides in a clicking manner along the grooves 502 configured in the inner portion 503 of the first and second articulating members 501, 540.

Figure 24:
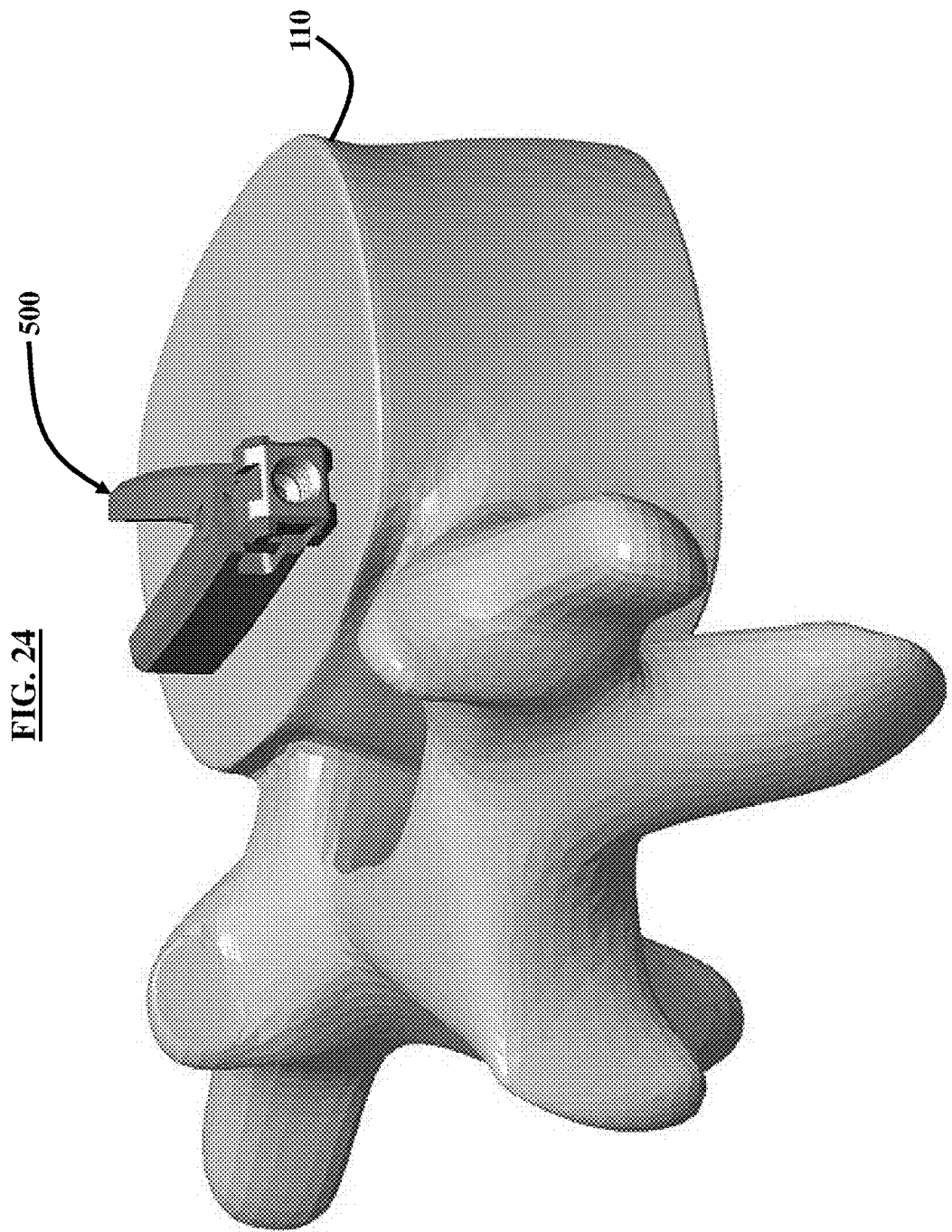
FIG. 24 illustrates a perspective view of the expandable interbody device of FIGS. 23A through 23C adjacent to a vertebral body according to a fifth embodiment herein.
Figure 26I:
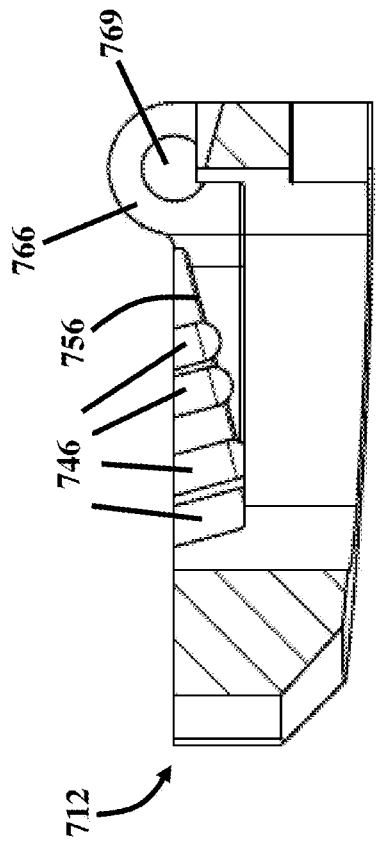
FIG. 26I illustrates a cross-sectional view cut along line A-A of the expandable interbody device of FIG. 26H according to a sixth embodiment herein.
Figure 26H:
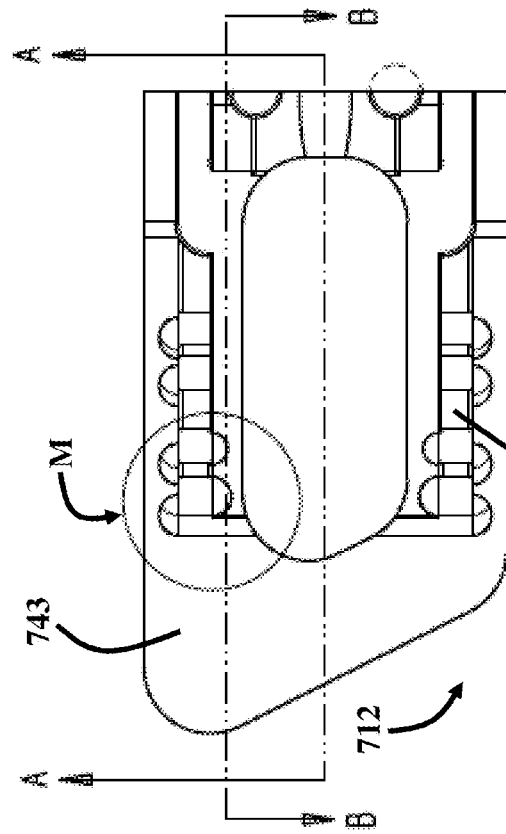
FIG. 26H illustrates a magnified bottom plan view of the second articulating member of FIG. 26B of the expandable interbody device of FIGS. 25A through 25B according to a sixth embodiment herein.
Figure 26J:
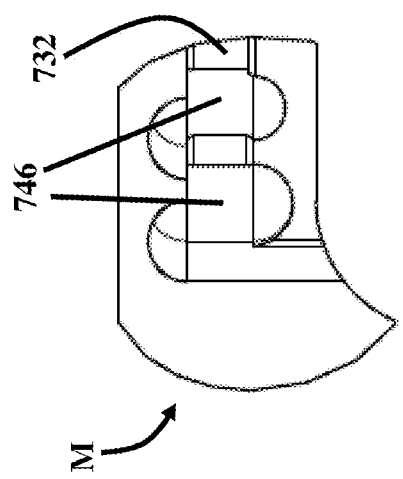
FIG. 26J illustrates an isolated magnified view of the encircled area M of the expandable interbody device of FIG. 26H according to a sixth embodiment herein.
Figure 26K:
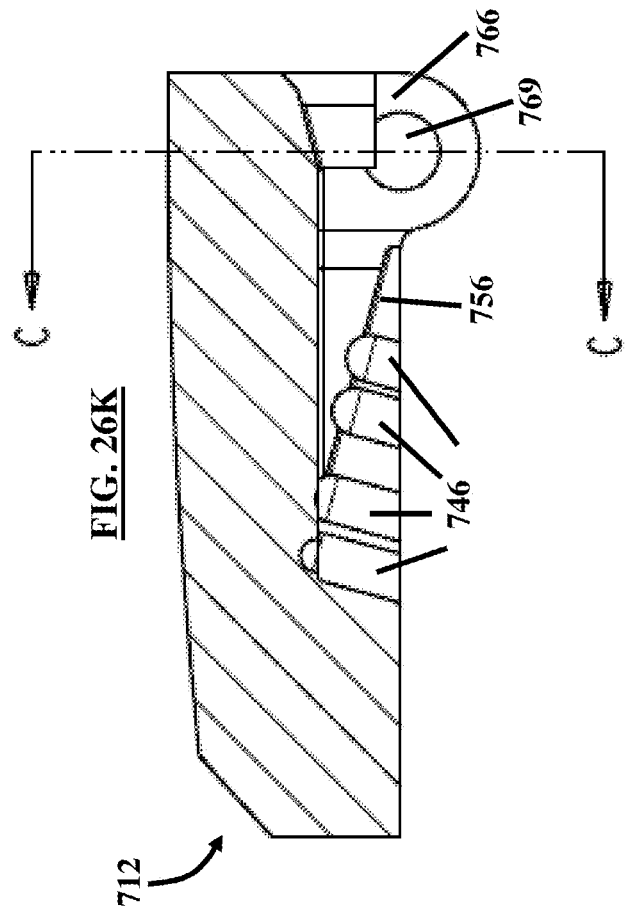
FIG. 26K illustrates a cross-sectional view cut along line B-B of the expandable interbody device of FIG. 26H according to a sixth embodiment herein.
Figure 26L:
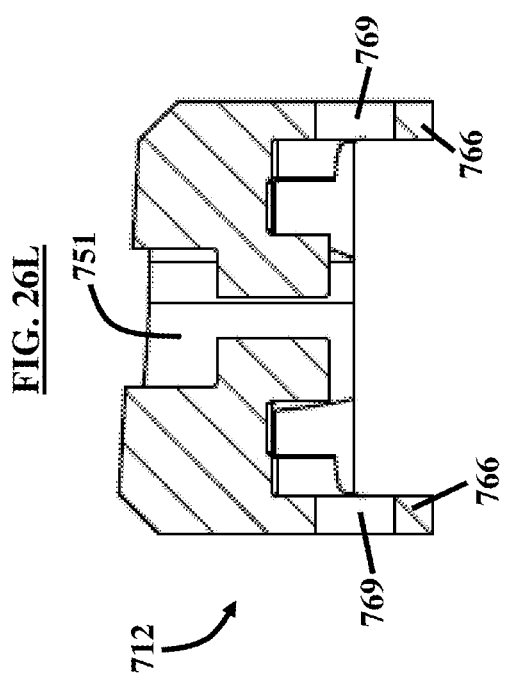
FIG. 26L illustrates a cross-sectional view cut along line C-C of the expandable interbody device of FIG. 26K according to a sixth embodiment herein.
Figure 27I:
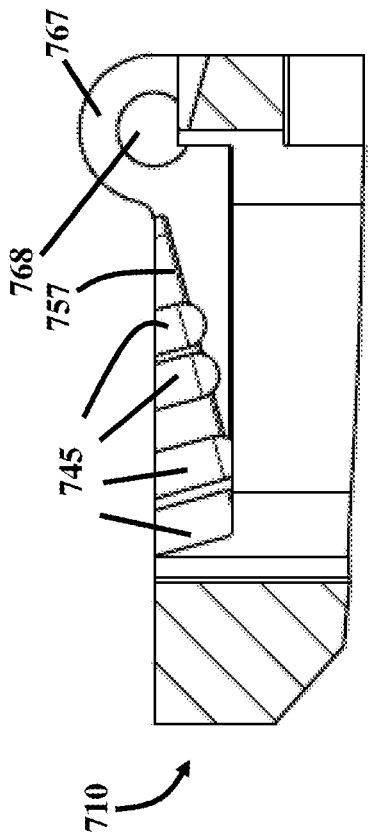
FIG. 27I illustrates a cross-sectional view cut along line E-E of the expandable interbody device of FIG. 27H according to a sixth embodiment herein.
Figure 27J:
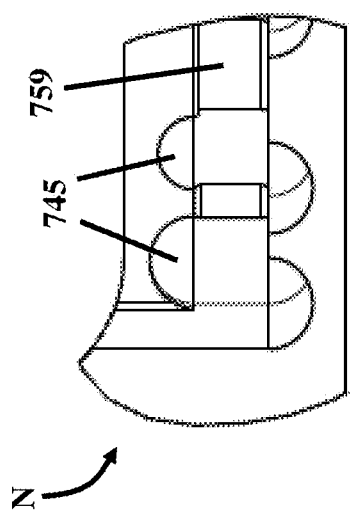
FIG. 27J illustrates an isolated magnified view of the encircled area N of the expandable interbody device of FIG. 27H according to a sixth embodiment herein.
Figure 27H:
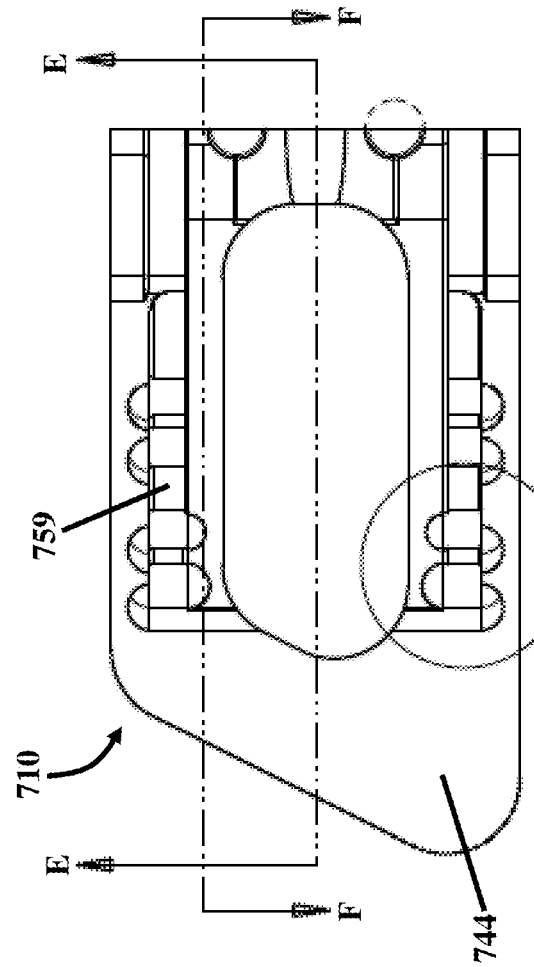
FIG. 27H illustrates a magnified bottom plan view of the first articulating member of FIG. 27B of the expandable interbody device of FIGS. 25A through 25B according to a sixth embodiment herein.
Figure 27K:
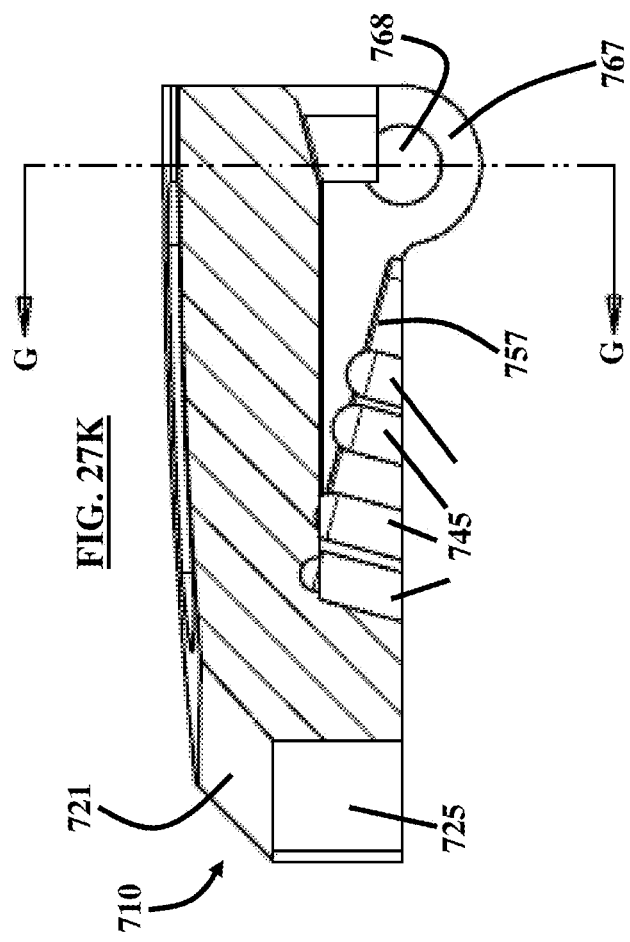
FIG. 27K illustrates a cross-sectional view cut along line F-F of the expandable interbody device of FIG. 27H according to a sixth embodiment herein.
Figure 27L:
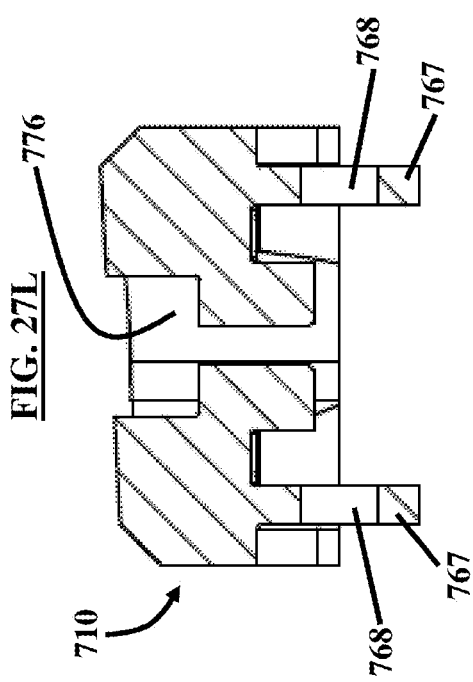
FIG. 27L illustrates a cross-sectional view cut along line G-G of the expandable interbody device of FIG. 27K according to a sixth embodiment herein.
Figure 27N:
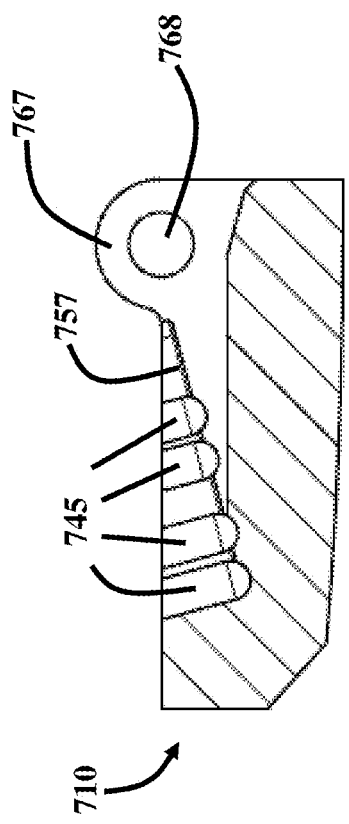
FIG. 27N illustrates a cross-sectional view cut along line H-H of the expandable interbody device of FIG. 27M according to a sixth embodiment herein.
Figure 27M:
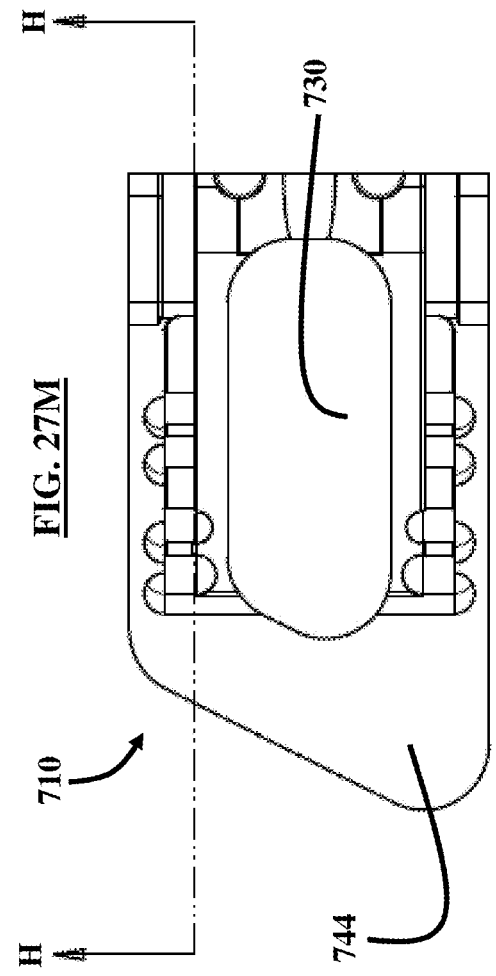
FIG. 27M illustrates another magnified bottom plan view of the first articulating member of FIG. 27B of the expandable interbody device of FIGS. 25A through 25B according to a sixth embodiment herein.
Figure 28G:
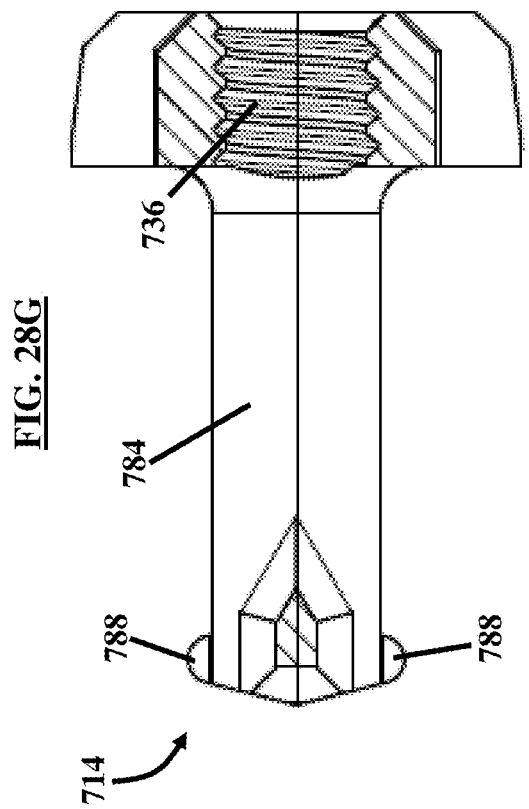
FIG. 28G illustrates a cross-sectional view cut along line J-J of the clip member of FIG. 28F according to a sixth embodiment herein.
Figure 28F:
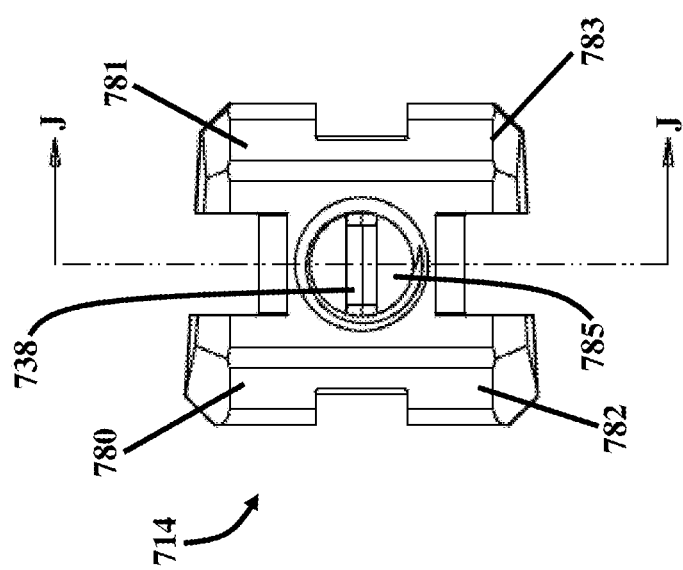
FIG. 28F illustrates a rear plan view of the clip member of FIG. 28A according to a sixth embodiment herein.

The protruding member 510 of the clip member 570 further comprises a hole 579 configured therein. Furthermore, the first articulating member 501 comprises a semi-circular groove 505 configured from the end wall 508 to the portion where the grooves 502 begin in the first articulating member 501. Likewise, the second articulating member 540 comprises a semi-circular groove 515 configured from the end wall 548 to the portion where the grooves 502 (not shown on the second articulating member 540 in FIGS. 23A through 23C) begin in the second articulating member 540. FIG. 24 illustrates a perspective view of the expandable interbody device 500 of FIGS. 23A through 23C in an open configuration adjacent to a vertebral body 110 according to a fifth embodiment herein. The embodiments shown in FIGS. 23A through 24 operate substantially the same as described with respect to the embodiments shown in FIGS. 9A through 22B as described above.

FIGS. 25A through 25C illustrate various views of an expandable interbody device 700 according to a sixth embodiment herein. FIG. 25A illustrates a perspective view of an expandable interbody device 700 according to a sixth embodiment herein. FIG. 25B illustrates a side view of the expandable interbody device 700 of FIG. 25A and FIG. 25C illustrates a cross-sectional view cut along line X-X of the expandable interbody device 700 of FIG. 25B according to a sixth embodiment herein.

The interbody device 700 comprises a first articulating member 710 and a second articulating member 712, which are rotationally connected to one another using a pair of pins 742. The interbody device 700 further includes a clip member 714 configured to cause the first and second articulating members 710, 712 to rotate (or "expand") relative to each other. The first and second articulating members 710, 712 as well as the clip member 714 generally comprise a smooth outer surface 716 in one embodiment. The first articulating member 710 and the second articulating member 712 are configured to align in a complementary manner to create a substantially uniform outer surface 716.

FIGS. 26A through 26M illustrate various views of the second articulating member 712 of the expandable interbody device 700 of FIGS. 25A through 25B according to a sixth embodiment herein. The second articulating member 712 comprises a second long sidewall 735 positioned opposite to a second short sidewall 717. The second long sidewall 735 comprises a top beveled edge 739. A second angled front wall 723 connects to a rounded corner 727, which connects to the second long sidewall 735. The second angled front wall 723 comprises a top beveled edge 719, and the rounded corner 727 comprises a top beveled edge 731. The second articulating member 712 also comprises a second short sidewall 717, which comprises a top beveled edge 747. The second angled front wall 723 further connects to a rounded corner 724, which connects to the second short sidewall 717.

The second articulating member 712 also includes a second hole 740 disposed generally through the middle of the second articulating member 712. The second articulating member 712 comprises a second inner face 743 comprising a first groove wall 726 and a second groove wall 728 such that the first groove wall 726 is part of the second short sidewall 717 of the second articulating member 712, and the second groove wall 728 is part of the second long sidewall 735 of the second articulating member 712. The first groove wall 726 and second groove wall 728 each comprise a second ramp portion 756 and a second set of grooves 746 arranged such that the grooves 746 are progressively elongated as they near the second angled front wall 723 side of the second articulating member 712. Furthermore, the configuration of the second set of grooves 746 corresponds with the "clicks" for the various stages of opening/engagement of the interbody device 700. Disposed between the grooves 746 is a second spacer 732. The progressively elongated configuration of the grooves 746 corresponds with the incline of the second ramp portion 756. A second inner sidewall 754 is disposed around the interior of the second articulating member 712 and defines the dimension and configuration of the second hole 740, wherein a terminating wall 751 is positioned opposite to the open end 750 of the second articulating member 712, which permits access by the clip member 714. The top 752 of the inner side wall 754 is spaced of sufficient thickness to allow a space between the grooves 746 and the hole 740. The second articulating member 712 further comprises a second raised bar 762 disposed on top of the second inner sidewall 754 and positioned at the open end 750 of the second articulating member 712 opposite from the terminating wall 751. Disposed on opposite sides of the second raised bar 762 are a second pair of sockets 766 respectively comprising a second pair of pin holes 769. A platform 760 is configured adjacent to the second pair of sockets 766. The second articulating member 712 further comprises a pair of rear guard walls 748, 749 which are separated by the second raised bar 762. The guard wall 748 is continuous with one socket 766 on the second long sidewall 735, and the guard wall 749 is continuous with another socket 766 on the second short sidewall 717. As shown in FIGS. 26F and 26G, the guard wall 748 is slightly elevated compared with the guard wall 749 such that the guard walls 748, 749 substantially slope down from the high end (guard wall 748) to the lower end (guard wall 749).

FIGS. 27A through 27M illustrate various views of the first articulating member 710 of the expandable interbody device 700 of FIGS. 25A through 25B according to a sixth embodiment herein. The first articulating member 710 comprises a first long sidewall 737 positioned opposite to a first short sidewall 773. The first long sidewall 737 comprises a top beveled edge 775. A first angled front wall 725 connects to a rounded corner 772, which connects to the first long sidewall 737. The first angled front wall 725 comprises a top beveled edge 721, and the rounded corner 772 comprises a top beveled edge 771. The first articulating member 712 also comprises a first short sidewall 773, which comprises a top beveled edge 774. The first angled front wall 725 further connects to a rounded corner 729, which connects to the first short sidewall 773.

The first articulating member 710 also includes a first hole 730 disposed generally through the middle of the first articulating member 710. When positioned together in the closed state, the first hole 730 of the first articulating member 710 and first hole 740 of the first articulating member 712 align to create a bone graft window for the interbody device 700.

The first articulating member 710 comprises a first inner face 744 comprising a first groove wall 755 and a first groove wall 758 such that the first groove wall 755 is part of the first short sidewall 773 of the first articulating member 710, and the first groove wall 758 is part of the first long sidewall 737 of the first articulating member 710. The first groove wall 755 and first groove wall 758 each comprise a first ramp portion 757 and a first set of grooves 745 arranged such that the grooves 745 are progressively elongated as they near the first angled front wall 725 side of the first articulating member 710. Furthermore, the configuration of the first set of grooves 745 corresponds with the "clicks" for the various stages of opening/engagement of the interbody device 700. Disposed between the grooves 745 is a first spacer 759. The progressively elongated configuration of the grooves 745 corresponds with the incline of the first ramp portion 757. A first inner sidewall 777 is disposed around the interior of the first articulating member 710 and defines the dimension and configuration of the first hole 730, wherein a terminating wall 776 is positioned opposite to the open end 770 of the first articulating member 710, which permits access by the clip member 714. The top 753 of the inner side wall 777 is spaced of sufficient thickness to allow a space between the grooves 745 and the hole 730. The first articulating member 710 further comprises a first raised bar 763 disposed on top of the first inner sidewall 777 and positioned at the open end 770 of the first articulating member 710 opposite from the terminating wall 776. Disposed on opposite sides of the first raised bar 763 are a first pair of sockets 767 respectively comprising a first pair of pin holes 768. A platform 761 is configured adjacent to the first pair of sockets 767. The first articulating member 710 further comprises a pair of rear guard walls 778, 779 which are separated by the first raised bar 763. The guard wall 778 is continuous with one socket 776 on the first long sidewall 737, and the guard wall 779 is continuous with another socket 776 on the first short sidewall 773. As shown in FIGS. 27F and 27G, the guard wall 779 is slightly elevated compared with the guard wall 778 such that the guard walls 778, 779 substantially slope down from the high end (guard wall 779) to the lower end (guard wall 778).

FIGS. 28A through 28K illustrate various views of the clip member 714 of the expandable interbody device 700 of FIGS. 25A through 25C according to a sixth embodiment herein. The clip member 714 further comprises a head portion 722 having a hole 785 disposed through a substantially central portion thereof. The hole 785 comprises threads 736 to receive and engage an inserter device (e.g., such as inserter device 80 of FIGS. 17A through 22B), and the head portion 722 comprises generally beveled edges 791 to further better match endplate anatomy. The head portion 722 further comprises a plurality of prongs 780, 781, 782, 783 such that the prongs 780 and 781 are larger in size than prongs 782, 783. A substantially flat gap wall 790 is configured in between each of the prongs 780, 781, 782, 783. Once the interbody device 700 begins to open, the relative rotational movement of the first articulating member 710 and the second articulating member 712 create an angled opening (not shown in FIGS. 25A through 28K) between the first articulating member 710 and the second articulating member 712, and also create a separation (not shown in FIGS. 25A through 28K) between the head portion 722 of the clip member 714 and each of the first and second articulating members 710, 712.

The back wall 792 of the head portion 722 comprises a pair of substantially parallel cantilever arms 784 outwardly protruding therefrom. The pair of arms 784 are appropriated spaced apart from each other to create a space 793 therebetween. The end 786 of each arm 784 comprises a prong 787 comprising opposed protruding tips 788 such that the height of each prong 787 is greater than the height of each arm 784, wherein the protruding tip 788 extends beyond the top 793 of the arms 784, and wherein the protruding tip 788 extends beyond the bottom 794 of the arms 784. A cross bar 738 connects the pair of arms 784 towards the end 786 side of the clip member 714. The cross bar 738 helps in prevent full extraction of the clip member 714 as it continues to click and slide in the grooves 745, 746.

The protruding tips 788 are dimensioned and configured to engage the various grooves 745, 746 of the respective first and second articulating members 710, 712 when the clip member 714 is inserted into and in between the first and second articulating members 710, 712. The clip member 714 is inserted into and in between the first and second articulating members 710, 712 such that the back wall 792 of the clip member 714 is adjacent to the open ends 770, 750 of the first and second articulating members 710, 712, respectively.

When the first articulating member 710 is aligned with the second articulating member 712 the various complementary components described above align with one another. For example, the second pair of sockets 766 of the second articulating member 712 each fit in the respective cut-out wells 789 of the first articulating member 710 such that the first pair of pin holes 768 of the first articulating member 710 aligns with the second pair of pin holes 769 of the second articulating member 712. This permits the pins 742 to be inserted to allow for rotational movement of the first articulating member 710 with respect to the second articulating member 712, but still allow for retention of the first articulating member 710 and second articulating member 712 together without separating completely. The platform 760 allows the first pair of sockets 767 to rest thereon upon alignment of the first articulating member 710 with the second articulating member 712. Furthermore, the various grooves 745 of the first articulating member 710 align with the correspondingly configured grooves 746 of the second articulating member 712 upon alignment of the first articulating member 710 with the second articulating member 712. Additionally, the first raised bar 763 and second raised bar 762 also align together as does the first hole 730 with the second hole 740.

In one embodiment, the first and second ramp portions 757, 756 and grooves 745, 746 may be configured on only one of the articulating members (e.g., either articulating member 710 or articulating member 712) (not shown) rather than both members 710, 712 as indicated in the drawings. In such an embodiment, the clip member 714 would only have a protruding tip 788 on one side of the prong (e.g., either the top or bottom) not both. Furthermore, in another embodiment (not shown), there could be an upward protruding tip 788 on one prong 787 and a downward protruding tip 788 on the other prong 787 on opposite sides of the pair of arms 784.

The major positional control of the clip member 714 within the interbody device 700 is controlled by the protruding tips 788 in the timed associated grooves 745, 746 of the interrupted ramp portions 757, 756. The prong 787 of the clip member 714 may sit in these grooves 745, 746 with some clearance, however the protruding tips 788 are what click and control the position of the clip member 714, one groove 745 being on the first articulating member 710 and the other groove 746 on the second articulating member 712, the tips 788 sitting in the pair of grooves 745, 746. The embodiments shown in FIGS. 25A through 28K operate substantially the same as described with respect to the embodiments shown in FIGS. 9A through 24 as described above.

FIG. 29, with reference to FIGS. 1 through 28K, illustrates a flowchart of a method of expanding an interbody (e.g., interbody 700) according to an embodiment herein. The method comprises providing (800) a first articulating member (e.g., member 710); rotatably connecting (802) a second articulating member (e.g., member 712) to the first articulating member (e.g., member 710), wherein any of the first articulating member (e.g., member 710) and the second articulating member (e.g., member 712) comprises a plurality of grooves (e.g., grooves 745, 746) arranged in a progressively elongated arrangement; and retracting (804) a clip member (e.g., member 714) that is inserted in between the first articulating member (e.g., member 710) and the second articulating member (e.g., member 712), wherein the clip member (e.g., member 714) comprises at least one protruding tip (e.g., tip 788) that sequentially engages the plurality of grooves (e.g., grooves 745, 746) causing the first articulating member (e.g., member 710) to rotate with respect to the second articulating member (e.g., member 712). Rotation of the first articulating member (e.g., member 710) with respect to the second articulating member (e.g., member 712) may create an angled opening (e.g., an opening similar to opening 542) between the first articulating member (e.g., member 710) and the second articulating member (e.g., member 710). The method may further comprise using an inserter device (e.g., device 80) to extract the clip member (e.g., member 714) from the first and second articulating members (e.g., members 710, 712). The method may further comprise the clip member (e.g., member 714) terminating extraction from the first and second articulating members (e.g., members 710, 712) upon the at least one protruding tip (e.g., tip 788) engaging a last groove of the plurality of grooves (e.g., grooves 745, 746).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An expanding interbody comprising:
   a first articulating member;
   a second articulating member rotatably connected to said first articulating member about a hinge;
   a clip member that engages each of said first articulating member and said second articulating member, wherein said first articulating member and said second articulating member each comprises an inner face having a ramp portion and a plurality of grooves arranged in an increasingly elongated arrangement as the plurality of grooves of said first articulating member are aligned with the plurality of grooves of said second articulating member, wherein the increasingly elongated arrangement of grooves corresponds to the ramp portion, wherein said clip member comprises protruding tips that sequentially engages the plurality of grooves of said first articulating member and said second articulating member, wherein the protruding tips engage the longest grooves of the increasingly elongated arrangement of grooves prior to extraction of the clip member, and wherein extraction of the clip member from the first and second articulating members causes said first articulating member to rotate angularly and expand open with respect to said second articulating member without expansion of said first articulating member and said second articulating member about the hinge.

2. The expanding interbody of claim 1, wherein rotation of said first articulating member with respect to said second articulating member creates an angled opening between said first articulating member and said second articulating member.

3. The expanding interbody of claim 1, wherein said clip member comprises a head portion comprising:
   a plurality of prongs, wherein a first pair of said plurality of prongs are dimensioned and configured to be larger than a second pair of said plurality of prongs;
   a threaded hole substantially positioned in a center of said head portion; and
   a pair of cantilever arms extending from said head portion and positioned on opposite sides of said threaded hole.

4. The expanding interbody of claim 3, wherein said pair of cantilever arms comprises a cross bar connecting said pair of cantilever arms together.

5. The expanding interbody of claim 1, wherein said first articulating member and said second articulating member are complimentarily dimensioned and configured to one another.

6. The expanding interbody of claim 1, wherein any of said first articulating member and said second articulating member comprises:
   a first sidewall having a first length;
   a second sidewall oppositely positioned from said first sidewall and having a second length smaller than said first length;
   a hole separating said first sidewall from said second sidewall;
   a pair of sockets comprising a hole; and
   said plurality of grooves configured in said first sidewall and said second sidewall.

7. The expanding interbody of claim 1, wherein said first articulating member comprises a first pair of sockets comprising a first pair of holes, wherein said second articulating member comprises a second pair of sockets comprising a second pair of holes, and wherein the holes of said first pair of sockets align with the holes of said second pair of sockets.

8. The expanding interbody of claim 6, wherein any of said first articulating member and said second articulating member comprises a pair of walls connected to said pair of sockets, wherein said pair of walls are separated by a gap therebetween, and wherein a first wall of said pair of walls comprises a height greater than a height of a second wall of said pair of walls.

9. The expanding interbody of claim 8, wherein a top of said pair of walls are angled such that said top is not planar.

10. An expanding interbody comprising:
    a first articulating member;
    a second articulating member rotatably connected to said first articulating member about a hinge, wherein said first articulating member and said second articulating member are complimentarily dimensioned and configured to one another;
    a clip member that engages each of said first articulating member and said second articulating member, wherein said first articulating member and said second articulating member each comprises an inner face having a ramp portion and a plurality of grooves arranged in an increasingly elongated arrangement as the plurality of grooves of said first articulating member are aligned with the plurality of grooves of said second articulating member, wherein the increasingly elongated arrangement of grooves corresponds to the ramp portion, wherein said clip member comprises protruding tips that sequentially engages the plurality of grooves on said first articulating member and said second articulating member, wherein the protruding tips engage the longest grooves of the increasingly elongated arrangement of grooves prior to extraction of the clip member, and wherein extraction of said clip member causes rotation of said first articulating member with respect to said second articulating member and creates an angled opening between said first articulating member and said second articulating member without expansion of said first articulating member and said second articulating member about the hinge.

11. The expanding interbody of claim 10, wherein said clip member comprises:
   a plurality of prongs, wherein a first pair of said plurality of prongs are dimensioned and configured to be larger than a second pair of said plurality of prongs;
   a threaded hole substantially positioned in a center of said head portion;
   a pair of cantilever arms extending from said head portion and positioned on opposite sides of said threaded hole; and
   a cross bar connecting said pair of cantilever arms together.

12. The expanding interbody of claim 10, wherein any of said first articulating member and said second articulating member comprises:
   a first sidewall having a first length;
   a second sidewall oppositely positioned from said first sidewall and having a second length smaller than said first length;
   a hole separating said first sidewall from said second sidewall;
   a pair of sockets comprising a hole; and
   said plurality of grooves configured in said first sidewall and said second sidewall.

13. The expanding interbody of claim 10, wherein said first articulating member comprises a first pair of sockets comprising a first pair of holes, wherein said second articulating member comprises a second pair of sockets comprising a second pair of holes, wherein the holes of said first pair of sockets align with the holes of said second pair of sockets.

14. The expanding interbody of claim 12, wherein any of said first articulating member and said second articulating member comprises a pair of walls connected to said pair of sockets, wherein said pair of walls are separated by a gap therebetween, wherein a first wall of said pair of walls comprises a height greater than a height of a second wall of said pair of walls, and wherein a top of said pair of walls are angled such that said top is not planar.

15. A method of expanding an interbody, said method comprising:
   providing a first articulating member;
   rotating a second articulating member connected to said first articulating member about a hinge, wherein any of said first articulating member and said second articulating member comprises a ramp portion and a plurality of grooves arranged in an increasingly elongated arrangement along the ramp portion; and
   extracting a clip member that is inserted in between said first articulating member and said second articulating member, wherein said clip member comprises at least one protruding tip that sequentially engages said plurality of grooves causing said first articulating member to rotate angularly with respect to said second articulating member without said first articulating member and said second articulating member expanding about the hinge, wherein the at least one protruding tip engages the longest grooves of the increasingly elongated arrangement of grooves prior to extracting the clip member.

16. The method of claim 15, wherein rotation of said first articulating member with respect to said second articulating member creates an angled opening between said first articulating member and said second articulating member.

17. The method of claim 15, further comprising using an inserter device to extract said clip member from said first and second articulating members.

18. The method of claim 15, further comprising said clip member terminating extraction from said first and second articulating members upon said at least one protruding tip engaging a last groove of said plurality of grooves.

\* \* \* \* \*